US012590950B2

(12) United States Patent
Jerry et al.

(10) Patent No.: US 12,590,950 B2
(45) Date of Patent: Mar. 31, 2026

(54) METHODS FOR PREDICTING ER-MEDIATED DNA DAMAGE

(71) Applicant: UNIVERSITY OF MASSACHUSETTS, Boston, MA (US)

(72) Inventors: D. Joseph Jerry, Boston, MA (US); Prabin Kumar Dhangada Majhi, Boston, MA (US); Aman Sharma, Boston, MA (US); Karen A. Dunphy, Boston, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 1095 days.

(21) Appl. No.: 17/068,205

(22) Filed: Oct. 12, 2020

(65) Prior Publication Data
US 2021/0109085 A1 Apr. 15, 2021

Related U.S. Application Data
(60) Provisional application No. 62/914,110, filed on Oct. 11, 2019.

(51) Int. Cl.
| G01N 33/50 | (2006.01) |
| A61K 31/138 | (2006.01) |
| C07K 16/44 | (2006.01) |
| G01N 33/483 | (2006.01) |
| G01N 33/574 | (2006.01) |

(52) U.S. Cl.
CPC ....... *G01N 33/5008* (2013.01); *A61K 31/138* (2013.01); *C07K 16/44* (2013.01); *G01N 33/4833* (2013.01); *G01N 33/57415* (2013.01)

(58) Field of Classification Search
CPC ........... G01N 33/5008; G01N 33/4833; G01N 33/57415; A61K 31/138; C07K 16/44
See application file for complete search history.

(56) References Cited

U.S. PATENT DOCUMENTS

| 3,817,837 | A | 6/1974 | Rubenstein et al. |
| 3,850,752 | A | 11/1974 | Schuurs et al. |
| 3,939,350 | A | 2/1976 | Kronick et al. |
| 3,996,345 | A | 12/1976 | Ullman et al. |
| 4,275,149 | A | 6/1981 | Litman et al. |
| 4,277,437 | A | 7/1981 | Maggio |
| 4,366,241 | A | 12/1982 | Tom et al. |

FOREIGN PATENT DOCUMENTS

WO WO-2011130381 A1 * 10/2011 ....... G01N 33/57415

OTHER PUBLICATIONS

Iso, Takako et al. "DNA damage caused by bisphenol A and estradiol through estrogenic activity." Biological & pharmaceutical bulletin vol. 29,2 (2006): 206-10. doi:10.1248/bpb.29.206 (Year: 2006).*

Chang, Bo Yoon et al. "The Effect of Selective Estrogen Receptor Modulators (SERMs) on the Tamoxifen Resistant Breast Cancer Cells." Toxicological research vol. 27,2 (2011): 85-93. doi:10.5487/TR.2011.27.2.085 (Year: 2011).*

Nazarali, Safia A, and Steven A Narod. "Tamoxifen for women at high risk of breast cancer." Breast cancer (Dove Medical Press) vol. 6 29-36. Feb. 17, 2014, doi:10.2147/BCTT.S43763 (Year: 2014).*

Rocca, Andrea et al. "Clinical utility of fulvestrant in the treatment of breast cancer: a report on the emerging clinical evidence." Cancer management and research vol. 10 3083-3099. Aug. 30, 2018, doi:10.2147/CMAR.S137772 (Year: 2018).*

Joseph et al., "Disruption of Partly-Induced Tumor Suppressor Pathways by Xenoestrogen Exposures" Grant No. 5U01ES026140-03. National Cancer Institute Division of Cancer Control and Population Science. (Year: 2017).*

Dunphy et al., "Abstract 3750: Xenoestrogens cause estrogen receptor-dependent R-loop formation and DNA damage" Poster presentation. AACR 2018 Annual meeting vol. 78 issue 13 supplemental (2018). https://doi.org/10.1158/1538-7445.AM2018-3750 (Year: 2018).*

Alamer, Maha, et al., "Effects of exposure to six chemical ultraviolet filters commonly used in personal care products on motility of MCF-7 and MDA-MB-231 human breast cancer cells in vitro," Journal of Applied Toxicology, vol. 38 (2017), pp. 148-159.

Barr., L., et al., "Measurement of paraben concentrations in human breast tissue at serial locations across the breast from axilla to sternum," Journal of Applied Toxicology, vol. 32 (2012), pp. 219-232.

Bhatia, Vaibhav, et al., BRCA2 prevents R-loop accumulation and associates with TREX-2 mRNA export factor PCID2, Nature, vol. 511 (2014), pp. 362-365.

Calafat, Antonia M., et al., "Concentrations of the Sunscreen Agent Benzophenone-3 in Residents of the United States: National Health and Nutrition Examination Survey 2003-2004," Environmental Health Perspectives, vol. 116, No. 7 (2008), pp. 893-897.

Calafat, Antonia, M., et al., "Urinary Concentrations of Four Parabens in the U.S. Population: NHANES 2005-2006," Environmental Health Perspectives, vol. 118, No. 5, pp. 679-685.

Cavalieri, Ercole L., et al., "Depurinating estrogen-DNA adducts, generators of cancer initiation: their minimization leads to cancer prevention," Clininical and Translational Medicine, vol. 5 (2016) (15 pages).

Cohen, Sarah, et al., "Senataxin resolves RNA:DNA hybrids forming at DNA double-strand breaks to prevent translocations," Nature Communications, vol. 9 (2018) (14 pages).

(Continued)

Primary Examiner — Gregory S Emch
Assistant Examiner — Mckenzie A Dunn
(74) Attorney, Agent, or Firm — Thomas I Horstemeyer, LLP

(57) ABSTRACT

Acute exposure to estrogenic chemicals is shown herein to induce DNA damage mediated by formation of ERα-dependent R-loops. Disclosed herein are methods for evaluating the safety and activity of a xenoestrogen. Also disclosed are methods for identifying subject particularly susceptible to the genotoxic effects of endogenous estrogens or environmental xenoestrogens. This method can be used to select suitable hormone therapies, such as a selective estrogen receptor modulator (SERM), aromatase inhibitor, or selective estrogen receptor degrader (SERD).

5 Claims, 30 Drawing Sheets
Specification includes a Sequence Listing.

(56)  References Cited

OTHER PUBLICATIONS

Cuzick, J., "A Brief Review of the International Breast Cancer Intervention Study (IBIS), the Other Current Breast Cancer Prevention Trials, and Proposals for Future Trials," European Journal of Cancer, vol. 26, (2000), pgs. (11 pages).

Janjua, Nadeem Rezaq, et al., "Systemic Absorption of the Sunscreens Benzophenone-3, Octyl-Methoxycinnamate, and 3-(4-Methyl-Benzylidene) Camphor After Whole-Body Topical Application and Reproductive Hormone Levels in Humans," Journal of Investigative Dermatology, vol. 123 (2004), pp. 57-61.

Kerdivel, Gwenneg, et al., "Estrogenic Potency of Benzophenone UV Filters in Breast Cancer Cells: Proliferative and Transcriptional Activity Substantiated by Docking Analysis," PLoS ONE, vol. 8, Issue 4 (2013), (13 pages).

Khanna, Sugandha, et al., "Exposure to parabens at the concentration of maximal proliferative response increases migratory and invasive activity of human breast cancer cells in vitro," Journal of Applied Toxicology, vol. 34 (2014), pp. 1051-1059.

Kim, Hyoung-June, et al., "Phosphodiesterase 4B plays a role in benzophenone-3-induced phototoxicity in normal human keratinocytes," Toxicology and Applied Pharmacology vol. 338 (2018), , pp. 174-181.

Kunisue, Tatsuya, et al., "Urinary Concentrations of Benzophenone-type UV Filters in U.S. Women and Their Association with Endometriosis," Environmental Science & Technology, vol. 46 (2012), pp. 4624-4632.

Laplante, Charlotte D., et al., "Oxybenzone Alters Mammary Gland Morphology in Mice Exposed During Pregnancy and Lactation," Journal of the Endocrine Society, vol. 2, Issue 8 (2018), pp. 903-921.

Liao, Chunyang, et al., "Widespread Occurrence of Benzophenone-Type UV Light Filters in Personal Care Products from China and the United States: an Assessment of Human Exposure," Environ. Sci. Technol., No. 48 (2014), pp. 4103-4109.

Liehr, Joachim G., et al., "Inhibition of Estrogen-induced Renal Carcinogenesis in Male Syrian Hamsters by Tamoxifen without Decrease in DNA Adduct Levels," Cancer Research, vol. 48 (1988). pp. 779-783.

Schlumpf, Margret, et al., "Exposure patterns of UV filters, fragrances, parabens, phthalates, organochlor pesticides, PBDEs, and PCBs in human milk: correlation of UV filters with use of cosmetics," Chemosphere vol. 81, pp. 1171-1183.

Majewski, Aliza R., et al., "Sterilization of Silastic Capsules Containing 17beta-Estradiol for Effective Hormone Delivery in Mus musculus," Journal of the American Association for Laboratory Animal Science, vol. 57, No. 6 (2018), (7 pages).

Martín, José Manuel Pérez, et al., "Oxidative DNA damage contributes to the toxic activity of propylparaben in mammalian cells," Mutation Research/Genetic Toxicology and Environmental Mutagenesis, vol. 702 (2010), pp. 86-91.

Martino, Silvana, et al., "Continuing Outcomes Relevant to Evista: Breast Cancer Incidence in Postmenopausal Osteoporotic Women in a Randomized Trial of Raloxifene," Journal of the National Cancer Institute, vol. 96, No. 23 (2004), pp. 1751-1761.

Matta, Murali K., et al., "Effect of Sunscreen Application Under Maximal Use Conditions on Plasma Concentration of Sunscreen Active Ingredients: a Randomized Clinical Trial," JAMA Preliminary Communication (2019) (10 pages).

Meerbrey, Kristin L., et al., "The pINDUCER lentiviral toolkit for inducible RNA interference in vitro and in vivo," PNAS, vol. 108, No. 9 (2011), pp. 3665-3670.

Schock, Helena, et al., "Hormone concentrations throughout uncomplicated pregnancies: a longitudinal study," BMC Pregnancy Childbirth, vol. 16 (2016) (11 pages).

O'leary, Peter, et al., "Longitudinal Assessment of Changes in Reproductive Hormones during Normal Pregnancy," Clinical Chemistry, vol. 37, No. 5, pp. 667-672.

Pastor-Barriuso, Roberto, et al., "Total Effective Xenoestrogen Burden in Serum Samples and Risk for Breast Cancer in a Population-Based Multicase-Control Study in Spain," Environmental Health Perspectives, vol. 124, No. 10 (2016), pp. 1575-1582.

Periyasamy, Manikandan et al., "APOBEC3B-Mediated Cytidine Deamination Is Required for Estrogen Receptor Action in Breast Cancer," Cell Reports vol. 13 (2015), pp. 108-121.

Philippat, Claire, et al. "Prenatal Exposure to Environmental Phenols: Concentrations in Amniotic Fluid and Variability in Urinary Concentrations during Pregnancy," Environmental Health Perspectives vol. 121 (2013), pp. 1225-1231.

Shivji, Mahmud K.K., et al., "BRCA2 Regulates Transcription Elongation by RNA Polymerase II to Prevent R-Loop Accumulation," Cell Reports, vol. 22 (2018), pp. 1031-1039.

Rajapakse, Nissanka, et al. "Detection of DNA Strand Breaks and Oxidized DNA Bases at the Single-Cell Level Resulting from Exposure to Estradiol and Hydroxylated Metabolites," Environmental and Molecular Mutagenesis, vol. 45 (2005), pp. 397-404.

Roy, Deodutta, et al., "Estrogen, DNA damage and mutations," Mutation Research, vol. 424 (1999), pp. 107-115.

Russo, Jose, et al., "Estrogen and its metabolites are carcinogenic agents in human breast epithelial cells," Journal pf Steroid Biochemistry & Molecular Biology, vol. 87 (2003), (25 pages).

Santen, Richard, et al., "Estrogen Mediation of Breast Tumor Formation Involves Estrogen Receptor-Dependent, as Well as Independent, Genotoxic Effects,". Steriod Enzymes and Cancer: Ann. NY Academy of Sciences (2009), pp. 132-140.

Savage, Kienan I., et al., "BRCA1 Deficiency Exacerbates Estrogen-Induced DNA Damage and Genomic Instability," Cancer Research vol. 74, No. 10 (2014), pp. 2773-2784.

Tarazona, Isuha, et al., "Determination of benzophenone-3 and its main metabolites in human serum by dispersive liquid-liquid microextraction followed by liquid chromatography tandem mass spectrometry," Talanta, vol. 116 (2013), pp. 388-395.

Warth, Benedikt, et al., Metabolomics Reveals that Dietary Xenoestrogens Alter Cellular Metabolism Induced by Palbociclib/Letrozole Combination Cancer Therapy, Cell Chem. Biol., vol. 15 (2018), pp. 291-300.

Woodruff, Tracey J., et al. "Environmental Chemicals in Pregnant Women in the United States: NHANES 2003-2004," Environmental Health Perspectives, vol. 119, No. 6 (2011), pp. 878-885.

Byford, J.R., et al., Oestrogenic activity of parabens in MCF7 human breast cancer cells. J Steroid Biochem Mol Biol. Jan. 2002; 80(1): 49-60. doi: 10.1016/s0960-0760(01)00174-1. PMID: 11867263.

Clarke, R.B., et al., Estrogen sensitivity of normal human breast tissue in vivo and implanted into athymic nude mice: analysis of the relationship between estrogen-induced proliferation and progesterone receptor expression. Breast Cancer Res Treat. Sep. 1997;45(2):121-33. doi: 10.1023/a:1005805831460. PMID: 9342437.

Cumming, S.R., et al., The effect of raloxifene on risk of breast cancer in postmenopausal women: results from the MORE randomized trial. Multiple Outcomes of Raloxifene Evaluation. JAMA. Jun. 16, 1999;281(23):2189-97. doi: 10.1001/jama.281.23.2189. Erratum in: JAMA Dec. 8, 1999;282(22):2124. PMID: 10376571.

Dunphy, K.A., Inter-Individual Variation in Response to Estrogen in Human Breast Explants. J Mammary Gland Biol Neoplasia. Mar. 2020;25(1):51-68. doi: 10.1007/s10911-020-09446-3. Epub Mar. 9, 2020. PMID: 32152951; PMCID: PMC7147970.

The European Commission, Commission Regulation (EU) 2017/238 of Feb. 10, 2017 amending Annex VI to Regulation (EC) No. 1223/2009 of the European Parliament and of the Council on cosmetic products, Official Journal of the European Union.

The European Commission, Commission Regulation (EU) No. 1004/2014 of Sep. 18, 2014 amending Annex V to Regulation (EC) No. 1223/2009 of the European Parliament and of the Council on cosmetic products, Official Journal of the European Union.

Feinleib, M. Breast cancer and artificial menopause: a cohort study. J Natl Cancer Inst. Aug. 1968;41(2):315-29. PMID: 5671283.

Fullwood, M.J., et al., An oestrogen-receptor-alpha-bound human chromatin interactome. Nature. Nov. 5, 2009;462 (7269):58-64. doi: 10.1038/nature08497. PMID: 19890323; PMCID: PMC2774924.

Fussell, K.C., et al., Catechol metabolites of endogenous estrogens induce redox cycling and generate reactive oxygen species in breast

(56)                    References Cited

OTHER PUBLICATIONS epithelial cells. Carcinogenesis. Aug. 2011;32(8):1285-93. doi: 10.1093/carcin/bgr109. Epub Jun. 10, 2011. PMID: 21665890; PMCID: PMC3149209.

Gomez-Gonzalez, B., et al., Catechol metabolites of endogenous estrogens induce redox cycling and generate reactive oxygen species in breast epithelial cells. Carcinogenesis. Aug. 2011;32(8):1285-93. doi: 10.1093/carcin/bgr109. Epub Jun. 10, 2011. PMID: 21665890; PMCID: PMC3149209.

Gonzalez, H., et al., Percutaneous absorption of the sunscreen benzophenone-3 after repeated whole-body applications, with and without ultraviolet irradiation. Br J Dermatol. Feb. 2006;154(2):337-40. doi: 10.1111/j.1365-2133.2005.07007.x. PMID: 16433806.

Goodson, W.H., et al., Activation of the mTOR pathway by low levels of xenoestrogens in breast epithelial cells from high-risk women. Carcinogenesis. Nov. 2011;32(11):1724-33. doi: 10.1093/carcin/bgr196. Epub Sep. 1, 2011. PMID: 21890461; PMCID: PMC3204351.

Hatchi, E., et al., BRCA1 recruitment to transcriptional pause sites is required for R-loop-driven DNA damage repair. Mol Cell. Feb. 19, 2015;57(4):636-647. doi: 10.1016/j.molcel.2015.01.011. PMID: 25699710; PMCID: PMC4351672.

Huang, Y., et al., Epithelial to mesenchymal transition in human breast epithelial cells transformed by 17beta-estradiol. Cancer Res. Dec. 1, 2007;67(23):11147-57. doi: 10.1158/0008-5472.CAN-07-1371. PMID: 18056439.

Snodin, D., Regulatory risk assessments: Is there a need to reduce uncertainty and enhance robustness? Update on propylparaben in relation to its EU regulatory status. Hum Exp Toxicol. Oct. 2017; 36(10):1007-1014. doi: 10.1177/0960327117718042. Epub Jul. 11, 2017. PMID: 28695774.

Sollier, J, et al., Transcription-coupled nucleotide excision repair factors promote R-loop-induced genome instability. Mol Cell. Dec. 18, 2014;56(6):777-85. doi: 10.1016/j.molcel.2014.10.020. Epub Nov. 26, 2014. PMID: 25435140; PMCID: PMC4272638.

Townsend-Stork, C., et al., Co-transcriptional R-loops are the main cause of estrogen-induced DNA damage eLife 5:e17548. (2016).

Zhao, Z., et al., Mutagenic activity of 4-hydroxyestradiol, but not 2-hydroxyestradiol, in BB rat2 embryonic cells, and the mutational spectrum of 4-hydroxyestradiol. Chem Res Toxicol. Mar. 2006; 19(3):475-9. doi: 10.1021/tx0502645. PMID: 16544955.

Wan, Y., et al., Splicing function of mitotic regulators links R-loop-mediated DNA damage to tumor cell killing. J Cell Biol. Apr. 27, 2015;209(2):235-46. doi: 10.1083/jcb.201409073. PMID: 25918225; PMCID: PMC4411280.

Wang, Z., et al., Redox Cycling of Catechol Estrogens Generating Apurinic/Apyrimidinic Sites and 8-oxo-Deoxyguanosine via Reactive Oxygen Species Differentiates Equine and Human Estrogens, Chemical Research in Toxicology 2010 23 (8), 1365-1373, DOI: 10.1021/tx1001282.

Watanabe, Y., et al., Metabolism of UV-filter benzophenone-3 by rat and human liver microsomes and its effect on endocrine-disrupting activity. Toxicol Appl Pharmacol. Jan. 15, 2015;282(2):119-28. doi: 10.1016/j.taap.2014.12.002. Epub Dec. 17, 2014. PMID: 25528284.

Xu, X., et al., Quantitative Measurement of Endogenous Estrogens and Estrogen Metabolites in Human Serum by Liquid Chromatography—Tandem Mass Spectrometry, Analytical Chemistry 2007 79 (20), 7813-7821 DOI: 10.1021/ac070494j.

Yager, J.D., et al., Estrogen Carcinogenesis in Breast Cancer, Journal Article, 2006, New England Journal of Medicine, 270-282, 354-3.

Ye, X., et al., Parabens as urinary biomarkers of exposure in humans. Environ Health Perspect. Dec. 2006; 114 (12): 1843-6. doi: 10.1289/ehp.9413. PMID: 17185273; PMCID: PMC1764178.

Zhang, X, et al., Attenuation of RNA polymerase II pausing mitigates BRCA1-associated R-loop accumulation and tumorigenesis. Nat Commun 8, 15908 (2017). https://doi.org/10.1038/ncomms15908.

Zhao, X., Telomerase-immortalized human mammary stem/progenitor cells with ability to self-renew and differentiate. Proc Natl Acad Sci U S A. Aug. 10, 2010;107(32):14146-51. doi: 10.1073/pnas.1009030107. Epub Jul. 26, 2010. PMID: 20660721; PMCID: PMC2922525.

* cited by examiner

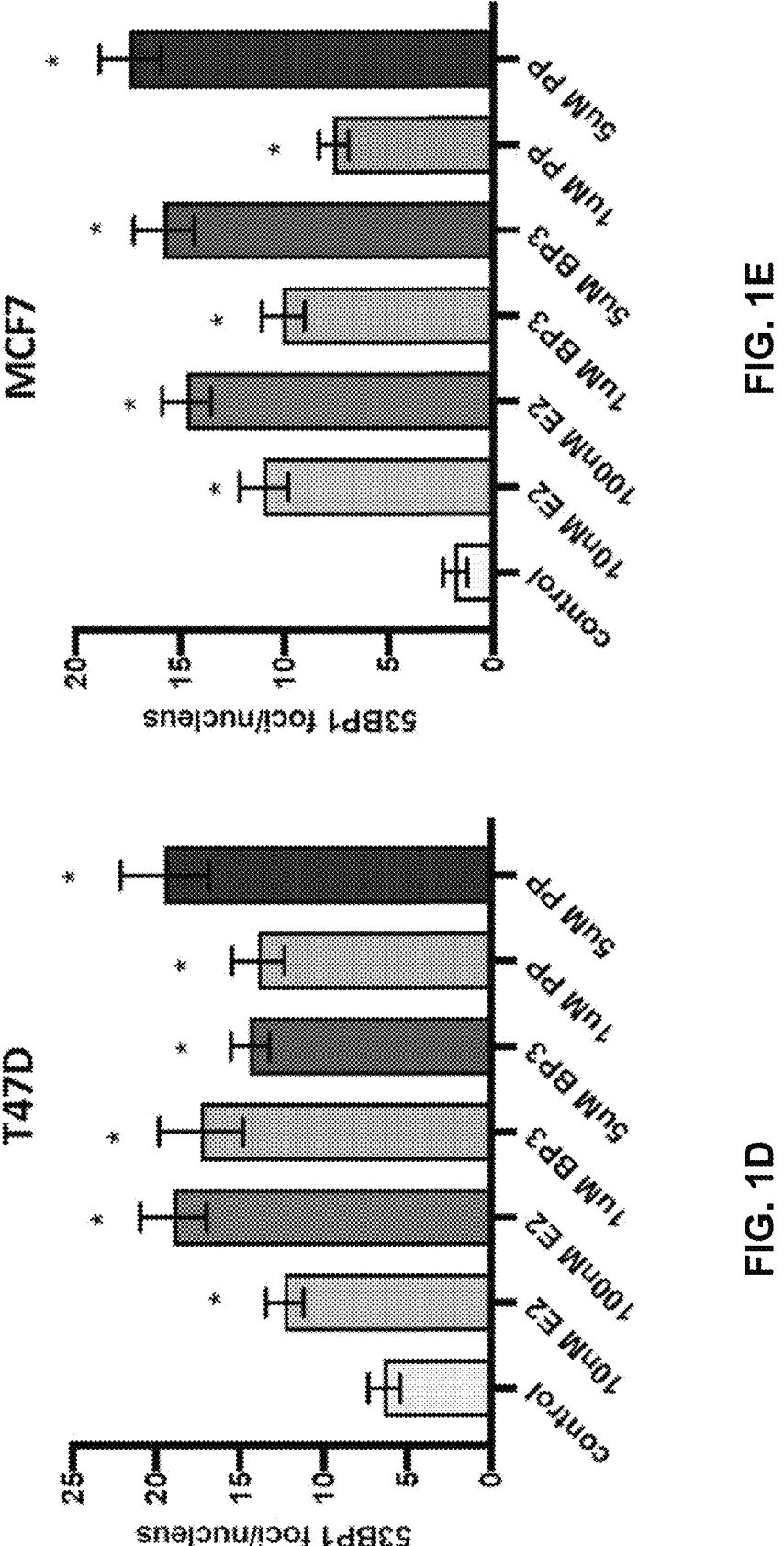

FIG. 6A

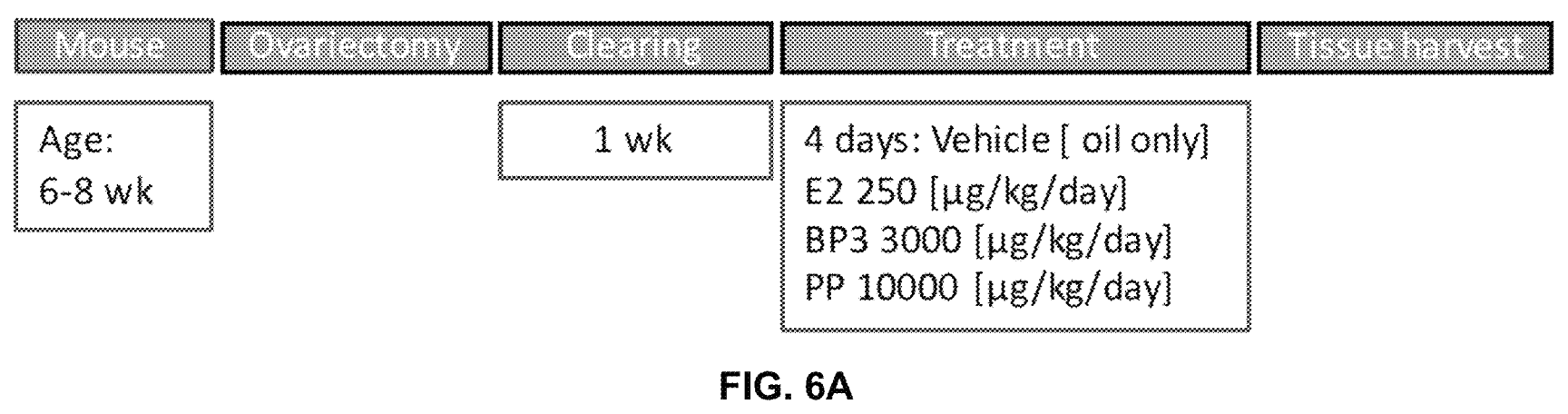

Mouse

Age: 6-8 wk

Ovariectomy

Grafting 1 wk

Treatment 4 days: Vehicle [ oil only]
E2 250 [µg/kg/day]
BP3 3000 [µg/kg/day]
PP 10000 [µg/kg/day]

Tissue harvest

METHODS FOR PREDICTING ER-MEDIATED DNA DAMAGE

STATEMENT REGARDING FEDERALLY SPONSORED RESEARCH OR DEVELOPMENT

This invention was made with government support under awards U01 ES026140 awarded by the National Institutes of Health and W81XWH-15-1-0217 awarded by the U.S. Army Medical Research and Materiel Command. The government has certain rights in the invention.

CROSS-REFERENCE TO RELATED APPLICATIONS

This invention was made with government support under awards U01 ES026140 awarded by the National Institutes of Health, W81XWH-15-1-0217 awarded by the U.S. Army Medical Research and Materiel Command, and W81XWH-19-1-0372 awarded by the U.S. Department of Defense. The government has certain rights in the invention.

SEQUENCE LISTING

This application contains a sequence listing filed in electronic form as an ASCII.txt file entitled "921301-1040 Sequence Listing_ST25" created on Oct. 7, 2020. The content of the sequence listing is incorporated herein in its entirety.

BACKGROUND

Endocrine-disrupting chemicals (EDCs) alter the endocrine system by binding directly to the receptors and modulating downstream signaling pathways. Xenoestrogens are structurally diverse EDCs which affect estrogen receptor (ER) signaling pathways. BP3 (Oxybenzone, or 2-Hydroxy-4-methoxybenzophenone, CAS No. 131-57-7) is a UV-filter used in personal care products, such as sunscreens, cosmetics and lotions, with concentrations up to 0.148% and a maximum allowed concentration of 6% by Food and Drug Administration (FDA) and European commission. BP3 was detected in the urine samples of 96.8% of U.S. population surveyed by the Centers for Disease Control (CDC). Similarly, PP (propyl parahydroxybenzoate, CAS No. 94-13-3) is widely used as an anti-microbial agent in food and personal care products. While the FDA limits PP to 0.1% in food, currently there is no specific limit for preservatives in personal care products. PP is banned as food preservative and maximum permissible levels in personal care products is 0.4% in the EU. PP was detected in the urine samples of >96% of U.S. population surveyed by the CDC.

Estrogenic responses are determined by the action of two distinct estrogen receptor (ER) subtypes, estrogen receptor α (ERα) and estrogen receptor β (ERR). Ligand-activated ER recruits co-activators to estrogen response elements (ERE) in promoters of target genes leading to transcription initiation. In ERα expressing breast cancer cells, proliferation is among the cellular responses. Hence, estrogenic responses to putative xenoestrogens is most often determined by transactivation of ERE-reporters, endogenous gene expression and cell proliferation in ER-expressing MCF-7 and T47D cell lines, where ERα is the dominant subtype.

BP3 is a weak agonist of ER, as determined from transactivation and proliferation assays in MCF-7 at 1 μM. Metabolites of BP3, such as 2,4-diOH-BP and 2,3,4-triOH BP, were shown to form by oxidation in rat and human liver microsomes. 2,4-diOH-BP has been detected in human urine and breast milk and has been shown to have higher ER transactivation potential compared to BP3. Exposure of BP3 during pregnancy and lactation resulted in altered mammary gland ductal architecture that persisted for weeks after exposures ended. Long-term exposure of MCF-7 breast cancer cells to 100 μM BP3 for >20 weeks increased the motility of these cells. This was also observed in estrogen non-responsive cell line MDA-MB-231 suggesting alternate pathways of BP3 actions at this dose.

PP has been shown to be an effective ER-agonist with 1.3-fold induction of gene expression using reporter assays (ERE-CAT reporter) at 10 μM, increased expression of estrogen-responsive gene Trefoil Factor 1 (TFF1, also known as pS2) and increased proliferation of MCF-7 cells at 1 μM. Proliferation induced by PP was inhibited by ER antagonists (Fulvestrant) indicating dependence on ERα. PP also increased cell motility (increased scratch closure) in both short-term (7 days) and long term (20 weeks) treatment in the MCF-7 cell line.

In addition to stimulating cell proliferation and motility, estrogen also induces genotoxicity and DNA damage and is considered a major risk factor in breast cancer etiology. Estrogen has been shown to induce DNA damage, by 1) metabolic activation of estrogen and 2) hormonal carcinogenesis. E2 is metabolized to form catechol estrogens (16α-OHE2 or 2-OHE2 and 4-OHE2), which can be oxidized to form reactive semiquinone (SQ) intermediates and quinone derivatives. Two such compounds, E2-3-4-Q and E2-2-3-Q form stable DNA adduct or depurinating adducts such as 4-OHE2-1N7Gua and 4-OHE2A3de which have been associated with increased breast cancer risk, but micromolar levels of E2-3-4-Q and E2-2-3-Q was required to show DNA adduct formation in vitro. The SQ and quinone derivatives can also generate ROS through redox cycling which can be genotoxic. Similarly, ER-independent DNA damage has been shown in ERα-negative cell lines using the COMET assay, cll mutagenesis assay or LOH. The concentrations of E2 or 4-OHE2 used in these studies were ≥70 nM. However, the median 17β-estradiol level during pregnancy is 74 nM and <2 nM in normal cycling women and the level of circulating 4-OHE2 is 100 fold lower. Therefore, the impact of metabolic activation of estrogen at physiologically relevant concentrations on DNA damage is not yet demonstrated.

Hormonal carcinogenesis has been postulated to act through ER to initiate lesions as well as stimulate progression of tumors. E2 treatment stimulated renal tumors in male Syrian hamsters. Tamoxifen (TAM) reduced tumors, but did not alter levels of DNA-adducts suggesting the primary effect of E2 being mediated by ER. Similarly, blockage of ER activation through selective estrogen receptor modulators such as TAM and raloxifene reduced the incidence of breast cancer by 50-75%. Bilateral oophorectomy and aromatase inhibitors also reduced breast cancer by 75% and 65%, respectively. ER signaling stimulates proliferation which is causally linked to tumorigenesis by increasing the probability of replication errors which are propagated in daughter cells.

Recent studies have shown that ER stimulation leads to transcription-coupled DNA damage suggesting a distinct mechanism. Interaction of ERα with chromatin forms transcriptional co-activator/co-repressor complexes to initiate transcription. The open chromatin in these ERα complexes is susceptible to DNA damage by formation of RNA:DNA triplex structures called R-loops. Therefore, estrogen can stimulate carcinogenesis by initiating direct DNA damage mediated by ERα and proliferation that expands the population of breast cells.

Bioassays of transcriptional activities have been valuable in rapidly assessing the risk posed by xenoestrogens. However, it is unclear if the transcriptional activities of xenoestrogens reflect their potential mutagenic activity mediated by ERα. DNA damage by selective ERα agonists such as Diethylstilbetrol (DES) and 4,4',4"-(4-Propyl-[1H]-pyrazole-1,3,5-triyl)trispheno (PPT) suggest that transcriptional DNA damage needs to be assessed to determine potential breast cancer risk posed by xenoestrogens.

Therefore, improved methods for evaluating the mutagenic potential of environmental chemicals are needed. Also needed are methods of identifying subjects susceptible to these environmental chemicals and/or who are at risk for developing breast cancer from ER-mediated DNA damage.

SUMMARY

Acute exposure to estrogenic chemicals is shown herein to induce genotoxicity, which involves DNA damage mediated by formation of ERα-dependent R-loops at concentrations 10-fold lower than those required for transactivation. This genotoxicity provides a valuable endpoint to consider when evaluating the safety and activity of environmental chemicals and biomarkers for identifying subjects susceptible to genotoxic effects of a xenoestrogen.

Disclosed herein is a method for evaluating the safety and activity of a candidate xenoestrogen by evaluating the ability of the xenoestrogen to cause genotoxicity in ERα-expressing breast cells. In particular, disclosed herein is a method for evaluating the safety of a candidate xenoestrogen that involves contacting an estrogen receptor alpha (ERα)-expressing breast cell with the xenoestrogen, and assaying the cell for genotoxicity, wherein the presence of genotoxicity is an indication that the xenoestrogen is mutagenic.

In some embodiments, the concentration and amount of the xenoestrogen contacted with the breast cell is insufficient to induce ER-dependent transactivation. It is expected that this concentration will be different for each xenoestrogen as well as assay used. For example, in luciferase assay, the LOEC (lowest-observed-effect-concentration) for transcription for BP3 was 5 μM, whereas transactivation was observed at 0.5 μM with PP treatment. Using endogenous gene expression, no significant increase in transcription was observed at 5 μM BP3 and 1 μM PP. Therefore, in some embodiments, the xenoestrogen is at a concentration less than 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10 μM.

In some embodiments, the cell is an ER-positive cell, such as an ER-positive breast cell. For example, in some cases, the breast cell is a human breast cancer cell line. Examples of known breast cancer cell lines include T47D and MCF7 breast cancer cell lines. In other embodiments, the breast cell is normal (non-cancerous) breast epithelial cell that expresses ERα and is therefore estrogen responsive. In some embodiments, the breast cell has been engineered to express physiological levels of ERα.

The near universality of exposure to xenoestrogens implies that a substantial fraction of the population is at risk of the deleterious estrogenic response such as DNA damage. The inducible expression of ERα in normal breast cells provides a tool with which to quantify the variation in sensitivity to these compounds among individuals and to determine if a subset of individuals is preferentially susceptible to the genotoxic activities. Therefore, also disclosed herein is a method for identifying a subject particularly susceptible to the genotoxic effects of xenoestrogens.

Also disclosed herein is a method for identifying a subject susceptible to genotoxic effects of a xenoestrogen. In some embodiments, the method involves exposing the subject to the xenoestrogen. For example, in some embodiments, the subject is treated with the xenoestrogen, a sample is taken and assayed to determine the effects of the xenoestrogen on genotoxicity in the sample, and this information is used to treat the subject. In some of these embodiments, the subject has been diagnosed with a breast cancer, and the sample is a tumor biopsy or excised tumor. Likewise, a high-risk subject can be treated with a xenoestrogen prophylactically, a needle biopsy taken of normal tissue (e.g. breast tissue), and the assay used to determine the effects of the xenoestrogen on genotoxicity in the sample.

Therefore, in some embodiments, the method involves exposing the subject to a xenoestrogen; obtaining or having obtained a tissue sample from the subject; and performing or having performed an assay on the sample to detect genotoxicity, wherein the presence of genotoxicity is an indication that the subject is subject susceptible to genotoxic effects of the xenoestrogen.

In other embodiments, a sample is obtained from the subject and treated in vitro with the xenoestrogen to determine its genotoxic effects. This embodiment can require a larger sample. In some embodiments, the sample involved endometrial tissue. For example, in some embodiments, the method us used to select birth control or hormone replacement therapy for the subject.

Therefore, in some embodiments, the method involves obtaining or having obtained a tissue sample from the subject; exposing the sample with a xenoestrogen; and performing or having performed an assay on the sample to detect genotoxicity, wherein the presence of genotoxicity is an indication that the subject is subject susceptible to genotoxic effects of the xenoestrogen.

Also disclosed herein is a method of treating a subject with a xenoestrogen that involves assaying a sample from the subject and determining that the subject is not susceptible to genotoxic effects of a xenoestrogen, as disclosed herein, and then treating the subject with a xenoestrogen, such as a SERM. SERMs are used for various estrogen-related diseases, including treatment of ovulatory dysfunction in the management of infertility, treatment and prevention of postmenopausal osteoporosis, treatment and reduction in risk of breast cancer and treatment of dyspareunia due to menopause. SERMs are also used in combination with conjugated estrogens indicated for the treatment of estrogen deficiency symptoms, and vasomotor symptoms associated with menopause. SERMs are used dependent on their pattern of action in various tissues. The disclosed method can identify subjects that are not contraindicated for SERM treatment.

Also disclosed herein is a method of treating or preventing an ER-positive cancer in a subject, such as a breast cancer, that involves assaying a sample from the subject and determining that the subject is not susceptible to genotoxic effects of a xenoestrogen, and then treating the subject with a SERM therapy.

Also disclosed herein is a method of treating or preventing an ER-positive cancer in a subject that involves assaying a sample from the subject and determining that the subject is susceptible to genotoxic effects of a xenoestrogen, and then treating the subject with an aromatase inhibitor or selective estrogen receptor degrader (SERD) in an amount effective to reduce the endogenous estrogen levels in the subject.

Genotoxicity can in some embodiments be determined by assaying DNA double strand breaks or structures in RNA and/or DNA that create regions with a higher potential for forming DNA breaks, such as R-loops and G-quadruplex (G4). Genotoxicity can in some embodiments be determined by assaying for the expression or activity of one or more R-loop forming and/or DNA damage repair agents. In some embodiments, DNA damage is detected by detecting $\gamma$H2AX foci in the cell. Other DNA damage or DNA repair markers are known and can be detected. For example, in some embodiments, the COMET assay is used to detect DNA damage. R-loops can be detected using known methods. In some embodiments, the R-loops are detected using a DNA: RNA hybrid-specific antibody, such as the commercially available S9.6 antibody. In some embodiments, the R-loops are detected using a catalytically dead RNAase H. However, this is expected to detect a subset of the R-loop. Examples of R-loop DNA damage repair agents include Top1, BRCA1, BRCA2, SETX, THO/THREX complex, BuGZ, and Bub3. E2 binds estrogen receptors and stimulate conformational changes in DNA (G-quadruplexes) that are adjacent to R-loops in transcribed regions leading to DNA damage that is restricted to specific fragile sites within the genome. In cellulo sensing of G-quadruplex structure can be achieved by either using modified antibodies, G-quadruplex based aptamers, or by using small molecules that selectively light up as response to the binding.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A to 1E show estrogen and xenoestrogens induce estrogen-receptor dependent DNA damage. FIGS. 1A to 10 show quantification of nuclear $\gamma$H2AX intensity in T47D cells treated with 10 or 100 nM 17-$\beta$-estradiol (E2) (FIG. 1A) 1 or 5 $\mu$M benzophenone-3 (BP3) (FIG. 1B), and 1 or 5 $\mu$M propylparaben (PP) (FIG. 10). FIGS. 1D and 1E show quantification of nuclear 53BP1 of treatments in FIG. 1D in T47D (FIG. 1D) and MCF-7 (FIG. 1E). ***p<0.0001, *p<0.01. n=3 biological replicates.

FIG. 2A shows inhibition of TFF1 expression following treatment of 10 nM E2, 5 $\mu$M BP3 and 5 $\mu$M PP when co-treated with Fulvestrant (ICI 182 780, 1 $\mu$M) compared to control E2, BP3 and PP treatments. FIG. 2B shows quantification of nuclear $\gamma$H2AX following co-treatment of fulvestrant (1 $\mu$M) with E2 (10 nM), BP3 (5 $\mu$M) or PP (5 $\mu$M) compared to no fulvestrant treatments. *** indicates comparison between control vs xenoestrogens treatment (p<0.0001). #### indicates comparison between groups i.e. without and with fulvestrant (p<0.001). n=3 biological replicates.

FIG. 3A shows transactivation response (in relative light unit, RLU) of T47D-KBluc cells in response to 10 nM E2, 0.5-100 $\mu$M BP3, and 0.5-100 $\mu$M PP treatment. FIGS. 3B and 3C show induction of endogenous gene expression of AREG (FIG. 3B) and PGR (FIG. 3C) with E2 (10 nM), BP3 (1 or 5 $\mu$M) or PP (1 or 10 $\mu$M) as relative fold expression over control in T47D (left panel) and MCF-7 (right panel). FIG. 3D shows proliferation of 47D cell as percent of alamar blue reduction in response to E2 (0.5 nM), PP (1 or 10 $\mu$M), BP3 (5 $\mu$M) or control. ***p<0.0001. n=3 biological replicates.

FIG. 4A shows quantification of the nuclear S9.6 intensity in T47D. FIG. 4B shows quantification of nuclear S9.6 intensity in MCF-7. *** indicates comparison between control vs xenoestrogens treatment (p<0.0001). #### indicates comparison between groups i.e. without and with fulvestrant (p<0.0001). n=3 biological replicates.

FIG. 5A is a map of pINDUCER-ESR1 construct ESR1 insertion next to doxycycline inducible TRE2 promoter. FIG. 5B is a Western blot of ER$\alpha$ (upper panel) with MCF-7 as positive control (lane 1), 76N:tert parental (lane 2), 76N-Tert without dox (lane 3), 76N-Tert with dox (lane 4) and 76N-Tert with dox and E2 (10 nM) treatment and $\beta$-actin as loading control [lower panel]. FIG. 5C shows quantification of nuclear S9.6 intensity in FIG. 5C. *** indicates comparison between control vs xenoestrogens treatment (p<0.0001). #### indicates comparison between groups i.e. without and with fulvestrant (p<0.0001). n=3 biological replicates. n=2 biological replicates.

FIGS. 6A to 6G show acute exposure of xenoestrogens in mice. FIG. 6A is a schematic of experimental design and exposure period. FIGS. 6B and 6C show quantification of the immunostaining data for S9.6 (FIG. 6B) and $\gamma$H2AX (FIG. 6C). FIGS. 6E and 6F shows expression of AREG (FIG. 6D) and PGR (FIG. 6E) from mouse mammary gland. FIGS. 6F and 6G show Ki67 straining of luminal epithelial cells (FIG. 6F) and percent of Ki67 strained cells per luminal cells counted (FIG. 6G). ***p>0.0001. n=3 biological replicates.

FIG. 7 is a schematic model for ER-dependent DNA damage. E2 or xenoestrogens binding to the ER recruit ER to the estrogen response element (ERE) in the promoter and forms R-loop. Persistence of R-loop in the promoter introduces DNA damage.

FIG. 8 shows quantification of nuclear $\gamma$H2AX intensity in MCF-7 cells following E2 (10-100 nM), BP3(1-30 $\mu$M) or PP (1-30 $\mu$M) treatment. ***p>0.0001.

FIG. 9. Dose-response curve of luciferase reporter assay on T47D-KBluc cells treated with E2 (10 nM), BP3 (1-100 $\mu$M) and PP (1-100 $\mu$M). Dose-response curves were plotted using three-parameter dose response curve. Error bars represent standard deviation (SD).

FIG. 10 shows immunofluorescence with anti-ER$\alpha$ and DAPI showing ER$\alpha$ expression in >90% of the 76NTert-ESR1 cell population.

DETAILED DESCRIPTION

Figure 1A:
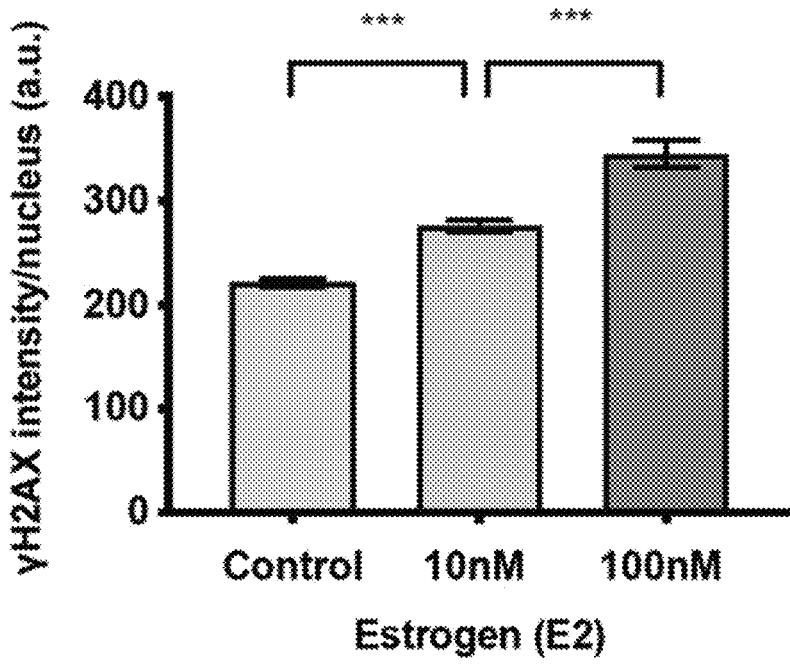

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

An "aromatase inhibitor" is a compound that, when contacted with aromatase, inhibits the formation of the A ring of an androgen substrate to a detectable extent compared to the level of aromatization in the absence of the compound or substance or Means a substance. Any assay that assesses the level of enzyme activity by aromatase can be used to assess whether there is and/or level of inhibition. Aromatase inhibitors include, but are not limited to, steroidal and nonsteroidal inhibitors such as exemestane, anastrozole, letrozole, fadrozole, borozole, and formestane, which are currently known Including any aromatase inhibitor, whether it has been identified or identified in the future.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "sample from a subject" refers to a tissue (e.g., tissue biopsy), organ, cell (including a cell maintained in culture), cell lysate (or lysate fraction), biomolecule derived from a cell or cellular material (e.g. a polypeptide or nucleic acid), or body fluid from a subject. Non-limiting examples of body fluids include blood, urine, plasma, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "xenoestrogens" refers to a type of xenohormone that imitates estrogen. They can be either synthetic or natural chemical compounds. Synthetic xenoestrogens include some widely used industrial compounds, such as PCBs, BPA, and phthalates, which have estrogenic effects on a living organism even though they differ chemically from the estrogenic substances produced internally by the endocrine system of any organism. Natural xenoestrogens include phytoestrogens which are plant-derived xenoestrogens. Because the primary route of exposure to these compounds is by consumption of phytoestrogenic plants, they are sometimes called "dietary estrogens". Mycoestrogens, estrogenic substances from fungi, are another type of xenoestrogen that are also considered mycotoxins.

Biomarkers of Genotoxicity

In some embodiments, DNA damage is detected by detecting γH2AX foci in the cell. Other DNA damage or DNA repair markers are known and can be detected. For example, in some embodiments, the COMET assay is used to detect DNA damage.

Cells utilize diverse mechanisms to regulate the formation of R-loops. These structures can be resolved by RNase H, which specifically degrades the RNA moiety in RNA-DNA hybrids, or by helicases such as Senataxin, which unwind RNA-DNA hybrids. R-loop formation is also suppressed by topoisomerase I, which resolves the negative torsional stress behind RNA polymerase II to prevent annealing of the nascent RNA with the DNA template. Other RNA processing factors also preclude R-loop formation, presumably by binding to RNA as it emerges from RNA polymerase. However when these mechanisms fail, R-loops may persist or accumulate, ultimately leading to DNA breaks and genome instability.

Topoisomerase I (Top1) is a key enzyme in functioning at the interface between DNA replication, transcription and mRNA maturation. Top1 prevents replication fork collapse by suppressing the formation of R-loops in an ASF/SF2-dependent manner.

BRCA1 is recruited to R-loops that form normally over a subset of transcription termination regions. There it mediates the recruitment of a specific, physiological binding partner, senataxin (SETX). Disruption of this complex led to R-loop-driven DNA damage at those loci as reflected by adjacent γ-H2AX accumulation and ssDNA breaks within the untranscribed strand of relevant R-loop structures. Genome-wide analysis revealed widespread BRCA1 binding enrichment at R-loop-rich termination regions (TRs) of actively transcribed genes. Strikingly, within some of these genes in BRCA1 null breast tumors, there are specific insertion/deletion mutations located close to R-loop-mediated BRCA1 binding sites within TRs. Thus, BRCA1/SETX complexes support a DNA repair mechanism that addresses R-loop-based DNA damage at transcriptional pause sites. Aquarius (AQR) is also part of the SETX subfamily of proteins possessing a conserved DEAxQ-like domain with putative RNA/DNA helicase activity.

BRCA2 inactivation by depletion or cancer-causing mutations instigates RNAPII accumulation and R-loop accrual at promoter-proximal pausing (PPP) sites in actively transcribed genes, accompanied by γH2AX formation marking DNA breakage, which is reduced by ERCC4 endonuclease depletion. BRCA2 inactivation decreases RNAPII-associated factor 1 (PAF1) recruitment (which normally promotes RNAPII release) and diminishes H2B Lys120 ubiquitination, impeding nascent RNA synthesis. PAF1 depletion phenocopies, while its overexpression ameliorates, R-loop accumulation after BRCA2 inactivation. Thus, BRCA2 plays a role in the transition from promoter-proximal pausing to productive elongation via augmented PAF1 recruitment to RNAPII is subverted by disease-causing mutations, provoking R-loop-mediated DNA breakage in BRCA2-deficient cells.

THO/TREX is a conserved nuclear complex that functions in mRNP biogenesis and prevents transcription-associated recombination. There is a genome-wide function for THO-Sub2 in transcription elongation and mRNP biogenesis that function to prevent the accumulation of transcription-mediated replication obstacles, including R-loops.

BuGZ and Bub3, two mitotic regulators localized in the interphase nucleus, interact with the splicing machinery and are required for pre-mRNA splicing. Depletion of either BuGZ or Bub3 results in increased formation of R-loops.

E2 binds estrogen receptors and stimulate conformational changes in DNA (G-quadruplexes) that are adjacent to R-loops in transcribed regions leading to DNA damage that is restricted to specific fragile sites within the genome. In cellulo sensing of G-quadruplex structure can be achieved by either using modified antibodies, G-quadruplex based aptamers, or by using small molecules that selectively light up as response to the binding.

The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes. Contacting a sample with the antibody to the molecule of interest or with the molecule that can be bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time long enough for the antibodies to form immune complexes with, i.e., to bind to, any molecules (e.g., antigens) present to which the antibodies can bind. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest (such as the disclosed biomarkers or their antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label. See, for example, U.S. Pat. Nos. 3,817,837; 3,850,752; 3,939,350; 3,996,345; 4,277,437; 4,275,149 and 4,366,241, each of which is incorporated herein by reference in its entirety and specifically for teachings regarding immunodetection methods and labels.

As used herein, a label can include a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

Breast Cancer Treatment

Disclosed herein are methods of selecting a suitable hormone therapy for a subject in need thereof. The method first involves assaying a sample from the subject and determining whether the subject is susceptible to genotoxic effects of a xenoestrogen as described above. If the subject is not susceptible to genotoxic effects of a xenoestrogen, then the subject can be treated with a xenoestrogen, such as a SERM. If, on the other hand, the subject is susceptible to genotoxic effects of a xenoestrogen, then the subject can be treated with an alternative hormone therapy that inhibits estrogen, such as an aromatase inhibitor or SERD.

Selective Estrogen Receptor Modulator

In some embodiments, the disclosed methods involve treating a subject shown not to be susceptible to genotoxic effects of a xenoestrogen with a selective estrogen receptor modulator (SERM). In specific examples, the SERM is one or more of tamoxifen, afimoxifene, raloxifene, bazedoxifene, arzoxifene, desmethylarzoxifene, or a salt or derivative thereof.

Tamoxifen is the trans isomer of 1-(p-beta-dimethyaminoetho-xyphenyl)-1,2-diphenylbut-1-ene, which is disclosed in U.S. Pat. No. 4,536,516, incorporated herein by reference. Tamoxifen, and pharmaceutically acceptable salts and solvates thereof are known to be useful in the treatment of hormone-dependent tumors, such as for the treatment of breast cancer in women, see U.S. Patent Application Publication No. 2003/0158160. Reviews of its clinical usage are available, for example by Purr and Jordan in "Pharmacology and Therapeutics", 1984, Volume 25, pages 127-205. Pharmaceutically acceptable salts of tamoxifen are known. A suitable pharmaceutically acceptable acid-addition salt is, for example, the hydrochloride, hydrobromide, citrate or D-gluconate salt.

Derivatives of tamoxifen are known in the art, see for example, U.S. Patent Application Publication No. 2016/0075726, U.S. Patent Application Publication No. 2006/0105041 and U.S. Patent Application Publication No. 2004/0138314, which are incorporated herein by reference.

U.S. Pat. No. 5,219,549, incorporated herein by reference, discloses tamoxifen derivatives wherein the alkyl chain of the molecule is substituted with fluorine or iodine, such as fluorotamoxifen. The compound 4-hydroxy tamoxifen (afimoxifene), or 144-(2-N-dimethylaminoethoxy)-phenyll-1-(4-hydroxyphenyl)-2-phenylbut-1-(Z)-ene, constitutes an active metabolite of the well characterized anti-estrogen compound, tamoxifen. Both cis and trans isomers exist, either of which, alone or in combination, are useful. Methods for preparing 4-hydroxy tamoxifen are well known.

Aromatase Inhibitor

Aromatase inhibitors may have a non-steroidal or a steroidal chemical structure. According to the present invention, both non-steroidal aromatase inhibitors and steroidal aromatase inhibitors can be used.

By aromatase inhibitors there are to be understood especially those substances that in a determination of the in vitro inhibition of aromatase activity exhibit $IC_{50}$ values of 10-5 M or lower, especially 10-6 M or lower, preferably 10-7 M or lower and most especially 10-8 M or lower.

The in vitro inhibition of aromatase activity can be demonstrated, for example, using the methods described in J. Biol. Chem. 249, 5364 (1974) or in J. Enzyme Inhib. 4, 169 (1990). In addition, $IC_{50}$ values for aromatase inhibition can be obtained, for example, in vitro by a direct product isolation method relating to inhibition of the conversion of 4-$^{14}$C-androstenedione to 4-$^{14}$C-oestrone in human placental microsomes.

By aromatase inhibitors there are to be understood most especially substances for which the minimum effective dose in the case of in vivo aromatase inhibition is 10 mg/kg or less, especially 1 mg/kg or less, preferably 0.1 mg/kg or less and most especially 0.01 mg/kg or less.

The following groups of compounds are listed as examples of aromatase inhibitors. Each individual group forms a group of aromatase inhibitors that can be used successfully in accordance with the present invention.

In some embodiments, the aromatase inhibitor is a compound of formulae I and I* as defined in EP-A-165 904, which is incorporated by reference for these compounds. Example compounds include: 5-(p-cyanophenyl)imidazo[1, 5-a]pyridine, 5-(p-ethoxycarbonylphenyl)imidazo[1,5-a] pyridine, 5-(p-carboxyphenyl)imidazo[1,5-a]pyridine, 5-(p-tert-butylaminocarbonylphenyl)imidazo[1,5-a]pyridine, 5-(p-ethoxycarbonylphenyl)-5,6,7,8-tetrahydroimidazo[1,5-a]pyridine, 5-(p-carboxyphenyl)-5,6,7,8-tetrahydroimidazo[1,5-a]pyridine, 5-(p-carbamoylphenyl)-5,6,7,8-tetrahydroimidazo[1,5-a]pyridine, 5-(p-tolyl)-5,6,7,8-tetrahydroimidazo[1,5-a]pyridine, 5-(p-hydroxymethylphenyl)imidazo[1,5-a]pyridine, 5-(p-cyanophenyl)-7,8-dihydroimidazo[1,5-a]pyridine, 5-(p-bromophenyl)-5,6,7,8-tetrahydroimidazo[1,5-a]pyridine, 5-(p-hydroxymethylphenyl)-5,6,7,8-tetrahydroimidazo[1,5-a]pyridine, 5-(p-formylphenyl)-5,6,7,8-tetrahydroimidazo[1,5-a]pyridine, 5-(p-cyanophenyl)-5-methylthio-5,6,7,8-tetrahydroimidazo[1,5-a]pyridine, 5-(p-cyanophenyl)-5-ethoxycarbonyl-5,6,7,8-tetrahydroimidazo[1,5-a]pyridine, 5-(p-aminophenyl)-5,6,7,8-tetrahydroimidazo[1,5-a]pyridine, 5-(p-formylphenyl)imidazo[1,5-a]pyridine, 5-(p-carbamoylphenyl)imidazo[1,5-a]pyridine, 5H-5-(4-tert-butylaminocarbonylphenyl)-6,7-dihydropyr-rolo[1,2-c]imidazole, 5H-5-(4-cyanophenyl)-6,7-dihydro-pyrrolo[1,2-c]imidazole, 5H-5-(4-cyanophenyl)-6,7,8,9-tet-rahydroimidazo[1,5-a]azepine, 5-(4-cyanophenyl)-6-ethoxycarbonylmethyl-5,6,7,8-tetrahydroimidazo[1,5-a] pyridine, 5-(4-cyanophenyl)-6-carboxymethyl-5,6,7,8-tetrahydroimidazo[1,5-a]pyridine, 5-benzyl-5-(4-cyanophenyl)-5,6,7,8-tetrahydroimidazo[1,5-a]pyridine, 7-(p-cyanophenyl)-5,6,7,8-tetrahydroimidazo[1,5-a]pyri-dine, 7-(p-carbamoylphenyl)-5,6,7,8-tetrahydroimidazo[1, 5-a]pyridine, and 5-(p-cyanophenyl)-5,6,7,8-tetrahydroimi-dazo[1,5-a]pyridine (Fadrozol).

In some embodiments, the aromatase inhibitor is a compound of formula I as defined in EP-A 236 940, which is incorporated by reference for these compounds Example compounds include: 4-[alpha-(4-cyanophenyl)-1-imida-zolylmethyl]-benzonitrile, 4-[alpha-(3-pyridyl)-1-imida-zolylmethyl]-benzonitrile, 4-[alpha-(4-cyanobenzyl)-1-imi-dazolylmethyl]-benzonitrile, 1-(4-cyanophenyl)-1-(1-imidazolyl)-ethylene, 4-[alpha-(4-cyanophenyl)-1-(1,2,4-triazolyl)methyl]-benzonitrile, and 4-[alpha-(4-cyanophenyl)-3-pyridylmethyl]-benzonitrile.

In some embodiments, the aromatase inhibitor is a compound of formula I as defined in EP-A-408 509, which is incorporated by reference for these compounds Example compounds include: 4-(2-tetrazolyl)methyl-benzonitrile, 4-[α-(4-cyanophenyl)-(2-tetrazolyl)methyl]-benzonitrile, 1-cyano-4-(1-tetrazolyl)methyl-naphthalene, 4-[α-(4-cya-nophenyl)-(1-tetrazolyl)methyl]-benzonitrile.

In some embodiments, the aromatase inhibitor is a compound of formula I as defined in European Patent Applica-tion No. 91810110.6, which is incorporated by reference for these compounds Example compounds include: 7-cyano-4-[1-(1,2,4-triazolyl)methyl]-2,3-dimethylbenzofuran, 7-cyano-4-(1-imidazolylmethyl)-2,3-dimethylbenzofuran, 7-carbamoyl-4-(1-imidazolylmethyl)-2,3-dimethylbenzo-furan, and 7-N-(cyclohexylmethyl)carbamoyl-4-(1-imida-zolylmethyl)-2,3-dimethylbenzofuran.

In some embodiments, the aromatase inhibitor is a compounds of formula I as defined in Swiss Patent Application 1339/90-7, which is incorporated by reference for these compounds Example compounds include: 6-cyano-1-(1-imidazolyl)-3,4-dihydronaphthalene, 6-cyano-1-[1-(1,2,4-triazolyl)]-3,4-dihydronaphthalene, 6-chloro-1-(1-imida-zolyl)-3,4-dihydronaphthalene, and 6-bromo-1-(1-imidazolyl)-3,4-dihydronaphthalene.

In some embodiments, the aromatase inhibitor is a compound of formula I as defined in Swiss Patent Application 3014/90-0, which is incorporated by reference for these compounds Example compounds include: 4-[α-(4-cyano-phenyl)-α-hydroxy-5-isothiazolylmethyl]-benzonitrile, 4-[α-(4-cyanophenyl)-5-isothiazolylmethyl]-benzonitrile, 4-[α-(4-cyanophenyl)-5-thiazolylmethyl]-benzonitrile, 1-(4-cyanophenyl)-1-(5-tiazolyl)-ethylene, 6-cyano-1-(S-isothiazolyl)-3,4-dihydronaphthalene, and 6-cyano-1-(5-thi-azolyl)-3,4-dihydronaphthalene.

In some embodiments, the aromatase inhibitor is a compound of formula VI as defined in Swiss Patent Application 3014/90-0, which is incorporated by reference for these compounds Example compounds include: bis(4,4'-brom-ophenyl)-(5-isothiazolyl)methanol, bis(4,4'-bromophenyl)-(5-isothiazolyl)methane, bis(4,4'-bromophenyl)-(5-thiaz-olyl)methanol, and bis(4,4'-bromophenyl)-(5-thiazolyl) methane.

In some embodiments, the aromatase inhibitor is a compound of formula I as defined in Swiss Patent Application 3923/90-4, which is incorporated by reference for these compounds Example compounds include: 4-[α-4-cyanophe-nyl)-α-fluoro-1-(1,2,4-triazolyl)methyl]-benzonitrile, 4-[α-(4-cyanophenyl)-α-fluoro-(2-tetrazolyl)methyl]-benzoni-trile, 4-[α-(4-cyanophenyl)-α-fluoro-(1-tetrazolyl)methyl]-benzonitrile, 4-[α-(4-cyanophenyl)-α-fluoro-(1-imidazolyl) methyl]-benzonitrile, 1-methyl-6-[α-(4-chlorophenyl)-α-fluoro-1-(1,2,4-triazolyl)methyl]-benzotriazole, 4-[α-(4-cyanophenyl)-α-fluoro-1-(1,2,3-triazolyl)methyl]-benzonitrile, 7-cyano-4-[α-(4-cyanophenyl)-α-fluoro-1-(1, 2,4-triazolyl)methyl]-2,3-dimethylbenzo[b]furan, 4-[α-(4-bromophenyl)-α-fluoro-1-(1,2,4-triazolyl)methyl]-benzonitrile, 4-[α-(4-cyanophenyl)-α-fluoro-(5-pyrimidyl) methyl]-benzonitrile, 4-[α-(4-bromophenyl)-α-fluoro-(5-pyrimidyl)methyl]-benzonitrile, 4-[α-(4-cyanophenyl)-α-fluoro-(3-pyridyl)methyl]-benzonitrile, 7-bromo4-[α-(4-cyanophenyl)-α-fluoro-(1-imidazolyl)methyl]-2,3-dimethylbenzo[b]furan, 7-bromo-4-[α-(4-cyanophenyl)-α-fluoro-1-(1,2,4-triazolyl)methyl]-2,3-dimethylbenzo[b] furan, 4-[α-(4-cyanophenyl)-α-fluoro-(5-pyrimidyl) methyl]-benzonitrile, 4-[α-(4-bromophenyl)-α-fluoro-(5-pyrimidyl)methyl]-benzonitrile, 4-[α-(4-cyanophenyl)-1-(1, 2,3-triazolyl)methyl]-benzonitrile, 2,3-dimethyl4-[α-(4-cyanophenyl)-1-(1,2,4-triazolyl)methyl]-7-cyano-benzo[b] furan, 4-[α-(4-cyanophenyl)-(5-pyrimidyl)methyl]-benzonitrile, 4-[α-(4-bromophenyl)-(5-pyrimidyl)methyl]-benzonitrile, 2,3-dimethyl4-[α-(4-cyanophenyl)-(1-imidazolyl)methyl]-7-bromo-benzo[b]furan, and 2,3-dimethyl-4-[α-(4-cyanophenyl)-1-(1,2,4-triazolyl)methyl]-7-bromo-benzo-[b]furan.

In some embodiments, the aromatase inhibitor is a compound of formula I as defined in EP-A-114 033, which is incorporated by reference for these compounds. Example compounds include: 1-(4-aminophenyl)-3-methyl-3-azabi-cyclo[3.1.0]hexane-2,4-dione, 1-(4-aminophenyl)-3-n-pro-pyl-3-azabicyclo[3.1.0]hexane-2,4-dione, 1-(4-aminophe-nyl)-3-isobutyl-3-azabicyclo[3.1.0]hexane-2,4-dione, 1-(4-aminophenyl)-3-n-heptyl-3-azabicyclo[3.1.0]hexane-2,4-dione, and 1-(4-aminophenyl)-3-cyclohexylmethyl-3-azabicyclo[3.1.0]hexane-2,4-dione.

In some embodiments, the aromatase inhibitor is a compound of formula I as defined in EP-A-166 692, which is incorporated by reference for these compounds Example compounds include: 1-(4-aminophenyl)-3-n-propyl-3-azabi-cyclo[3.1.1]heptane-2,4-dione, 1-(4-aminophenyl)-3-methyl-3-azabicyclo[3.1.1]heptane-2,4-dione, 1-(4-amino-phenyl)-3-n-decyl-3-azabicyclo[3.1.1]heptane-2,4-dione, 1-(4-aminophenyl)-3-cyclohexyl-3-azabicyclo[3.1.1]hep-tane-2,4-dione, and 1-(4-aminophenyl)-3-cyclohexylm-ethyl-3-azabicyclo[3.1.1]heptane-2,4-dione.

In some embodiments, the aromatase inhibitor is a compound of formula I as defined in EP-A-356 673, which is incorporated by reference for these compounds Example compounds include: 5-(2'-naphthyl)-5,6,7,8-tetrahydroimi-dazo[1,5-a]pyridine, and 5-(4'-pyridyl)-5,6,7,8-tetrahydro-imidazo[1,5-a]pyridine.

In some embodiments, the aromatase inhibitor is a compound of formula I or Ia as defined in EP-A-337 929, which is incorporated by reference for these compounds Example compounds include: 4-(2,4-dichlorobenzyloxy)-3-[1-(1-imi-dazolyl)-butyl]-benzonitrile, (4-(4-bromobenzyloxy)-3-[1-(1-imidazolyl)-butyl]-phenyl pentyl ketone, 4-(4-bromoben-zyloxy)-3-[1-(1-imidazolyl)-butyl]-benzanilide, 4-(4-bromobenzyloxy)-3-[1-(1-imidazolyl)-butyl]-benzoic acid, 3-(2,4-dichlorobenzyloxy)-4-[1-(1-imidazolyl)-butyl]-ben-zonitrile, 3-(2,4-dichlorobenzyloxy)-4-[1-(1-imidazolyl)-butyl]-benzoic acid methyl ester, 3-(2,4-dichlorobenzy-loxy)-4-[1-(1-imidazolyl)-butyl]-benzoic acid, 3-(3- bromobenzyloxy)-4-[1-(1-imidazolyl)-butyl]-benzonitrile, 4-(3-bromobenzyloxy)-3-[1-(1-imidazolyl)-butyl]-benzonitrile, 3-(4-bromobenzyloxy)-4-[1-(1-imidazolyl)-butyl]-benzoic acid, 3-(4-bromobenzyloxy)-4-[1-(1-imidazolyl)-butyl]-benzanilide, 3-(4-bromobenzyloxy)-4-[1-(1-imidazolyl)-butyl]-phenyl pentyl ketone, 4-(4-bromobenzyloxy)-3-[1-(1-imidazolyl)-butyl]-benzonitrile, 3-(4-bromobenzyloxy)-4-[1-(1-imidazolyl)-butyl]-benzonitrile, 4-nitro-2-[1-(1-imidazolyl)-butyl]-phenyl-(2,4-dichlorobenzyl)ether, 4-amino-2-[1-(1-imidazolyl)-butyl]-phenyl-(2,4-dichlorobenzyl)ether, and (2,4-dichlorobenzyl)-[2-(1-imidazolyl-methyl)-4-nitrophenyl]ether.

In some embodiments, the aromatase inhibitor is a compound of formula I as defined in EP-A-337 928, which is incorporated by reference for these compounds Example compounds include: 5-[1-(1-imidazolyl)-butyl]-thiophene-2-carbonitrile, 2-[1-(1-imidazolyl)-butyl]-thiophene-4-carbonitrile, 2-[1-(1-imidazolyl)-butyl]-4-bromo-thiophene, 2-[1-(1-imidazolyl)-butyl]-5-bromo-thiophene, 5-[1-(1-imidazolyl)-butyl]-2-thienyl pentyl ketone, 5-[1-(1-imidazolyl)-butyl]-2-thienyl ethyl ketone, 5-(4-chlorobenzyloxy)-4-[1-(1-imidazolyl)-pentyl]-pyridine-2-carbonitrile, 3-(4-chlorobenzyloxy)-4-[1-(1-imidazolyl)-pentyl]-pyridine-2-carbonitrile, 3-(4-chlorobenzyloxy)-4-[1-(1-imidazolyl)-pentyl]-pyridine-N-oxide, and 3-(4-chlorobenzyloxy)-4-[1-(1-imidazolyl)-pentyl]-pyridine.

In some embodiments, the aromatase inhibitor is a compound of formula I as defined in EP-A-340 153, which is incorporated by reference for these compounds Example compounds include: 4-(1-(1-imidazolyl)-butyl)-benzoic acid methyl ester, 4-(1-(1-imidazolyl)-butyl)-benzoic acid butyl ester, 4-(1-(1-imidazolyl)-butyl)-phenyl-acetonitrile, 4-(1-(1-imidazolyl)-butyl)-benzaldehyde, 4-(1-(1-imidazolyl)-butyl)-benzyl alcohol, 4-[1-(1-imidazolyl)-butyl]-phenyl}-2-propyl ketone, 4-[1-(1-imidazolyl)-butyl]-phenyl propyl ketone, 4-[1-(1-imidazolyl)-butyl]-phenyl butyl ketone, 4-[1-(1-imidazolyl)-butyl]-phenyl pentyl ketone, and 4-[1-(1-imidazolyl)-butyl]-phenyl hexyl ketone.

In some embodiments, the aromatase inhibitor is a compound of formula I as defined in DE-A-4 014 006, which is incorporated by reference for these compounds Example compounds include: 5-[1-(1-imidazolyl)-butyl]-1-indanone, 7-[1-(1-imidazolyl)-butyl]-1-indanone, 6-[1-(1-imidazolyl)-butyl]-1-indanone, 6-(1-imidazolyl)-6,7,8,9-tetrahydro-1H-benz[e]inden-3(2H)-one, 2-[1-(1-imidazolyl)-butyl]-4-dihydro-6-oxo-cyclopenta[b]-thiophene, 6-[1-(1-imidazolyl)-butyl]-3,4-dihydro-2H-naphthalen-1-one, 2-[1-(1-imidazolyl)-butyl]-6,7-dihydro-5H-benzo[b]thiophen-4-one, 6-[1-(1-imidazolyl)-butyl]-2H-benzo[b]furan-3-one, 5-[cyclohexyl-(1-imidazolyl)-methyl]-1-indanone, 2-[1-(1-imidazolyl)-butyl]-4,5-dihydro-6H-benzo[b]thiophen-7-one, 5-[1-(1-imidazolyl)-1-propyl-butyl]-1-indanone, 2-[1-(1-imidazolyl)-butyl]-4,5-dihydro-6H-benzo[b]thiophen-7-one, 2-[1-(1-imidazolyl)-butyl]-4,5-dihydro-6-oxo-cyclopenta[b]-thiophene, 5-(1-imidazolylmethyl)-1-indanone, and 5-[1-(1,2,4-triazolyl)-methyl]-1-indanone.

In some embodiments, the aromatase inhibitor is a compound of formula I as disclosed in DE-A-3 926 365, which is incorporated by reference for these compounds Example compounds include: 4-[1-cyclohexylidene-1-(imidazolyl)-methyl]-benzonitrile, 4-[1-cyclopentylidene-1-(imidazolyl)-methyl]-benzonitrile, 4-[1-cycloheptylidene-1-(imidazolyl)-methyl]-benzonitrile, 4-[2-adamantylidene-1-(imidazolyl)-methyl]-benzonitrile, 4-[1-cyclohexylidene-1-(1,2,4-triazolyl)-methyl]-benzonitrile, 4-[1-cyclopentylidene-1-(1, 2,4-triazolyl)-methyl]-benzonitrile, 4-[1-cycloheptylidene-1-(1,2,4-triazolyl)-methyl]-benzonitrile, 4-[2- adamantylidene-1-(1,2,4-triazolyl)-methyl]-benzonitrile, 4-[1-cyclohexylidene-1-(1,2,3-triazolyl)-methyl]-benzonitrile, 4-[1-cyclopentylidene-1-(1,2,3-triazolyl)-methyl]-benzonitrile, and 5-[cyclohexylidene-1-imidazolylmethyl]-thiophene-2-carbonitrile.

In some embodiments, the aromatase inhibitor is a compound of formula I as defined in DE-A-3 740 125, which is incorporated by reference for these compounds An example compound includes 2,2-bis(4-chlorophenyl)-2-(1H-imidazol-1-yl)-1-(4-chlorobenzoyl-amino)ethane.

In some embodiments, the aromatase inhibitor is a compound of formula I as defined in EP-A-293 978, which is incorporated by reference for these compounds Example compounds include: 6-[(1H-imidazol-1-yl)-phenylmethyl]-1-methyl-1H-benzotriazole, and 6-[(4-chlorophenyl)(1H-1,2,4-triazol-1-yl)methyl]-1-methyl-1H-benzotriazole.

In some embodiments, the aromatase inhibitor is a compound of formula II as defined in EP-A-250 198, such as 2-(4-chlorophenyl)-1,1-di(1,2,4-triazol-1-ylmethyl)ethanol, 2-(4-fluorophenyl)-1,1-di(1,2,4-triazol-1-ylmethyl)ethanol, 2-(2-fluoro-4-trifluoromethylphenyl)-1,1-di(1,2,4-triazol-1-ylmethyl)ethanol, 2-(2,4-dichlorophenyl)-1,1-di(1,2,4-triazol-1-ylmethyl)ethanol, 2-(4-chlorophenyl)-1,1-di(1,2,4-triazol-1-ylmethyl)-ethanol, and 2-4-fluorophenyl)-1,1-di(1, 2,4-triazol-1-yl-methyl)ethanol.

In some embodiments, the aromatase inhibitor is a compound of formula I as defined in EP-A-281 283, such as (1R*2R*)-6-fluoro-2-(4-fluorophenyl)-1,2,3,4-tetrahydro-1-(1H-1,2,4-triazol-1-yl-methyl)naphthalene, (1R*,2R*)-6-fluoro-2-(4-fluorophenyl)-1,2,3,4-tetrahydro-1-(1H-imidazolylmethyl)-naphthalene, (1R*,2R*)- and (1R*,2S*)-2-(4-fluorophenyl)-1,2,3,4-tetrahydro-1-(1H-1,2,4-triazol-1-ylmethyl)naphthalene-6-carbonitrile, (1R*,2R*)- and (1R*, 2S*)-2-(4-fluorophenyl)-1,2,3,4-tetrahydro-1-(1H-imidazolylmethyl)naphthalene-6-carbonitrile, (1R*,2R*)- and (1R*,2S*)-1,2,3,4-tetrahydro-1-(1H-1,2,4-triazol-1-yl-methyl)-naphthalene-2,6-dicarbonitrile, (1R*,2R*)- and (1R*,2S*)-1,2,3,4-tetrahydro-1-(1H-imidazol-1-ylmethyl) naphthalene-2,6-dicarbonitrile, and (1R*,2S*)-2-(4-fluorophenyl)-1,2,3,4-tetrahydro-1-(5-methyl-1H-imidazolyl-methyl)naphthalene-6-carbonitrile.

In some embodiments, the aromatase inhibitor is a compound of formula I as defined in EP-A-296 749, such as 2,2'-[5-(1H-1,2,4-triazol-1-ylmethyl)-1,3-phenylene]di(2-methylpropionitrile), 2,2'[5-(imidazol-1-ylmethyl)-1,3-phenylene]di(2 methylpropionitrile), 2-[3-(1-hydroxy-1-methylethyl)-5-(5H-1,2,4-triazol-1-ylmethyl)phenyl]-2-methylpropionitrile, 2,2'-[5-dideuterio(1H-1,2,4-triazol-1-yl)methyl-1,3-phenylene]di(2-trideuteriomethyl-3,3,3-trideuteriopropiononitrile), and 2,2'-[5-dideuterio(1H-1,2,4-triazol-1-yl)methyl-3-phenylene]di(2methylpropiononitile).

The compounds of formula I as defined in EP-A-299 683, especially (Z)-α-(1,2,4-triazol-1-ylmethyl)stilbene-4,4'-dicarbonitrile, (Z)-4'-chloro-α-(1,2,4-triazol-1-ylmethyl)stilbene-4-carbonitrile, (Z)-α-(1,2,4-triazol-1-ylmethyl)-4'-(trifluoromethyl)stilbene-4-carbonitrile, (E)-.beta.-fluoro-α-(1, 2,4-triazol-1-ylmethyl)stilbene-4,4'-dicarbonitrile, (Z)-4'-fluoro-α-(imidazol-1-ylmethyl)stilbene-4-carbonitrile, (Z)-2',4'-dichloro-α-(imidazol-1-ylmethyl)stilbene-4-carbonitrile, (Z)-4'-chloro-α-(imidazol-1-ylmethyl)stilbene-4-carbonitrile, (Z)-α-(imidazol-1-ylmethyl)stilbene-4, 4'dicarbonitrile, (Z)-α-(5-methylimidazol-1-ylmethyl) stilbene-4,4'-dicarbonitrile, and (Z)-2-[2-(4-cyanophenyl)-3-(1,2,4-triazol-1-yl)propenyl]pyridine-5-carbonitrile.

In some embodiments, the aromatase inhibitor is a compound of formula I as defined in EP-A-299 684, such as 2-(4-chlorobenzyl)-2-fluoro-1,3-di(2,4-triazol-1-yl)propane, 2-fluoro-2-(2-fluoro-4-chlorobenzyl)-1,3-di(1,2,4-tri-azol-1-yl)propane, 2-fluoro-2-(2-fluoro-4-trifluoromethyl-benzyl)-1,3-di(1,2,4-triazol-1-yl)propane, 3-(4-chlorophenyl)- -(1,2,4-triazol-1-yl)-2-(1,2,4-triazol-1-ylmethyl)butan-2-ol, 2-(4-chloro-α-fluorobenzyl)-1,3-di(1, 2,4-triazol-1-yl)propan-2-ol, 2-(4-chlorobenzyl)-1,3-bis(1, 2,4-triazol-1-yl)propane, 4-[2-(4-chlorophenyl)-1,3-di(1,2, 4-triazol-1-ylmethyl)ethoxymethyl]-benzonitrile, 1-(4-fluorobenzyl)-2-(2fluoro-4-trifluoromethylphenyl)-1,3-di(1, 2,4-triazol-1-yl)-propan-2-ol, 2-(4-chlorophenyl)-1-(4-fluorophenoxy)-1,3-di(1,2,4-triazol-1-yl)propan-2-ol, 1-(4-cyanobenzyl)-2-(2,4-difluorophenyl)-1,3di(1,2,4-triazol-1-yl)propan-2-ol, and 2-(4-chlorophenyl)-1-phenyl-1,3-di(1,2, 4-triazol-1-yl)propan-2-ol.

In some embodiments, the aromatase inhibitor is a compound of EP-A-316 097, such as 1,1-dimethyl-8-(1H-1,2,4-triazol-1-ylmethyl)-2(1H)-naphtho[2,1-b]furanone, 1,2-di-hydro1,1-dimethyl-2-oxo-8-(1H-1,2,4-triazol-1-ylmethyl) naphtho[2,1-b]-furan-7-carbonitrile, 1,2-dihydro-1,1-dimethyl-2-oxo-8-(1H-1,2,4-triazol-1-ylmethyl)naphtho[2, 1-b]-furan-7-carboxamide, and 1,2-dihydro-1,1-dimethyl-2-oxo-8-[di(1H-1,2,4-triazol-1-yl)methyl]naphtho[2,1-b]-furan-7-carbonitrile.

In some embodiments, the aromatase inhibitor is a compound of EP-A-354 689, such as 4-[2-(4-cyanophenyl)-3-(1,2,4-triazol-1-yl)propyl]benzonitrile, 4-[1-(4-chloroben-zyl)-2-(1,2,4-triazol-1-yl)ethyl]benzonitrile, 4-[2-(1,2,4-triazol-1-yl)-1-(4-trifluoromethyl]benzyl)ethyl]benzonitrile, and 4-[2-(1,2,4-triazol-1-yl)-1-(4-[trifluoromethoxy]benzyl) ethyl]benzonitrile.

In some embodiments, the aromatase inhibitor is a compound of EP-A-354 683, such as 6-[2-(4-cyanophenyl)-3-(1,2,4-triazol-1-yl)-propyl]nicotinonitrile or 4-[1-(1,2,4-tri-azol-1-yl-methyl)-2-(5-[trifluoromethyl]pyrid-2-yl)ethyl] benzonitrile.

In some embodiments, the aromatase inhibitor is a ste-roidal aromatase inhibitor, such as the compound of formula I as defined in EP-A-181 287, which is incorporated by reference for these compounds. An example compound 4-hydroxy-4-androstene-3,17-dione.

The dose of the aromatase inhibitor will be tailored to the particular patient (as well the dose of estrogen). The patient can be started on a regimen (for example the bio-equivalent of at or about 0.25 mg to 10 mg Anastrozle daily and the bio-equivalent of at or about 0.125 to 1.0 mg or about 0.125 to 0.5 mg per day of estradiol), and the doses adjusted until the patient reports an improvement in libido and/or in mood.

The dose of aromatase inhibitor will preferably be such that it results in an increase of androgen serum levels over the basal level for the patient in question. In a male, it is preferred that androgen levels reach at least at or about 350 to 1000 ng/dL, more preferably at or about 400 to 700 ng/dL.

Letrozole and anastrazole are preferred aromatase inhibi-tors. Other suitable aromatase inhibitors include but are not limited to exemestane, vorozole, fadrozole, pentrozole, formestane, atamestane and testolactone. If anastrozole (Arimidex) is used, a preferred dose is selected from at or about 0.25 to at or about 10 mg. If another aromatase inhibitor is used, the preferred dose may be defined as a bio-equivalent dose to the dose range for anastrozole. For example, the preferred dose for letrozole is also between at or about 0.25 to at or about 10 mg per day. The preferred dose for exemestane is between at or about 5 mg to at or about 50 mg per day. The preferred dose for testolactone is between at or about 100 mg to at or about 400 mg daily.

Selective Estrogen Receptor Degrader

In some embodiments, the disclosed methods involve treating a subject shown to be susceptible to genotoxic effects of a xenoestrogen with a selective estrogen receptor degrader (SERD), such as those described in, e.g., WO 2012/037411, WO 2012/037410, WO 2011/159769, WO 2011/156518 and US 2012/0071535, which are incorporated by reference for these compounds. In some cases, the SERD is a fulvestrant formulation described in US 2019/0134059, which is incorporated by reference for these compounds.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Benzophenone-3 and Propylparaben Induce Estrogen Receptor-Dependent R-Loop and DNA Damage in Breast Epithelial Cells Methods Cell Culture: T47D (ATCC #HTB-1330), T47DKBluc (ATCC #CRL-2865) and MCF-7(ATCC #HTB 22) cells were passaged in phenol-red free (PRF) DMEM-F12 media (Sigma #D6434) or MEM 1× (Gibco #51200-038) with 10% heat inactivated FBS (Omega Scientific #FB-02) and 10 μg/ml insulin (Sigma #9278), 2 mM L-glutamine (Hyclone #SH30034.01), gentamycin 15 μg/ml (Gibco #15750-060) and 1× antibiotics/antimycotics (AB/AM, Gibco #15240-062) and incubated at 37° C. with 5% $CO_2$. Cells were grown in clearing media with charcoal-stripped serum (CSS) (MEM 1× with 10% charcoal-dextran treated FBS (Omega Scientific #FB-04), 10 μg/ml insulin and 2 mM L-glutamine) for 24-72 h before being plated for experiments.

Generation of 76N-Tert-ESR1 cells: The 76N-Tert cell line, a human mammary epithelial cell line immortalized with expression of human telomerase reverse transcriptase (TERT) was provided (35). These cells were grown in F-media (250 mL DMEM (-pyruvate) (Gibco #11965-092), 250 mL Ham's F12 (Gibco #11765-054), 5% FBS, 250 ng/mL hydrocortisone (Sigma #H4001), 10 ng/mL human epidermal growth factor (Tonbo Biosciences #21-8356-U100), 8.6 ng/mL cholera toxin *vibrio* (Millipore Sigma #227035), 1 μg/mL human insulin solution, and 1× antibi-otic-antimycotic and passaged every 2-3 days.

An inducible ERα (ESR1) construct was generated using the pINDUCER14 backbone ((36). Briefly, a FLAG tag sequence was amplified from pFLAG-CMV-2 and ligated using Age/site in pINDUCER14. ESR1 was amplified from a plasmid expressing ESR1, and inserted between EcoRI and M/u/sites (Table 1). Two linker sequences between FLAG and ESR1 were added to keep ESR1 sequence in-frame. Sequencing of this final pINDUCER14-FLAG-ESR1 confirmed that all inserts were in the correct orienta-tion relative to the vector backbone, both FLAG and ESR1 were in frame, and the ESR1 sequence was identical to the *Homo sapiens* ESR1 gene. This final construct is referred to as pIND-ESR1 and expresses a constitutive GFP reporter and ERα with N-terminal FLAG tag. 293T cells were transfected with 3.5 μg pIND-ESR1, 3 μg psPAX2 (gag, pol, and rev packaging vector), and 2 μg pMD2.G (vsv-g pack-aging vector) in antibiotic free media using Lipofectamine 2000 (Thermo Fisher Scientific). Media was refreshed after 24 hours and viral media was collected at 48 and 54 hours post initial transfection. Viral media from transfected 293T was filtered using a 0.45 μM filter (Corning #431220) and added to 76N-Tert cells twice, 6 hours apart, in a 1:1 ratio with F-media. After 24 hours, viral media was removed and replaced with F-media. Following cell expansion, the cells were pooled and resuspended in 1% FBS/PBS. Selection of the stably transduced cells was performed by FACS for GFP+ cells using FACSAria II (Becton-Dickinson). 76N-Tert uninfected cells were used as a control to set the background fluorescence. Approximately 5% cells were GFP+ suggesting pINDUCER14-FLAG-ESR1 expression. The GFP+ cells were collected to 90% purity. These cells were expanded and referred to as 76N-Tert-ESR1.

TABLE 1

| Sequences of primers | |
| --- | --- |
| Target | Sequence (5' to 3') |
| FLAG | F: GATACCGGTACCATGGACTACAAAGACGATGA CGAC (SEQ ID NO: 1) R: TCGACCGGTACGCGTGCGATCGCTGAATTCGC GGCAAG (SEQ ID NO: 2) |
| ESR1 | F: GCAGAAATGACCATGACCCTCCACACCAAAGC (SEQ ID NO: 3) R: TAAACGCGTTCAGACCGTGGCAGGGAAACCCT (SEQ ID NO: 4) |
| Linkers | Linker A: AATTGCGCGATCGCGG (SEQ ID NO: 5) Linker B: AATTCCGCGATCGCGC (SEQ ID NO: 6) |
| Sequencing Primers pIND-ESR1 | F: CGGTGGGAGGCCTATATAAG (SEQ ID NO: 7) M: GCTACCATTATGGAGTCTGG (SEQ ID NO: 8) R: ACTTATATACGGTTCTCCCC (SEQ ID NO: 9) |
| qPCR Primers TFF1 (human) | F: CCCCTGGTGCTTCTATCCTAA (SEQ ID NO: 10) R: GATCCCTGCAGAAGTGTCTAAAA (SEQ ID NO: 11) |
| qPCR Primers AREG (human) | F: CGGAGAATGCAAATATATAGAGCAC (SEQ ID NO: 12) R: CACCGAAATATTCTTGCTGACA (SEQ ID NO: 13) |
| qPCR Primers PGR (human) | F: TTTAAGAGGGCAATGGAAGG (SEQ ID NO: 14) R: CGGATTTTATCAACGATGCAG (SEQ ID NO: 15) |
| qPCR Primers Pgr (mouse) | F: GACCACATCAGGCTCAATGCT (SEQ ID NO: 16) R: GGTGGGCCTTCCTAACGAG (SEQ ID NO: 17) |
| qPCR Primers Areg (mouse) | F: GTCACTATCTTTGTCTCTGCCA (SEQ ID NO: 18) R: CCTCCTTCTTTCTTCTGTTTCTCC (SEQ ID NO: 19) |

Luciferase Reporter Assay: T47DKBluc cells grown in clearing media for 72 h and plated in a 24 well plate at $10 \times 10^5$ cells/well density. After 24 h cells were treated with 10 nM E2 (17β-estradiol, Sigma #E2758), 10 nM fulvestrant (F, ICI 182, 780, Tocris #1047) or 0.5 to 50 μM BP3 (Sigma #H36206) or 0.5 to 50 μM PP (Sigma #P53357). Stock solutions were prepared in DMSO (Sigma #D8418), then diluted to working concentrations in media. Luciferase assays were performed using the Promega Dual-Luciferase Reporter Assay (Promega #E1910). Cells were lysed in 1× Passive Lysis Buffer after treatment for 24 hours and then stored at −20° C. Luciferase activity was determined in lysates by using the Polar Star OPTIMA plate reader (BMG Labtech) and expressed in relative light units (RLU). Treatments were compared to 10 nM E2 included on the plate and relative transactivation activity (RTA) is defined as percent transactivation compared to 10 nM E2.

RT-qPCR: RNA from T47D cells, MCF-7 Cells or flash-frozen 4th mammary gland was isolated with TRIzol (Thermofisher Scientific #15596018) and Direct-zol RNA Mini-Prep Plus (Zymo Research #R2072). cDNA was prepared with Protoscript II First Strand cDNA Synthesis Kit (New England Biolabs #E6560S) and qPCR for TFF1, progesterone receptor (PGR) and Amphiregulin (AREG) was performed on CFX96 Real-Time System thermocycler (Bio-Rad) using primers in Table 1.

Cell Proliferation Assay: T47D cells grown in clearing media for 72 h was plated as 100 μl of cells suspension having 5000 or 10000 cells per well on five 96 well plates (one for each day). The 96 well plate had 12 cell-free wells for a blank and 7 wells per treatment on each plate. After 24 h, 100 μl of E2, BP3 or PP containing media was added to appropriate wells on each plate to reach the desired final concentration in each well. All plates were maintained in a 37° C., 5% $CO_2$ incubator until media was exchanged, on one plate per day, for 10% Alamar Blue in plating media. Plates were read at the same time each day at 4 hr and 8 hr after media exchange on a BioTek Synergy 2 plate reader (Winooski, VT) at 570 nm and 600 nm. Percent alamar blue reduction was calculated as per the following equation on the AlamarBlue protocol:

$$\text{Percent reduced} = \frac{(117216 \times \text{test well } A_{570}) - (80586 \times \text{test well } A_{600})}{(155677 \times \text{mean (negative control wells } A_{600})) - (14652 \times \text{mean (negative control wells } A_{570}))} \times 100$$

Immunostaining: Cells were grown in clearing media for 48 h and plated on 20 mm coverslip in 12 well plates with a density of $2 \times 10^5$ cells/well. After 24 h of growth, cells were treated with 10 nM E2, 1 or 5 μM BP3, and 1 or 5 μM PP with or without 1 μM fulvestrant. γH2AX/ERα: Cells were fixed in ice-cold methanol (100%) for 10 mins and quenched with 0.1 M Glycine for 15 mins. Cells were washed with 1×PBS, blocked in 2% BSA/PBS with 0.1% Triton-X 100 for 1 hr at room temperature (RT), incubated overnight with γH2AX antibody (Cell Signaling #9718 S) or ERα antibody (Santa Cruz Biotechnology #sc-8002) at 4° C. and 1 hour with secondary antibody. S9.6: Cells were fixed in ice-cold 100% methanol for 10 min at −20° C., permeabilized in 100% acetone for 1 min at RT, blocked for 30 min in saline sodium citrate pH 7 (SSC, 4×), 3% BSA, 0.1% Triton-X and incubated with S9.6 (Kerafast #ENH001) 2 hr at RT followed by 1 h with secondary antibody. If indicated, slides were treated with RNase H (NEB #M0297L) for 4 hr at 37° C. prior to incubation with primary antibody. Stained cells were mounted with Vectashield mounting medium containing DAPI (Vector Laboratories #H-1200). Slides were imaged at 60× (immersion oil) with Nikon A1 Spectral Confocal microscope. Analysis of γH2AX and S9.6 intensity per nucleus or foci per nucleus was calculated using Nikon analysis software, where DAPI was used as a mask for the nucleus.

Western blot: Whole cell extracts were lysed with ice cold RIPA lysis buffer (50 mM Tris-HCl, pH 8.0; 150 mM NaCl; 1 mM EDTA; 1% Triton X-100; 1% Sodium deoxycolate; 0.1% SDS; 1% protease inhibitors (Sigma-Aldrich #P8340), 1% phosphatase inhibitor #2 (Sigma-Aldrich #P5726), and 1% phosphatase inhibitor #3 (Sigma-Aldrich #P0044). Homogenate was centrifuged at 13,000 rpm for 15 minutes at 4° C. to remove cellular debris. Protein quantification was performed using BCA protein assay (Thermo Scientific #23225). Equal amounts of protein (28 μg) were separated by SDS-PAGE on 10% acrylamide under denaturing conditions and then blotted onto PVDF membrane (Millipore #IPVH00010). Non-specific binding was blocked with 5% non-fat dry milk in TBST (Tris-buffered saline and Tween 20 containing 10 mM Tris-HCl, pH 7.5; 150 mM NaCl; 0.05% Tween-20) for 1 hour. The blot was incubated with 1:100 anti-ERα (Abcam #ab16660) overnight at 4° C. After incubation the blot was washed with TBST and then incubated with HRP-conjugated secondary antibody (1:5000, GE Healthcare #NA934V) for 1 hour. Bands were detected using enhanced chemiluminescence solution and visualized using G-box imaging system (Syngene). The blot was washed with TBST and incubated with anti-β actin (1:5000, Sigma #A1978) overnight at 4° C. After washing with TBST and HRP secondary antibody incubation for 1 hour (1:5000, GE Healthcare #NA931C) bands were detected with enhanced chemiluminescence and G-box system. Expected molecular weights were 67 kDa (ERα) and 42 kDa (β actin).

Animal Treatment: Forty mature female mice (8 weeks old) BALB/c mice were purchased from Jackson Laboratory and housed in temperature-controlled facilities with a 12-hour alternating day/night light cycle and fed LabChow 5058 ad libitum. All procedures were in accordance with the national guidelines for the care and use of animals and approved by the University of Massachusetts Amherst's Institutional Animal Care and Use Committee.

The mice were ovariectomized before treatment. Briefly, each mouse was anaesthetized with a mix of isofluorance and oxygen. The flanks were shaved, sterilized with betadine and cleaned with alcohol. An incision was made to the skin on the right flank. The underlying muscle layer was nicked to reveal a small hole through which ovary was pulled out by grasping the periovarian fat. A Serrifin clamp was used to hold the ovary. After making sure the blood vessels were constricted to prevent breeding, the ovary was cut from the uterine horn. The periovarian fat was restored into the peritoneum. The peritoneum was closed with one or two stiches and the skin was closed with 9 mm wound clips. The procedure was repeated on the contralateral side. The mouse was monitored for a week post-procedure and wound clips were removed after 10 days. After 1 week of recovery, the mice began an acute oral treatment via pipette with one of three different compounds prepared in tocopherol-stripped corn oil for 4 days. Each mouse was administered 1 μL of oil per gram of body weight to deliver 250 μg/kg/d E2, 3000 μg/kg/d BP3 or 10000 μg/kg/d PP or vehicle control. For BP3 and PP, these doses represent the toxicologically no-adverse-effect-level (NOAEL) doses for each compound based on development and reproductive toxicity assays.

Six hours prior to sacrifice all of the mice were treated with 5-Gy dose of γ-irradiation. Then two hours before sacrifice all mice were injected intraperitoneally with 70 μg/g body weight of BrdU (Sigma Aldrich; Cat #B5002) that was previously prepared at 10 mg/ml in PBS and filter sterilized. The mice were sacrificed using carbon dioxide followed by cervical dislocation. Whole blood was collected by cardiac puncture and tissues were harvested. One of the 4th mammary gland was fixed in 10% NBF and transferred to 70% alcohol prior to paraffin-embedding. The other 4th mammary gland was removed of lymph node and stored in −70° C. The whole blood was allowed to coagulate at RT for 20 min and then spun down at 2000×g for 10 min at 4° C. to retrieve the serum.

Immunostaining of mouse mammary gland: Freshly cut 4 μM paraffin-embedded sections were deparaffinized/rehydrated with 100% xylenes 3 times for 5 min each, 2 times with 100% ethanol for 5 min each, 95% ethanol for 3 min and 70% ethanol for 3 min. Samples were rinsed with PBS. Antigen-unmasking was performed by boiling the samples in 1 mM EDTA for 1 hr. Samples were cooled down to RT and then treated with SSC 0.2× with gentle shaking at RT for 20 min. Samples were blocked in 3% BSA/PBS with 0.5% Tween-20 for 1 hr at RT. Primary antibody incubation was done with monoclonal 59.6/H2AX antibody for overnight at 4° C. After primary incubation, samples were washed 3 times with PBS containing 0.5% Tween-20 and then incubated with secondary antibody for 1 hr. Samples were washed 2 times with PBS containing 0.5% Tween-20 and 2 times with PBS and then mounted with Vectashield mounting medium containing DAPI. Slides were imaged at 60× with Nikon A1 Spectral Confocal microscope. Analysis of S9.6 intensity per nucleus or foci per nucleus were calculated using Nikon analysis software, where DAPI was used as a mask for the nucleus. IHC for Ki-67 was performed on a DakoCytomation autostainer using 1:1000 D2H10 primary antibody (cell signaling) and the Envision HRP detection system (Dako, Carpinteria, CA). Positive cells were counted using ImageJ software. 1200 cells were counted to determine percent Ki67 positive.

ELISA: The serum from whole blood that was harvested from all the mice were quantified using a 17β-estradiol specific enzyme-linked immunosorbent assay (ELISA) (Calbiotech Cat. #ES 180S-100).

Statistical Analyses: Unless specified, data were analyzed by one-way analysis of variance (ANOVA) followed by Tukey's honestly significant difference (HSD) multiple-range test using GraphPad Prism 8 statistical analysis software or R program (37). The difference between control and fulvestrant/RNaseH treated groups were evaluated with two-way ANOVA followed by Bonferroni correction. Results are presented as mean±standard error of the mean (SEM). Data were considered statistically significant at $p < 0.05$.

Results

Figure 1B:
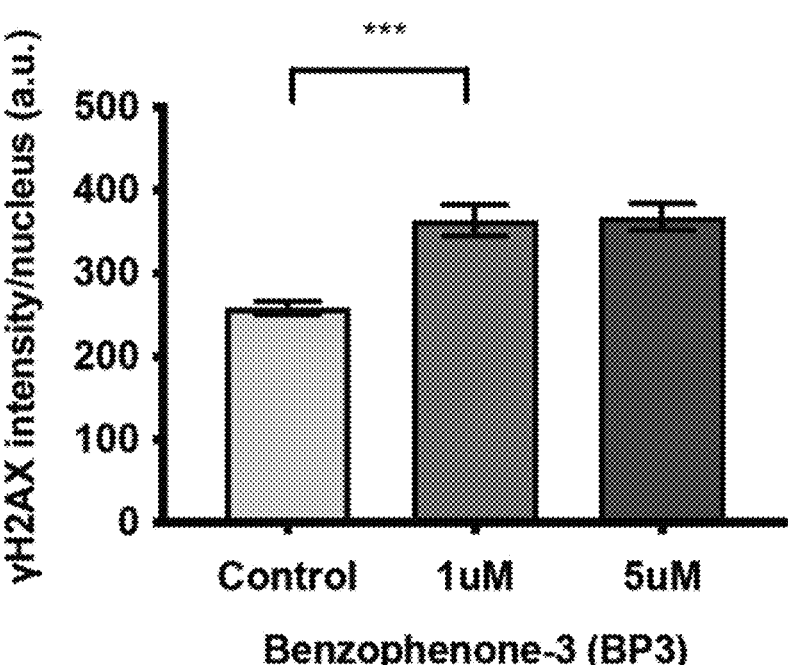
Figure 8:
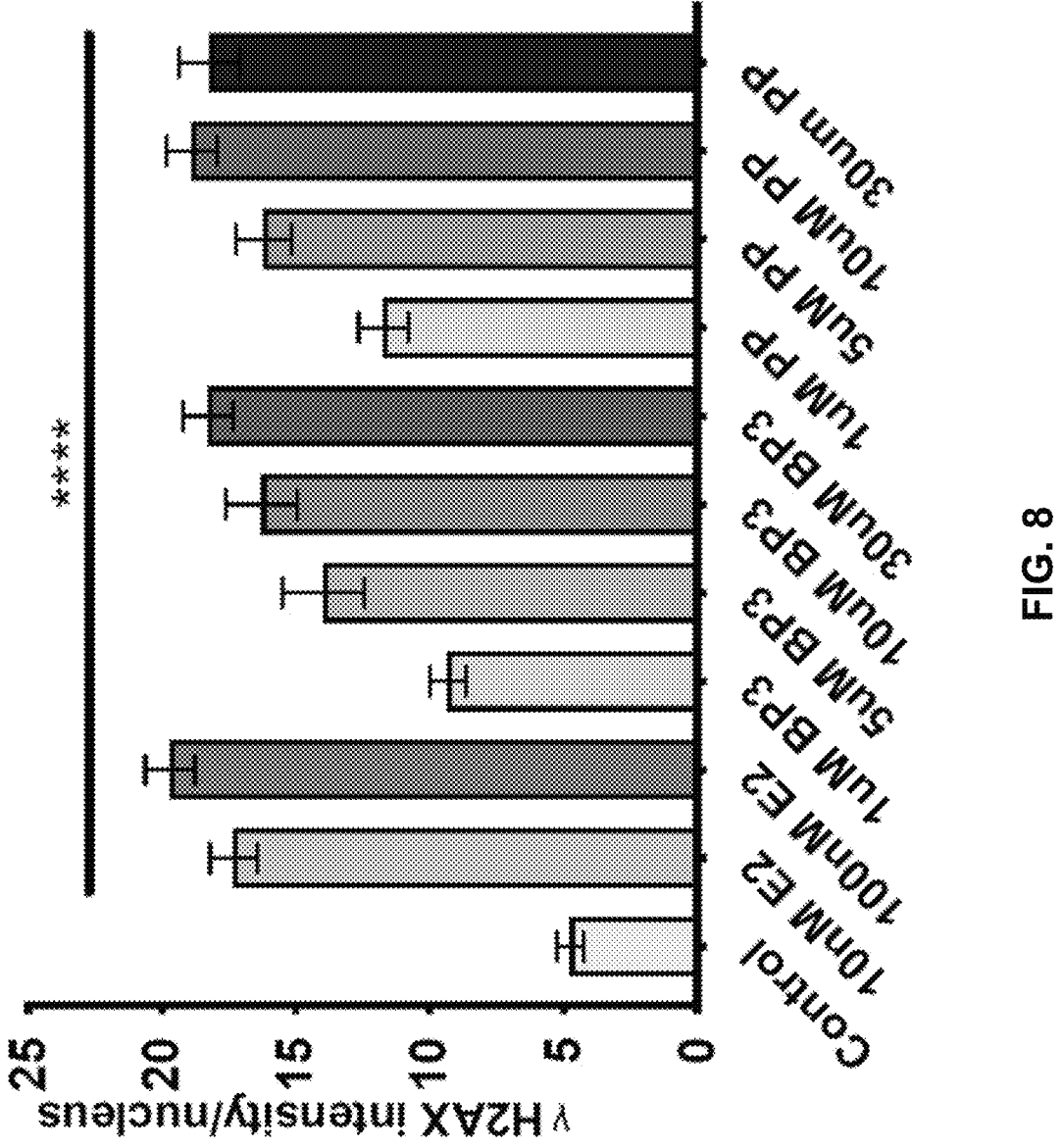
Figure 10:
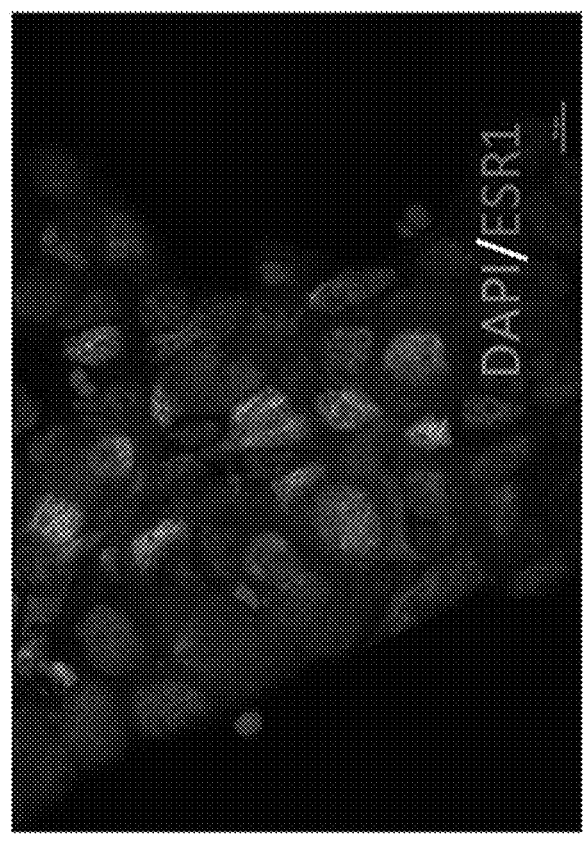
Figure 10:
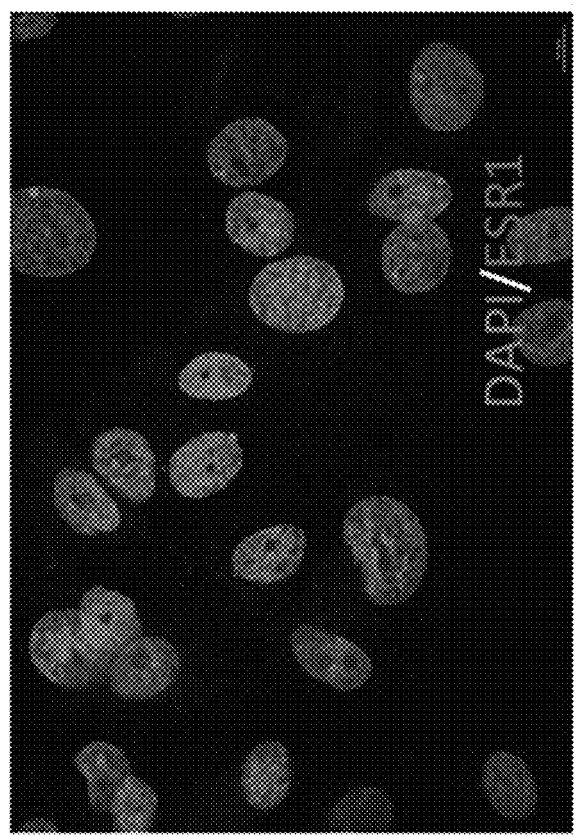
Figures 11A, 11B:
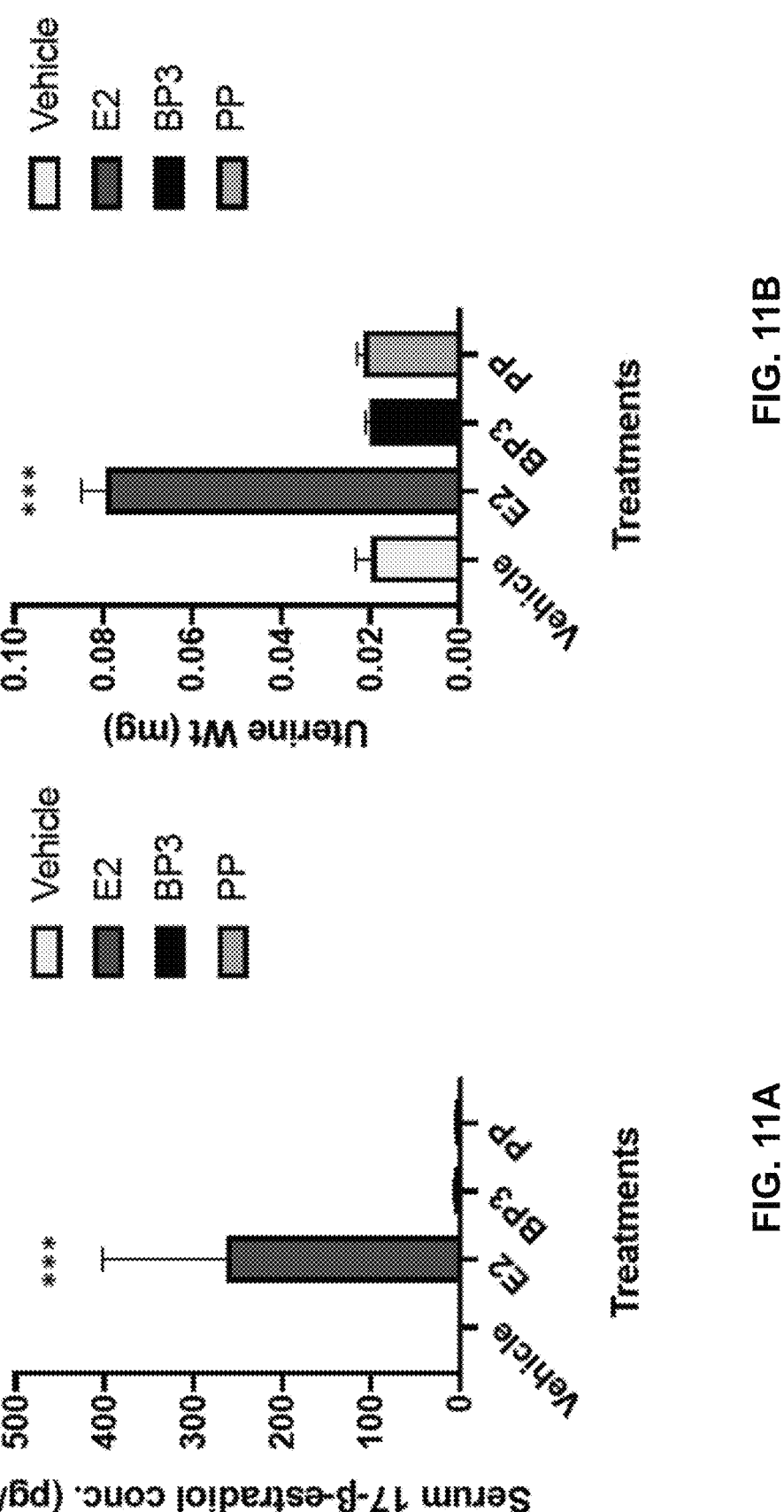
FIGS. 11A and 11B show serum 17$\beta$-estradiol levels (FIG. 11A) and uterine weight (FIG. 11B) from mice treated with E2 (250 $\mu$g/ml), BP3 (3000 $\mu$g/ml) and PP (10000 $\mu$g/ml).
Figure 12:
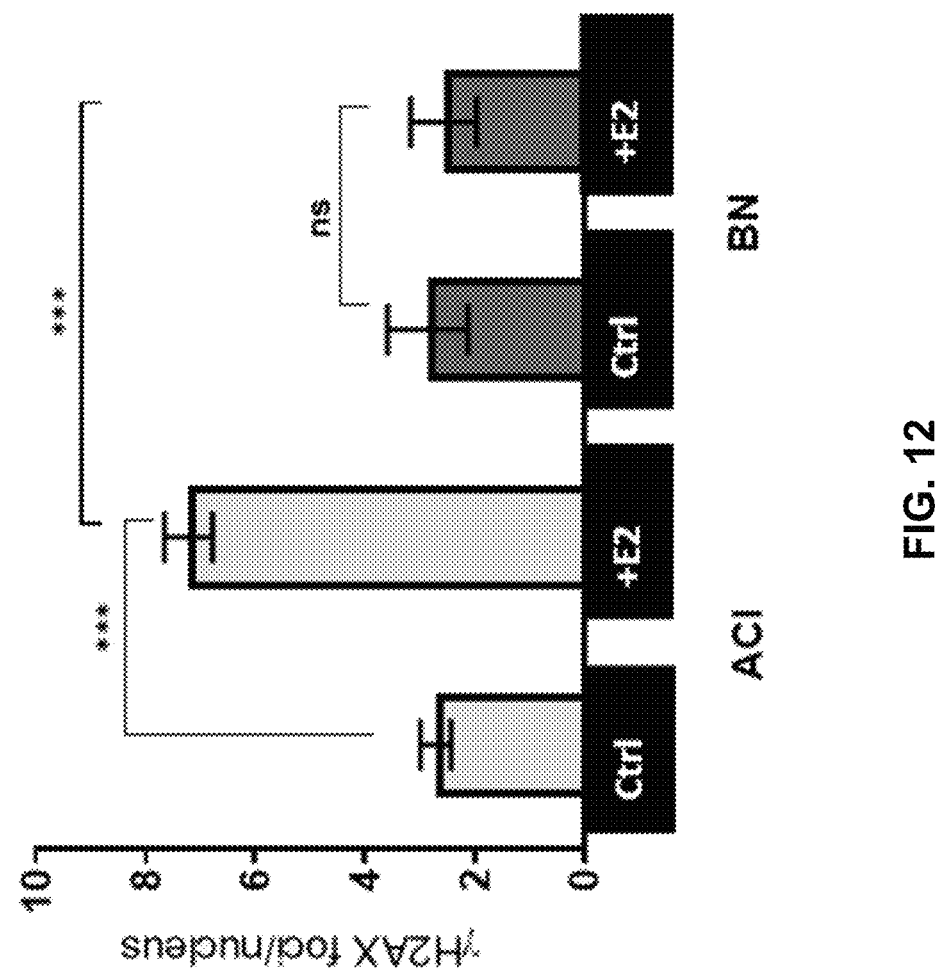
FIG. 12 shows DNA damage in strains of ACI (susceptible) and BN (resistant) rats that differ in tumor susceptibility.
Figure 13:
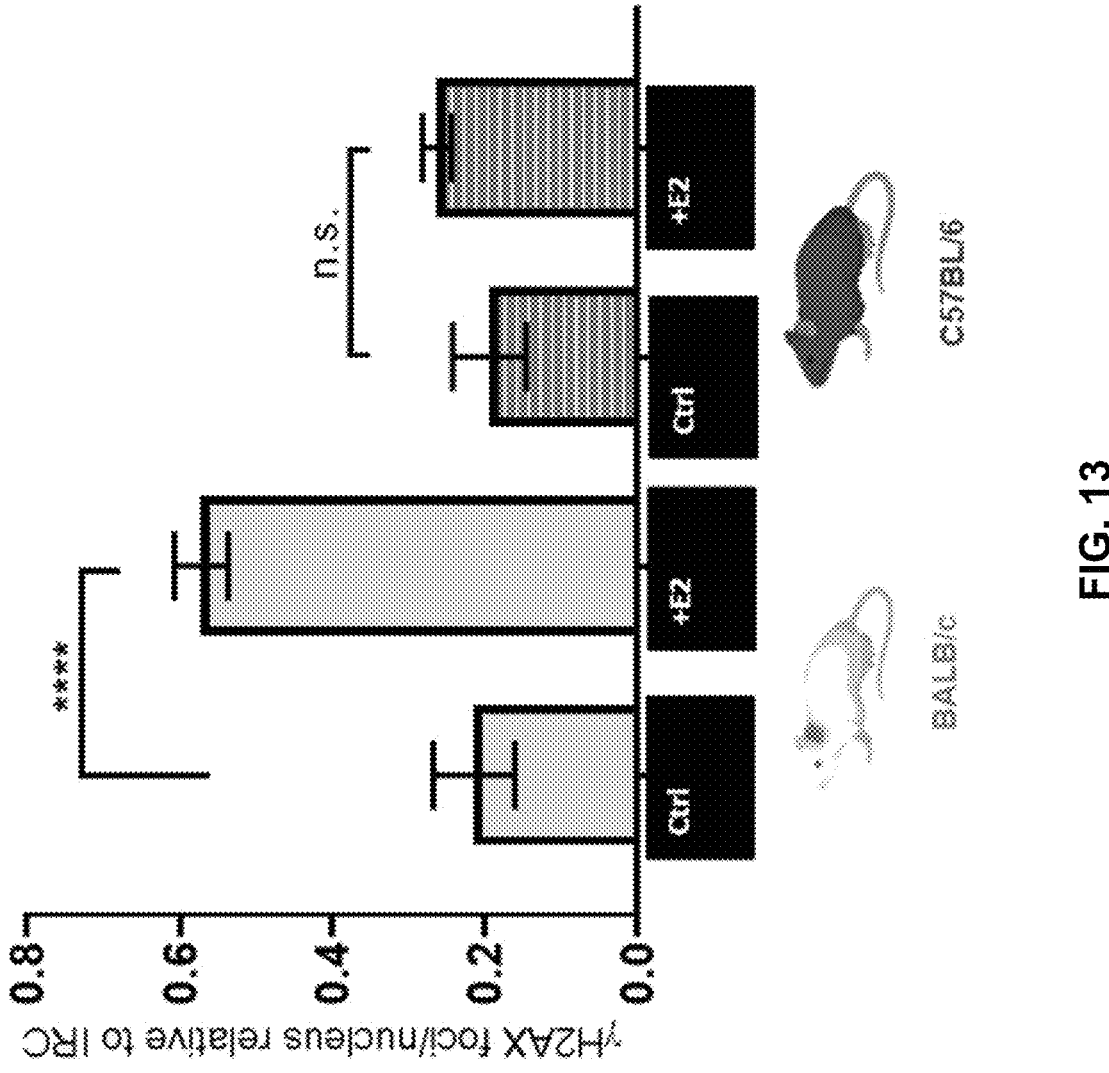
FIG. 13 shows DNA damage in strains of BALB/c (susceptible) and C57BL/6 (resistant) mice that differ in tumor susceptibility.
Figure 14A:
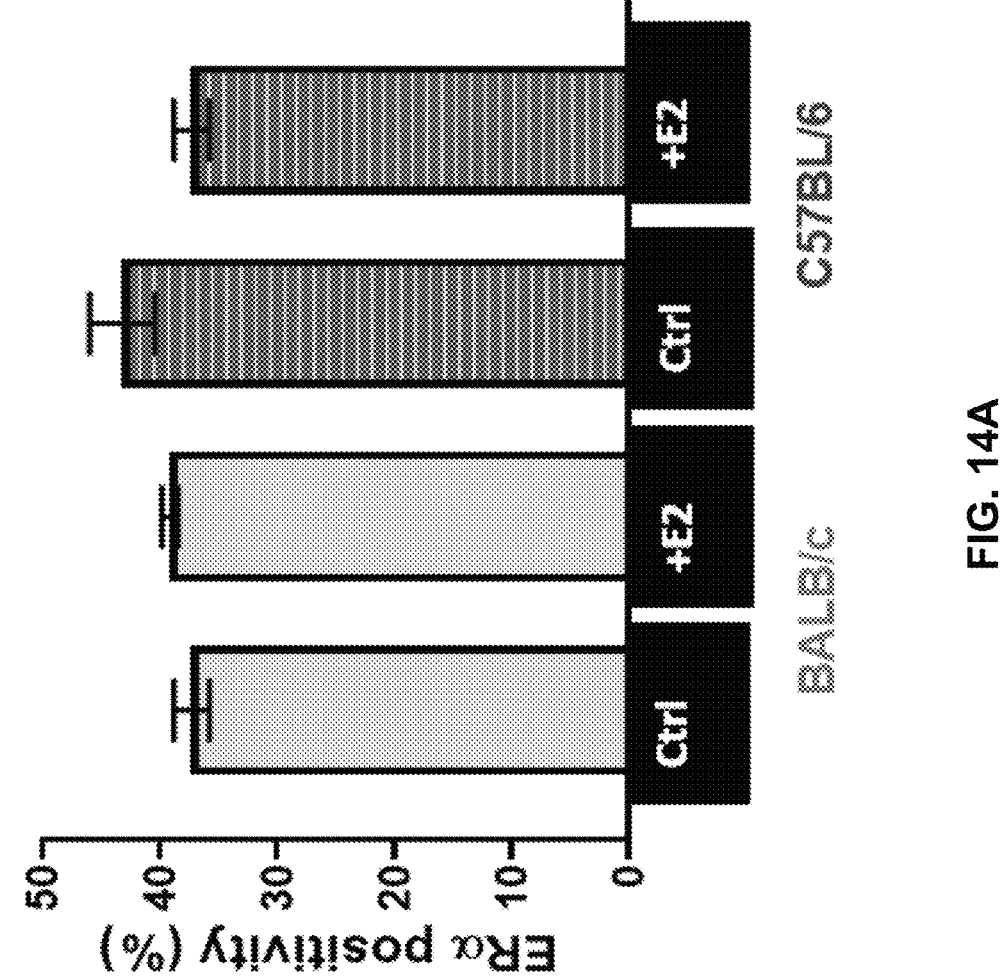
FIG. 14A shows levels of ERα do not differ between BALB/c and C57BL/6 strains.
Figure 14B:
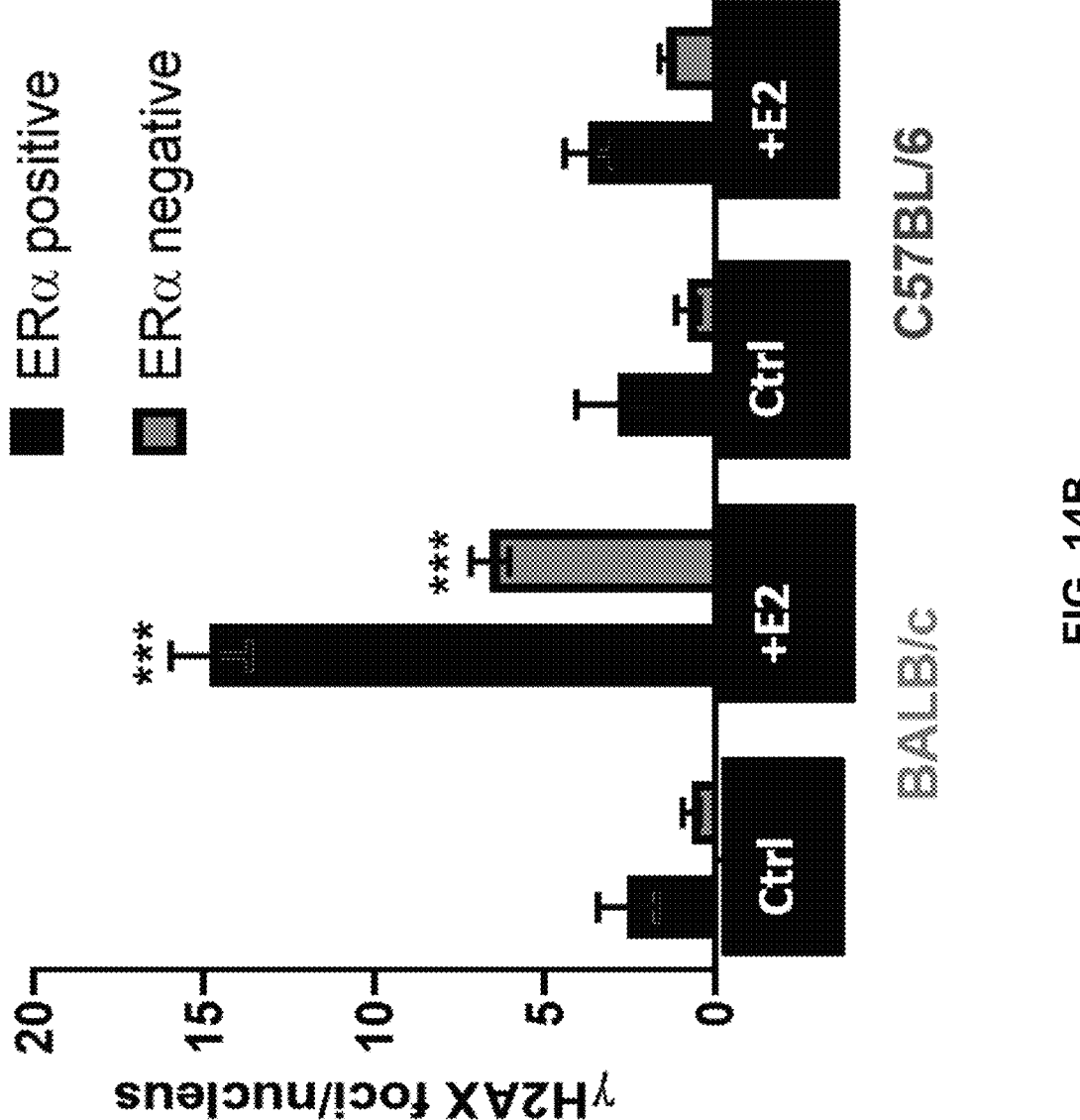
FIG. 14B shows DNA damage foci/ERα nucleus is much higher in BALB/c (mammary tumor sensitive strain).
Figure 14C:
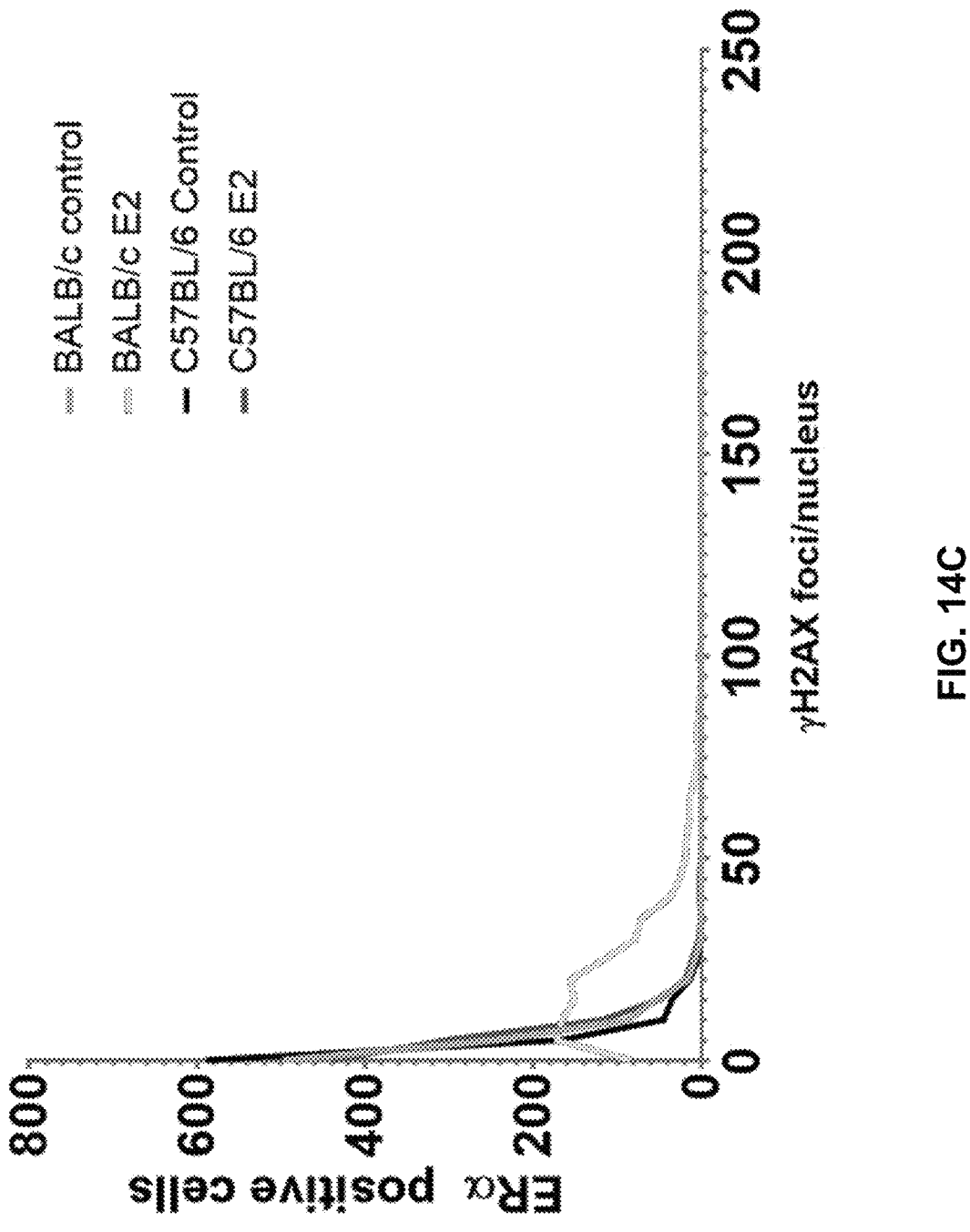
FIG. 14C shows the distribution of DNA damage/ERα-positive nucleus provides a cut-off for pathogenic levels of DNA damage foci. Using the frequency of >10 foci/ERα-positive nucleus provides a boundary associated with higher risk of mammary tumors in mice. We will be assessing this in human tissues as well.
Figure 15A:
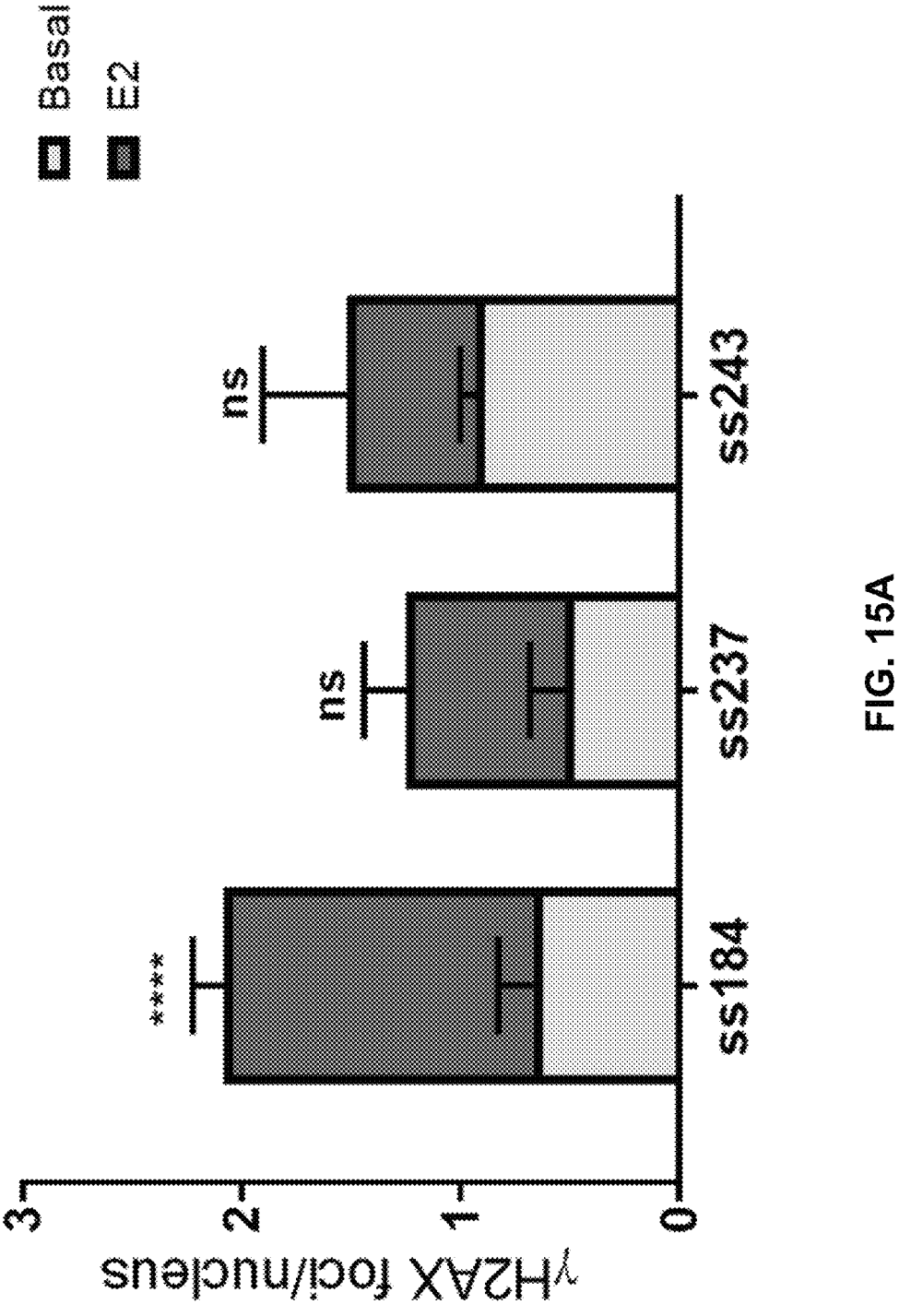
FIG. 15A shows variable levels of damage foci in "average risk" women.
Figure 15B:
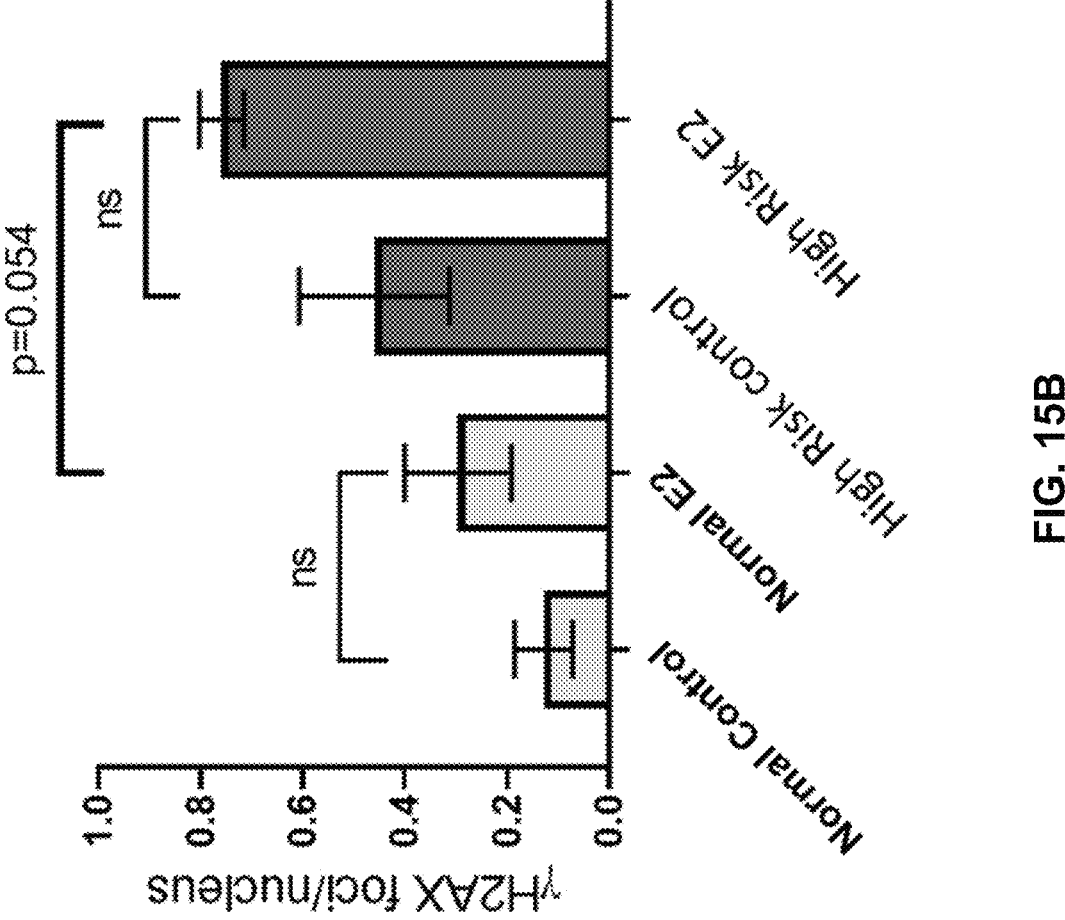
FIG. 15B shows E2-induced damage is elevated in high-risk women.
Figure 16:
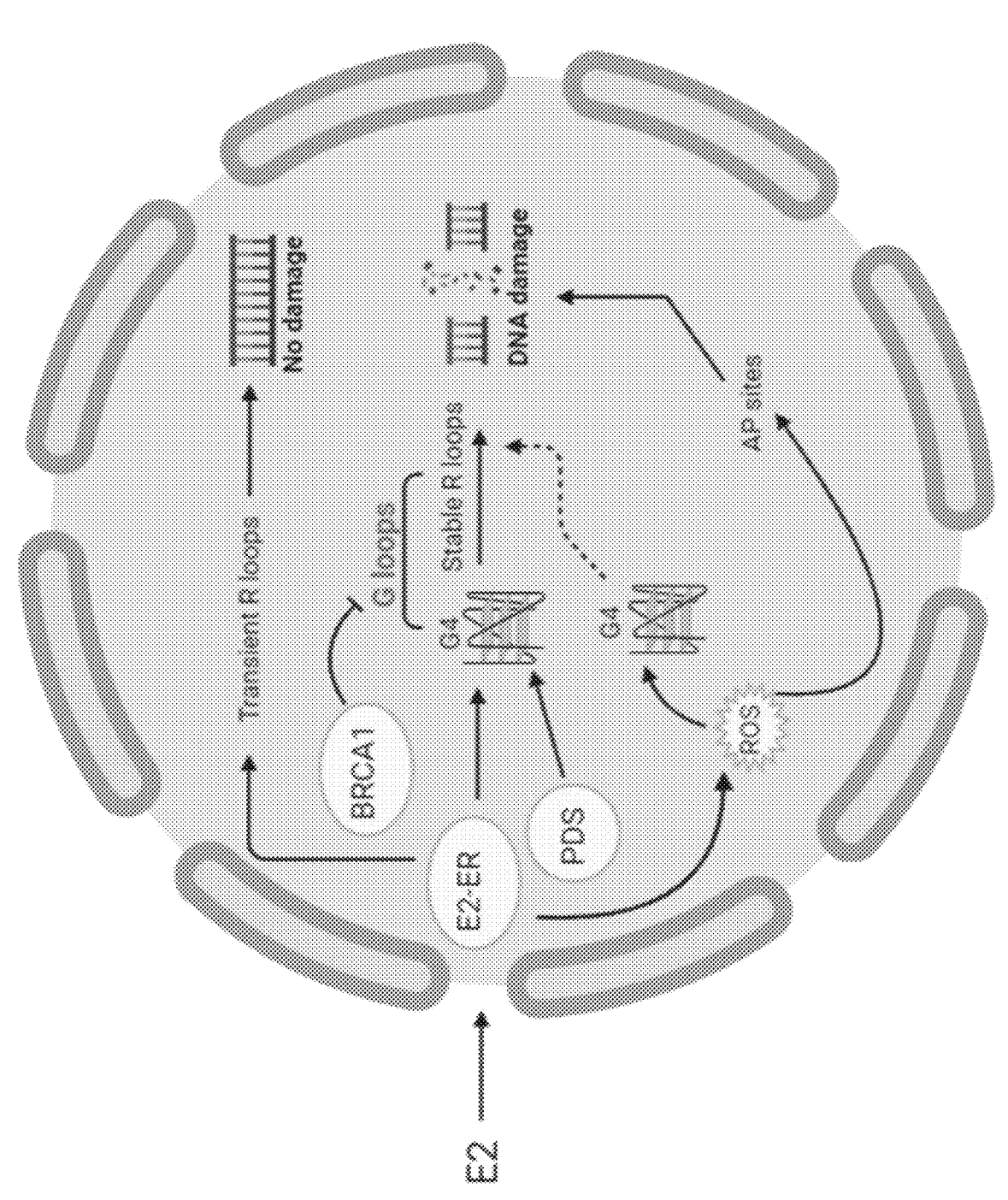
FIG. 16 illustrates the mechanism of ER-induced R-loop stabilization and DNA damage.

Both BP3 and PP induce ER-Dependent DNA-damage: γH2AX foci were monitored as a measure of DNA damage in T47D cells treated with the compounds for 24 h. A dose-dependent increase in γH2AX intensity was observed following E2 treatment (FIG. 1A). Treatment with either BP3 or PP also led to an increase in γH2AX intensity. Treatment with BP3 at 1 or 5 μM increased γH2AX intensity ($p < 0.0001$) although we did not observe a dose-dependent increase (1 μM BP3 vs 5 μM BP3, FIG. 1B). PP treatment also resulted in significantly higher γH2AX intensity at 1 and 5 μM compared to the control ($p < 0.0001$). The γH2AX intensity due to PP treatment was dose-dependent, similar to E2 (1 μM PP vs 5 μM PP, $p < 0.0001$) (FIG. 10). There was also a dose-dependent increase in nuclear γH2AX intensity in MCF-7 with treatment of E2 (10-100 nM), BP3 (1-30 μM) and PP (1-30 μM) (FIG. 8). The DNA damage was confirmed with immunostaining of 53BP1, a DNA damage response factor which localizes to the sites of DNA damage and forms ionization radiation induced foci. Similar to γH2AX intensity, there was a dose-dependent increases in 53BP1 nuclear intensity following treatment with E2 (10-100 nM) and PP (1-5 μM) in both T47D and MCF-7. BP3 treatment (1-5 μM) showed higher nuclear 53BP1 intensity over control in both T47D and MCF-7, but only MCF-7 showed dose-dependent increase (FIGS. 1D and 1E).

Figure 2B:
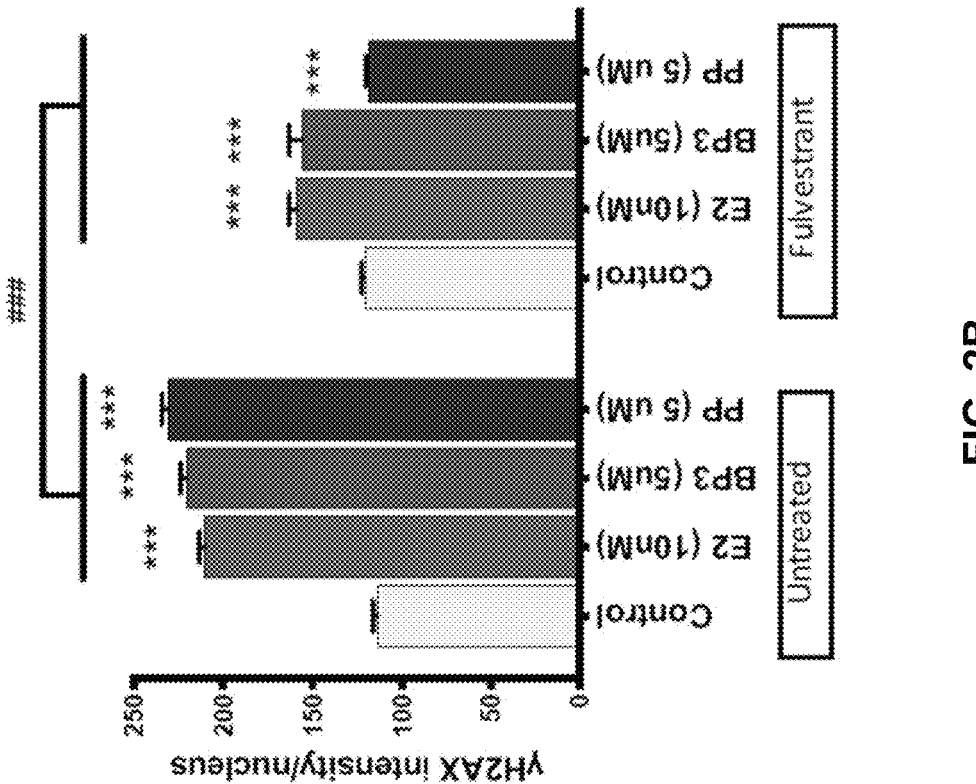
FIGS. 2A and 2B show ER-dependent transcriptional and DNA damage responses in T47D cells.
Figure 2A:
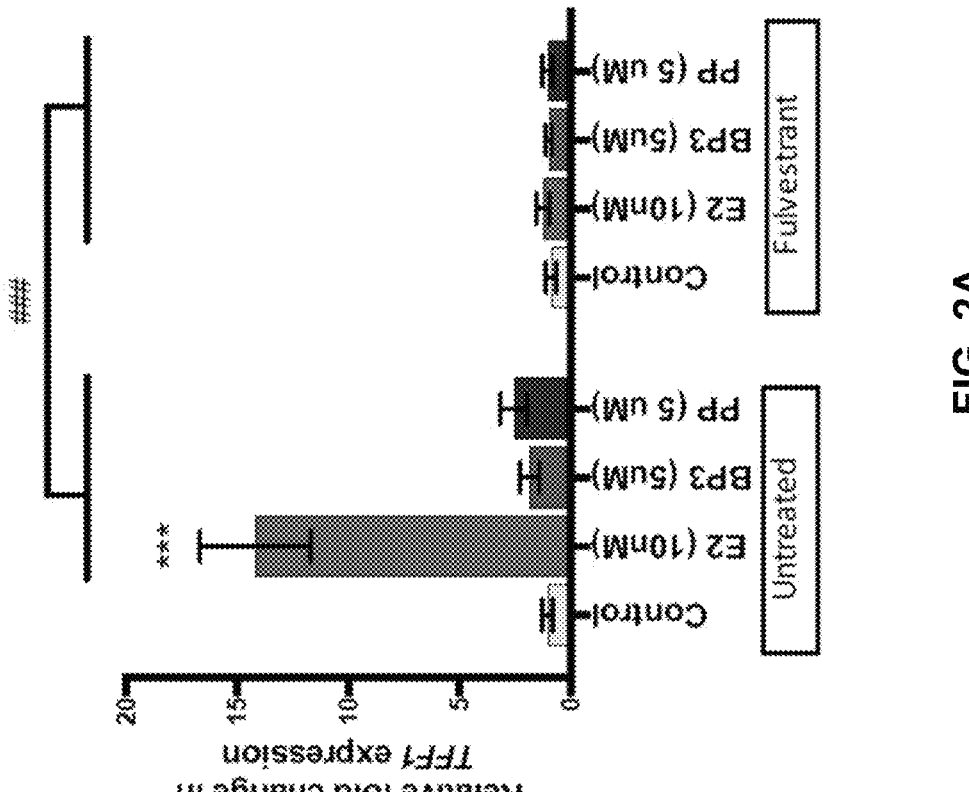

The effect on γH2AX was contrasted with the transcriptional activities of the compounds. Treatment with 10 nM E2 stimulated a 13.1 fold increase in expression of the estrogen-responsive gene TFF1, whereas responses to 5 μM BP3 or PP did not differ from the control (FIG. 2A). The transcriptional responses to E2 were blocked by treatment with fulvestrant (ICI 182,780, 1 μM) demonstrating the dependence on ER. Blocking ER with fulvestrant also significantly reduced the effect of E2 on γH2AX intensity (FIG. 2B, p<0.0001) and inhibited γH2AX intensity in response to 5 μM BP3 (p<0.0001) and 5 μM PP (p<0.0001) suggesting that the induction of DNA damage was, in part, dependent upon ER. However, the γH2AX foci induced by E2 and BP3 was incompletely blocked by fulvestrant compared to its inhibition of TFF1 expression. Thus, it is possible that some of the effect on γH2AX foci may be independent of ER or a higher concentration of fulvestrant may be required to completely block ER-mediated DNA damage.

Figure 1C:
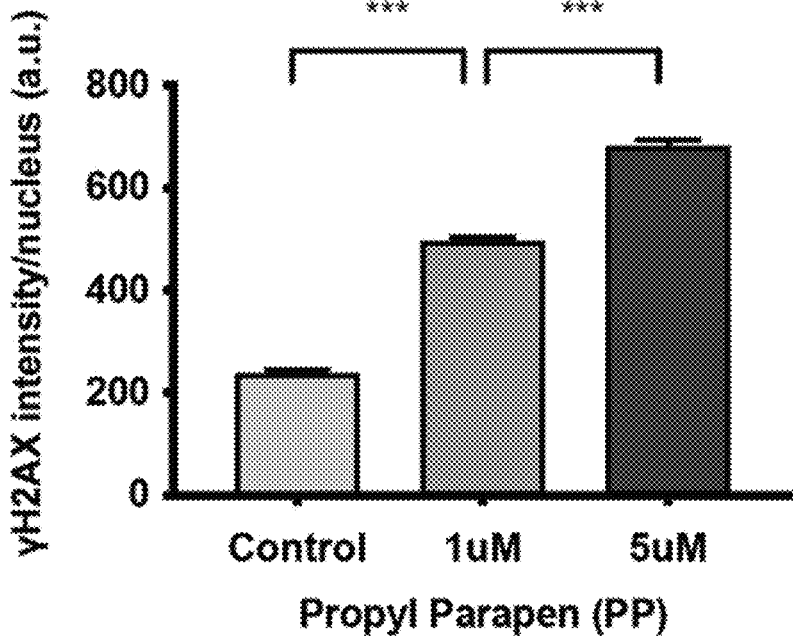
Figure 3A:
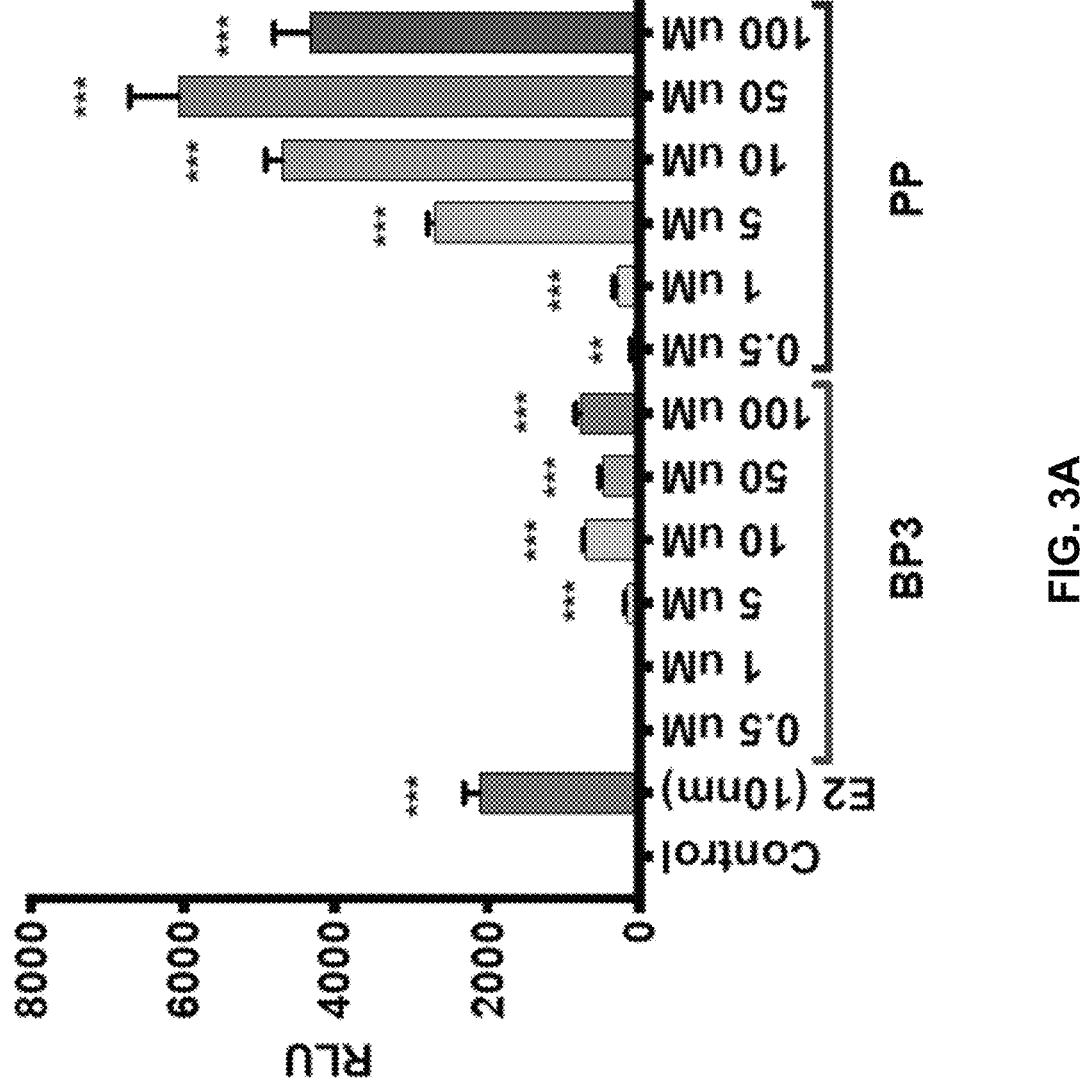
FIGS. 3A to 3D show estrogen-receptor transactivation with E2, BP3 and PP.
Figure 3B:
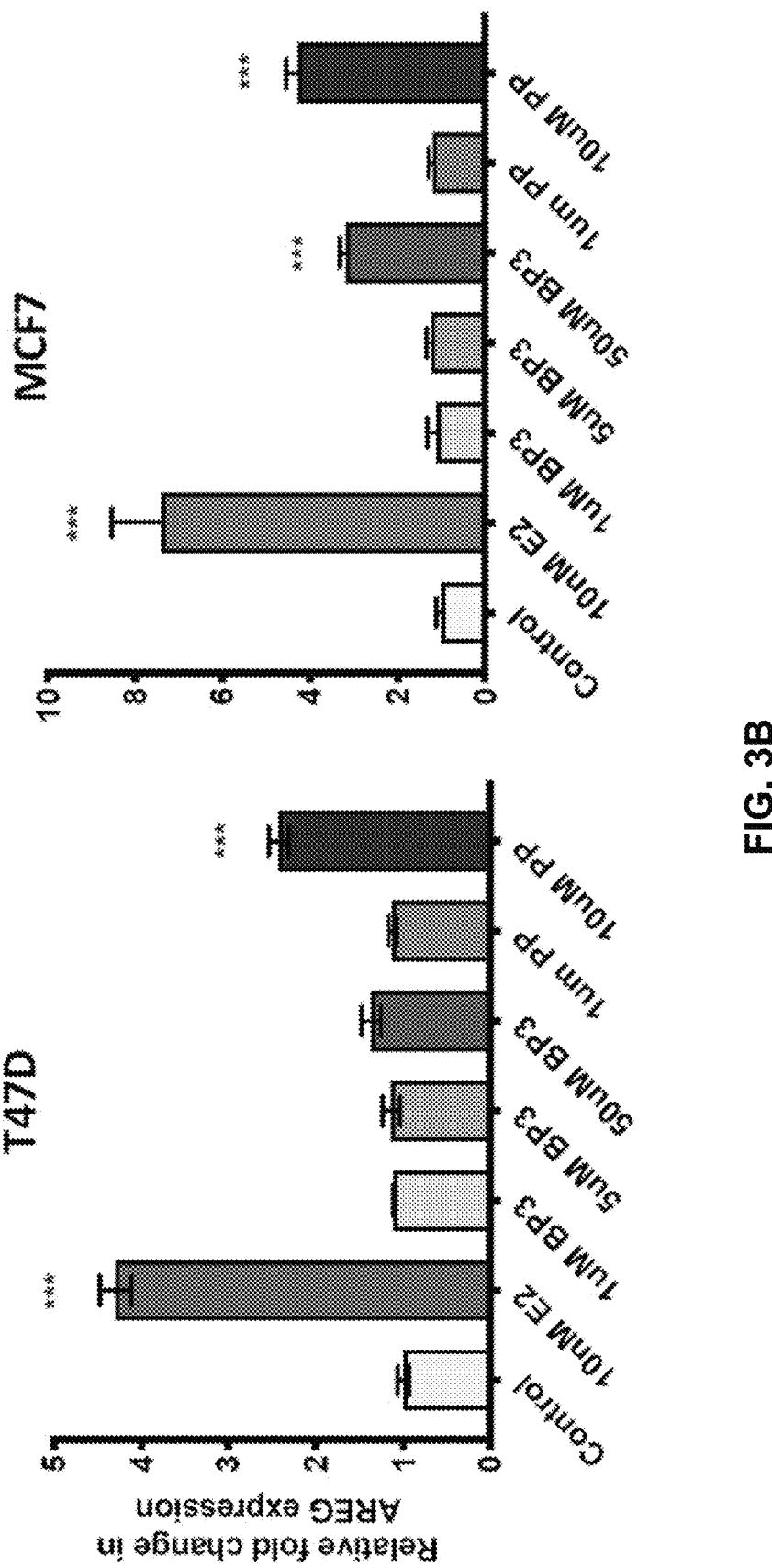
Figure 3C:
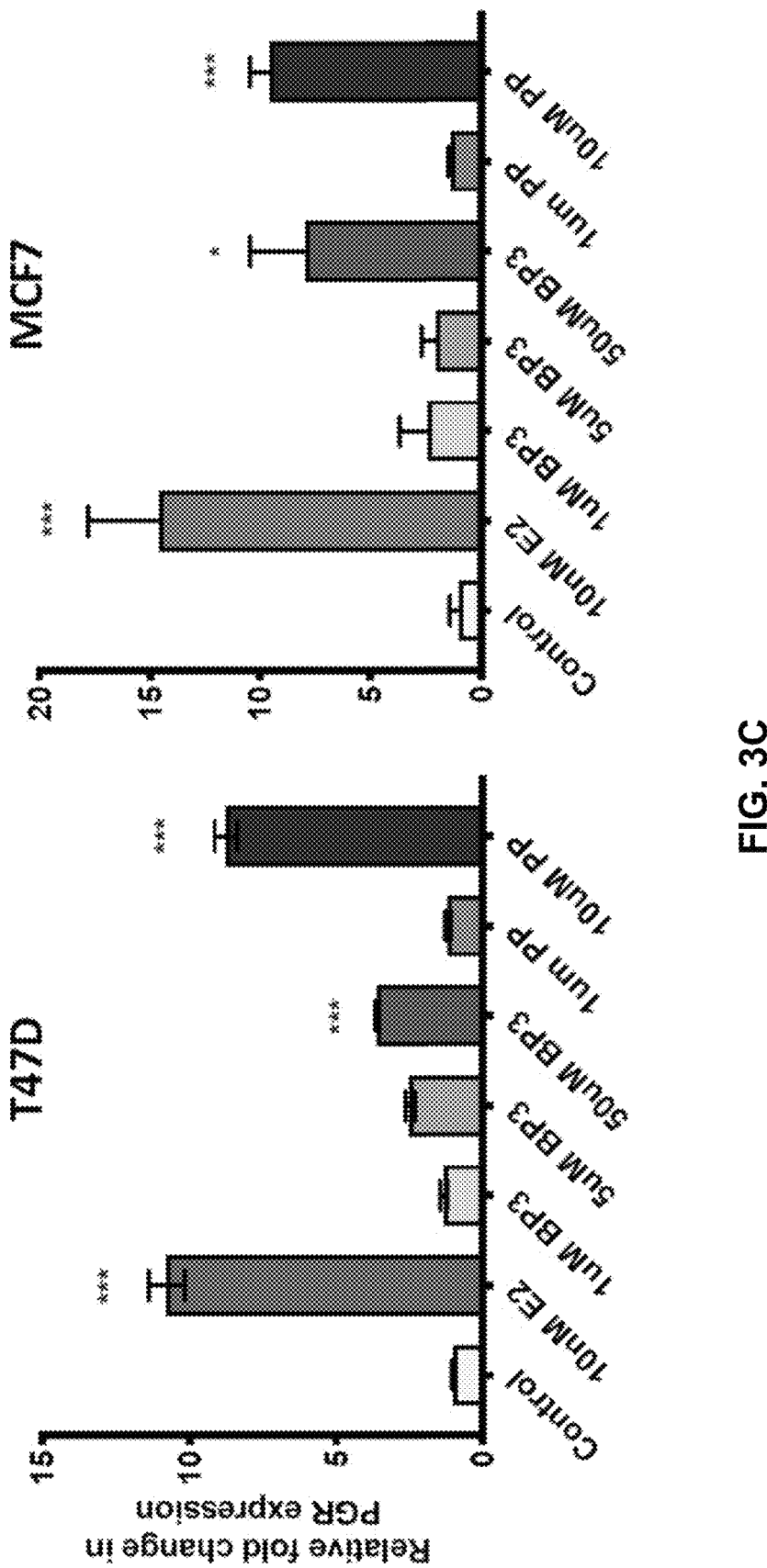
Figure 3D:
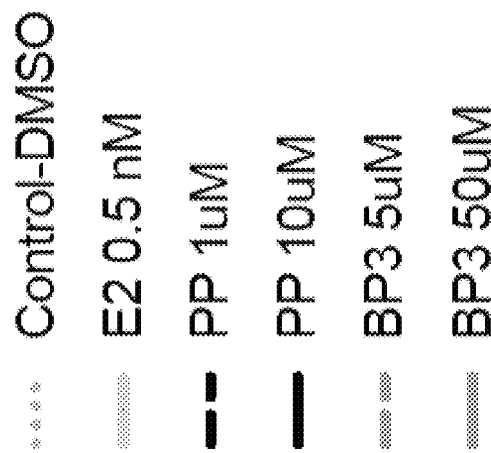
Figure 3D:
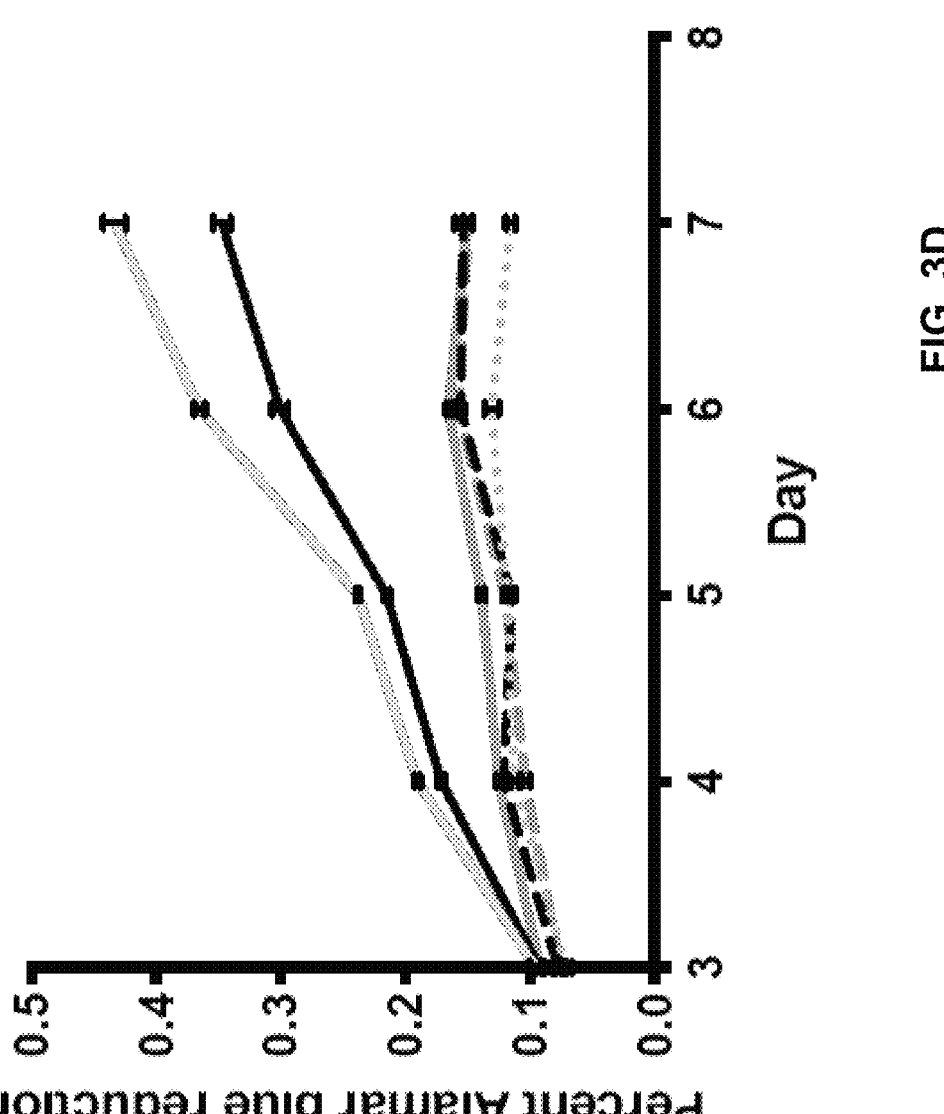
Figure 9:
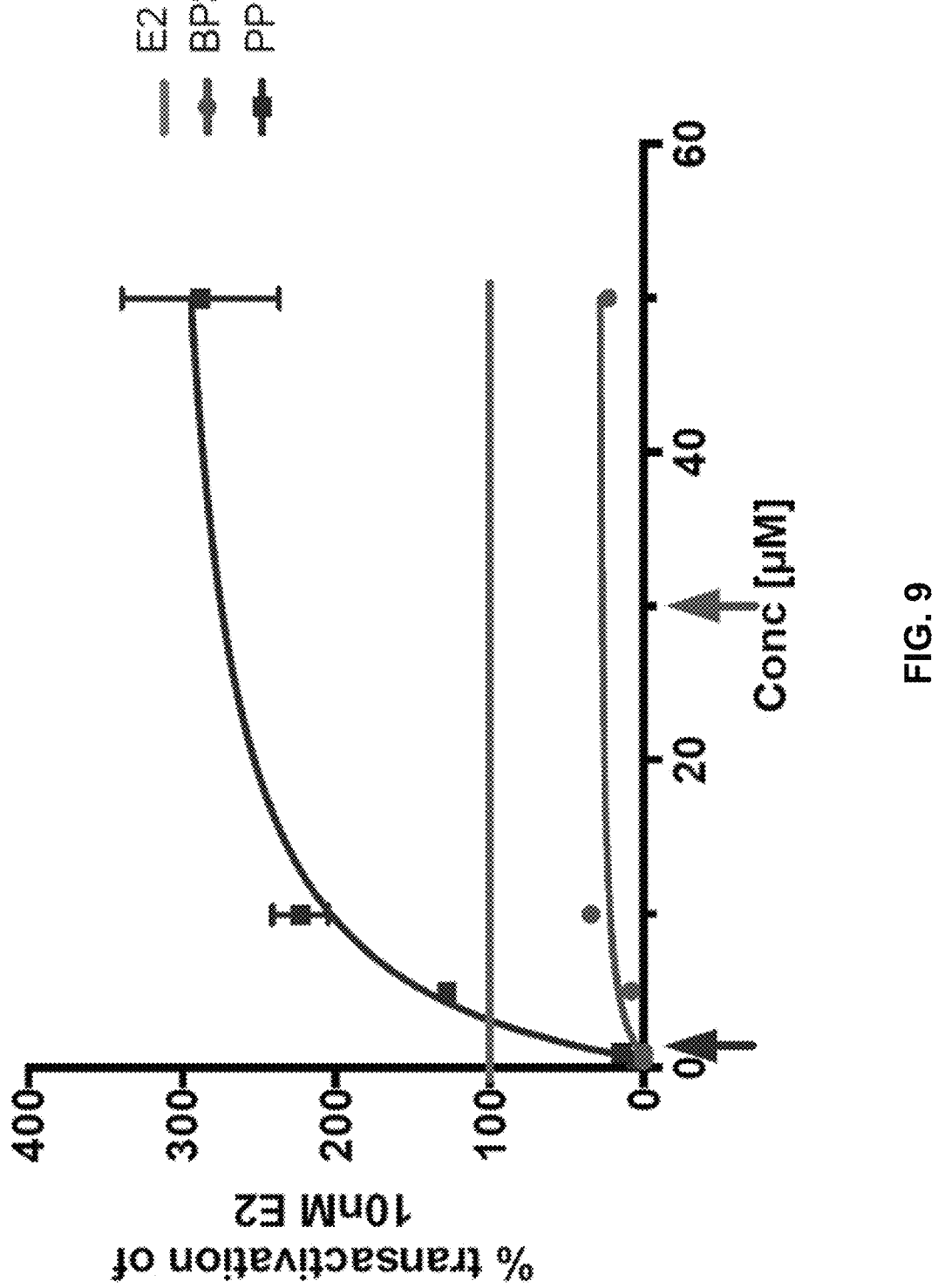

BP3 and PP are poor estrogen receptor agonists: Reporter assays provide a sensitive means to evaluate estrogenic activity on a minimal promoter whereas endogenous genes containing estrogen responsive elements provide physiologically relevant targets. 10 nM E2 is sufficient to saturate responses in these assays, hence it was used as positive control that is relevant to physiologic E2 levels (2-70 nM) in women (Table 2). T47D-KBluc cells harbor an integrated ERE-luciferase reporter in which BP3 shows a lowest-observed-effect at 5 μM with transactivation increasing to a maximum 37% relative transactivation activity (RTA) compared to 10 nM E2 (FIG. 3A). In contrast, PP showed 4.7% RTA at 0.5 μM and increased to 288% at 50 μM. To estimate the transactivation activity relevant in humans, the published urinary levels of BP3 and PP were used (Table 2). At concentrations measured in the 95th percentile of pregnant women, BP3 had 27.16±6.2% and PP had 104.07±20.98% RTA (FIG. 9). Induction of endogenous ER target genes AREG and PGR were also quantified in T47D and MCF-7 cell lines (FIGS. 3B and 3C). BP3 and PP are poor agonists at 1 μM, a concentration that induced significant increases in DNA damage (FIG. 1). Proliferation induced by these compounds was also compared to provide an additional measure of their bioactivity (FIG. 3D, Table 3). At 10 μM, PP stimulates significant proliferation but not at 1 μM PP. However, BP3 had marginal effect at 5 or 50 μM. Low concentrations of BP3 and PP only marginally increase cell numbers compared to control. These results demonstrate that DNA damage can occur at low concentrations of BP3 and PP (1-5 μM) in the absence of detectable expression of either a synthetic estrogen responsive reporter, endogenous target genes or proliferative responses.

TABLE 2

Estimation of estrogen and xenoestrogens concentrations in urine/blood samples of women.

| Ligand | Median (μM) | 90% ile[a] or 95% ile[b] (μM) | Relative Transactivation Activity at 90% ile or 95% ile (% RTA vs E2) |
|---|---|---|---|
| BP3 (urine) | | | |
| Non-Pregnant | 0.137 | 6.70[b] | 18.91 ± 6.62% |
| Pregnant | 0.47 | 29.5[b] | 27.16 ± 6.2% |
| PP (urine) | | | |
| Non-Pregnant | 0.161 | 1.98[b] | 64.27 ± 20.5% |
| Pregnant Human, | 0.253 | 3.26[b] | 104.07 ± 20.98% |

TABLE 2-continued

Estimation of estrogen and xenoestrogens concentrations in urine/blood samples of women.

| Ligand | Median (μM) | 90% ile[a] or 95% ile[b] (μM) | Relative Transactivation Activity at 90% ile or 95% ile (% RTA vs E2) |
|---|---|---|---|
| E2 (blood) | | | |
| Ovulatory | 0.0003-0.0018 | | |
| Luteal | 0.0002-0.0008 | | |
| Pregnancy | 0.074 | 0.118[a] | |
| Mouse | | | |
| E2 (blood) | <0.0003 | | |

TABLE 3

Slopes of growth curve effect on E2, BP3 and PP on T47D cells.

| Growth Curve | Slope | 95% CI |
|---|---|---|
| Control DMSO | 0.0107 | −0.006811 to 0.02821 |
| 0.5 nM E2 | 0.08495 | 0.06604 to 0.1039 |
| 1 μM PP | 0.01856 | 0.003943 to 0.03318 |
| 10 μM PP | 0.06387 | 0.05225 to 0.07550 |
| 5 μM BP3 | 0.0202 | 0.008131 to 0.03226 |
| 50 μM BP3 | 0.01581 | 0.0009721 to 0.03064 |

Figure 4A:
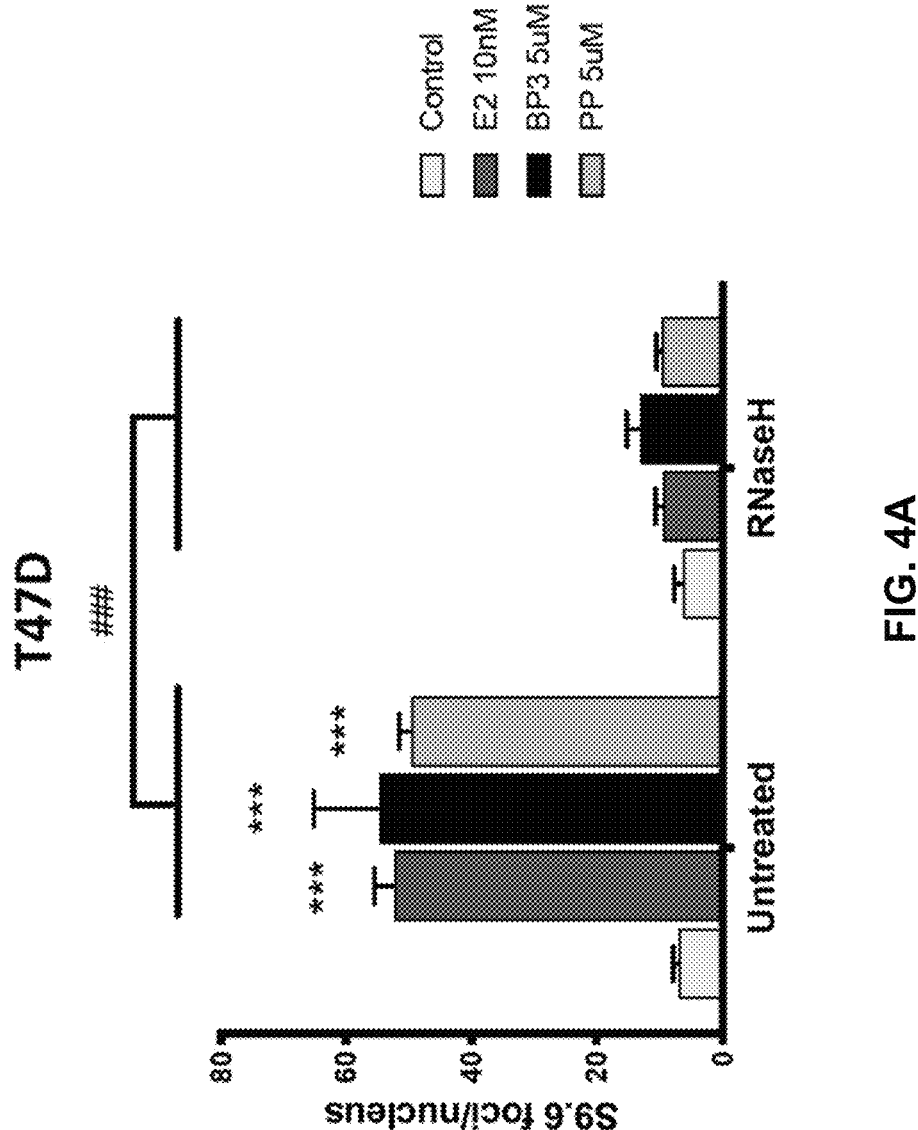
FIGS. 4A and 4B show induction of R-loop formation by E2, BP3 and PP.
Figure 4B:
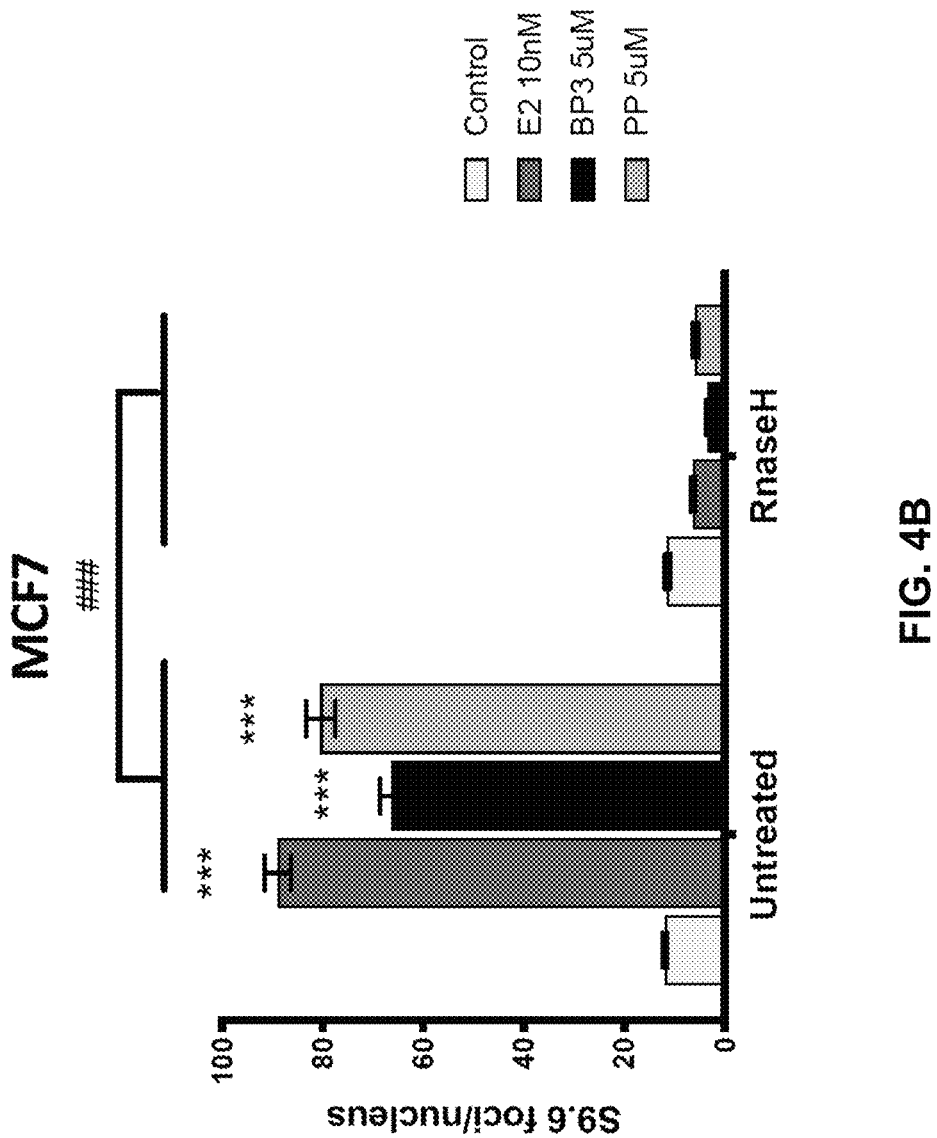

BP3 and PP induce DNA-damage via R-loop: R-loop formation was investigated as a possible mechanism of DNA damage using the S9.6 antibody to specifically detect DNA:RNA hybrids. While there was a basal level of R-loop foci in the vehicle-treated control in T47D cells, nuclear S9.6 foci was significantly higher with 5 μM of BP3 or PP treatment and comparable to responses with 10 nM E2. Addition of RNaseH to the cells treated with 5 μM BP3 or PP or 10 nM E2 abolished the S9.6 intensities, confirming the specificity of S9.6 nuclear staining (FIG. 4A). Similar induction of R-loops was obtained with 10 nM E2, 5 μM BP3 or 5 μM PP treatment of MCF-7 cells which was abrogated following RNase addition post-fixation (FIG. 4B).

Figure 5A:
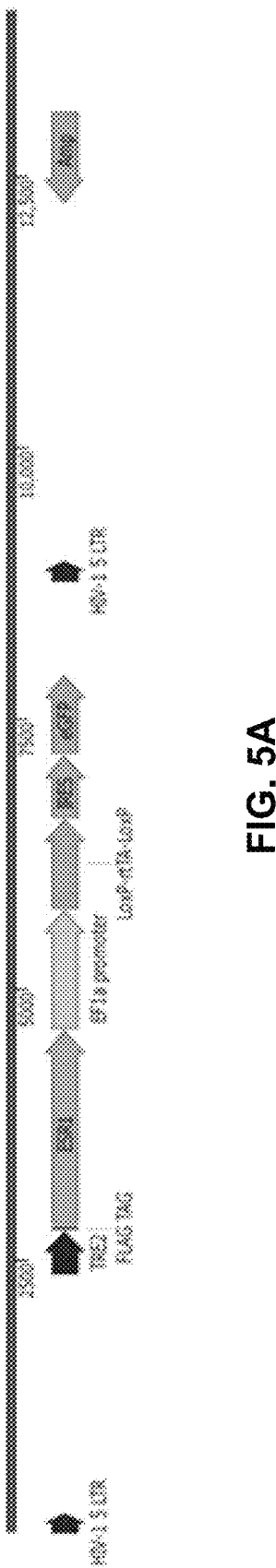
FIGS. 5A to 5C show induction of R-loop in normal breast epithelial cells 76N-tert expressing ER$\alpha$.
Figure 5B:
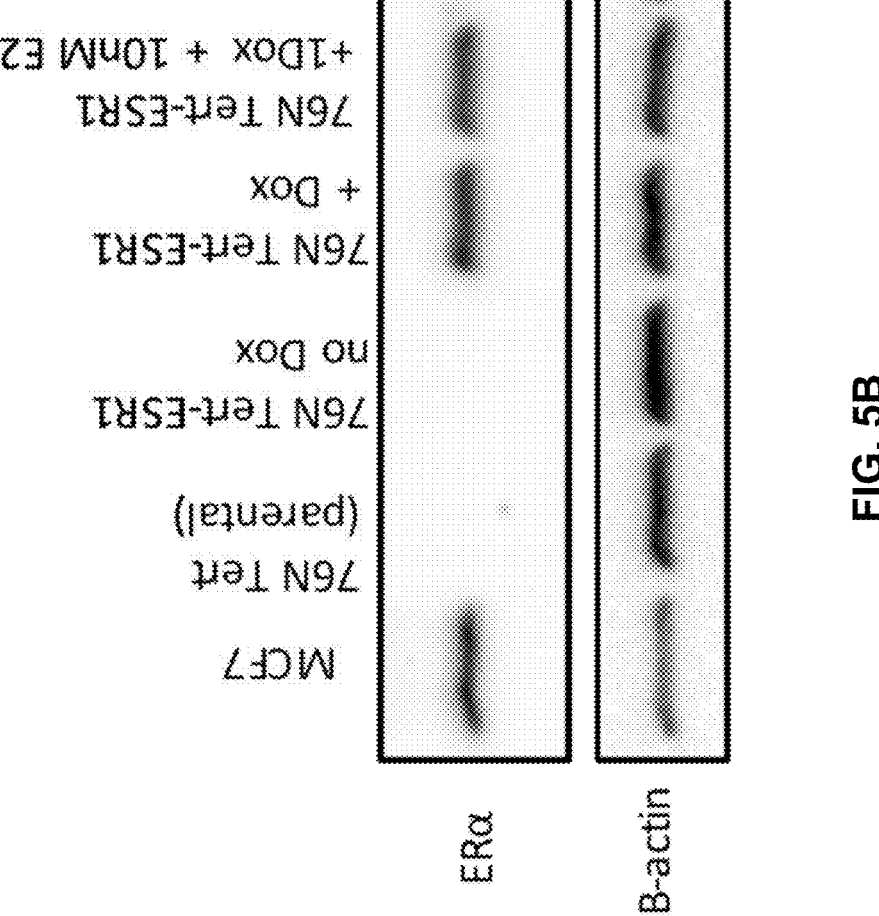
Figure 5C:
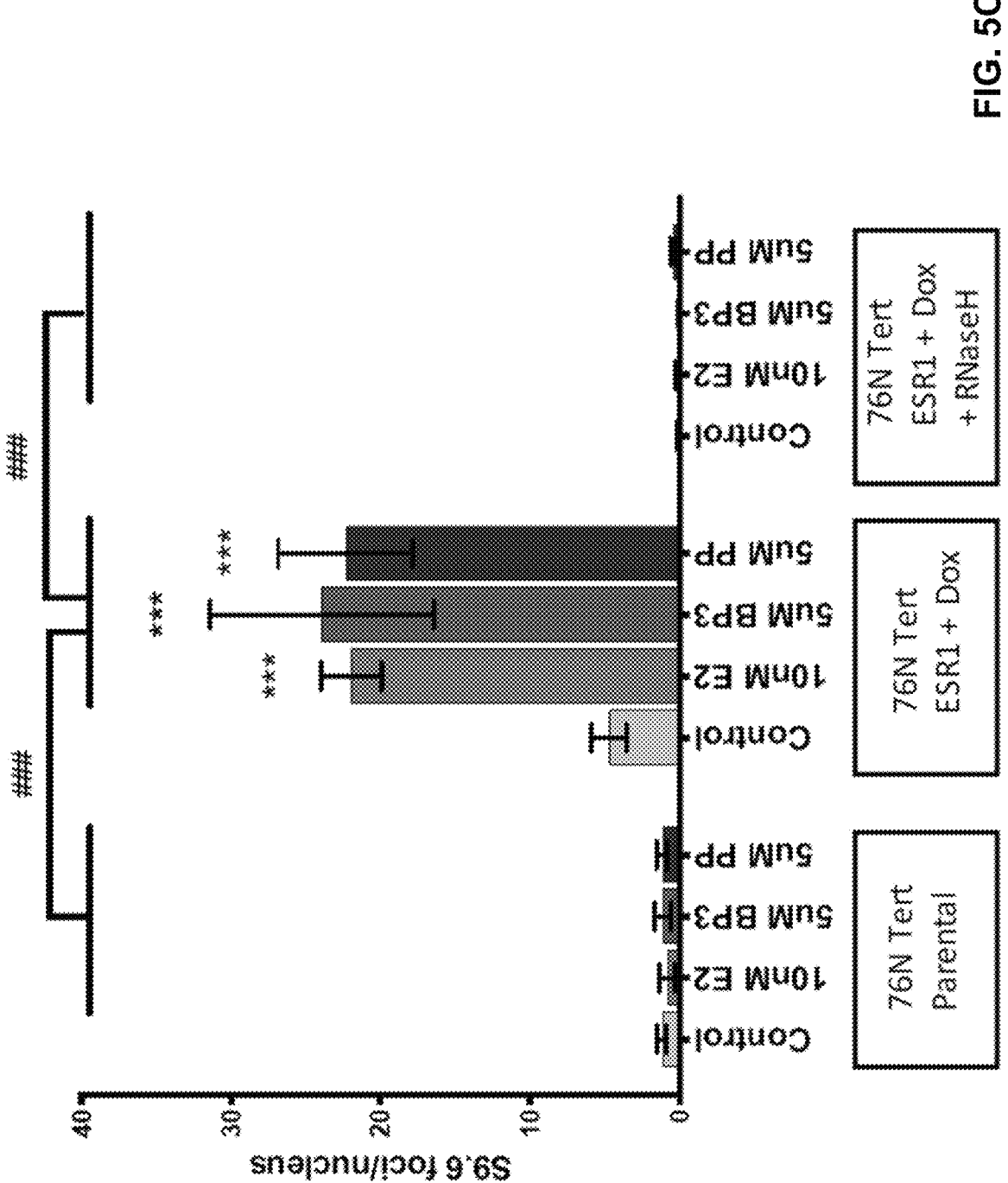

R-loop formation is ER-dependent in breast epithelial cells: Next asked was whether R-loops form in normal breast epithelial cells in response to exposures of BP3 and PP. The 76N-Tert cells do not express endogenous ESR1 providing a null background to test ERα-stimulated R-loops. The cells were stably infected with an inducible human ESR1 (pINDUCER-ESR1, FIG. 5A). ERα expression was confirmed with western blot (FIG. 5B). MCF-7 cell lysate was used as a positive control. Immunofluorescence showed 90% of the cell population are GFP+ (ERα expressing) (FIG. 10).

In the parental 76N-tert cell line, which does not express ERα, treatment with E2, BP3 or PP showed low nuclear S9.6 staining. After induction of ERα with doxycycline, 5 μM BP3 and PP increased number of nuclear S9.6 foci significantly over vehicle-treated control and comparable to 10 nM E2 treatment. RNaseH treatment reduced nuclear S9.6 foci in 10 nM E2 treated as well as 5 μM BP3 or PP treated 76N-Tert-ESR1 cell line induced with doxycycline (p<0.0001, FIGS. 4C & 4D). These data confirm ERα dependency of R-loop formation in breast epithelial cells, and that low concentration (5 μM) of BP3 and PP can induce R-loop.

Figure 6C:
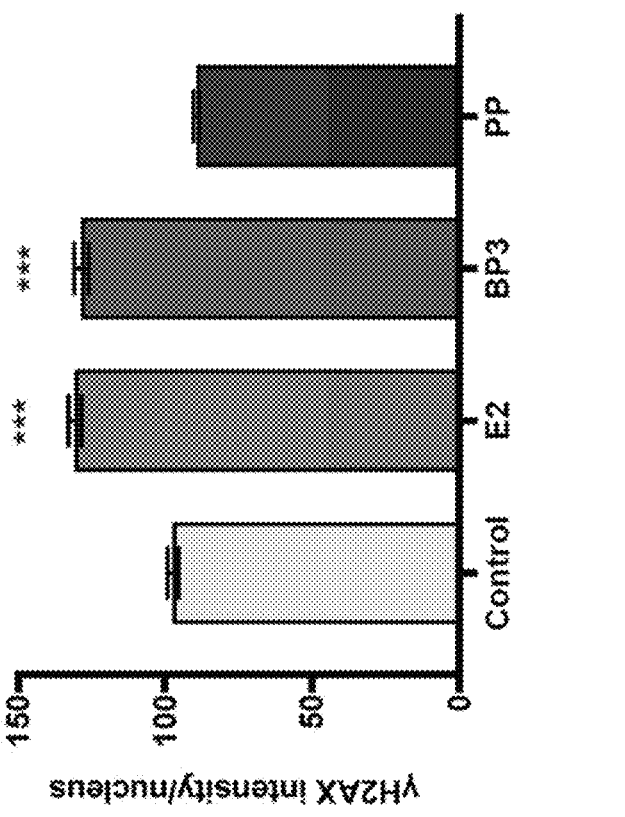
Figure 6B:
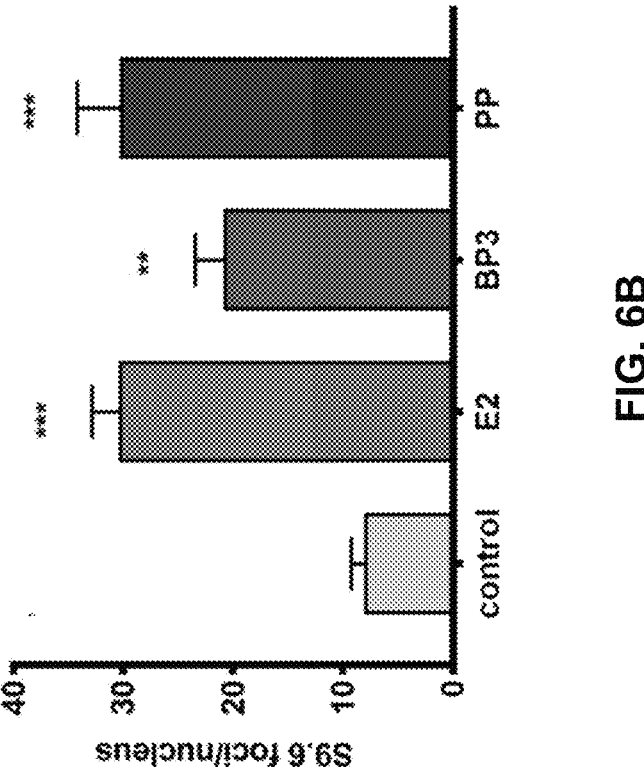
Figure 6E:
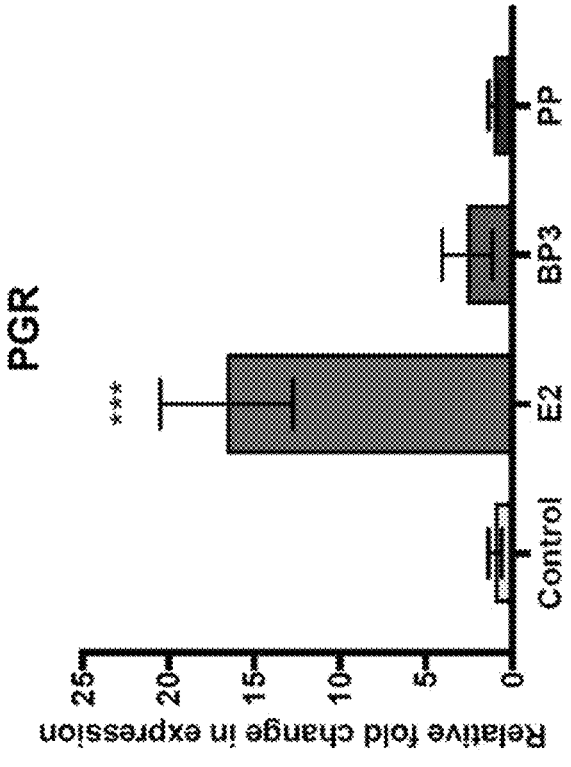

Short-term exposure causes R-loop and DNA damage formation in vivo: To evaluate the relevance of exposure to xenoestrogens in vivo, ovariectomized mice were treated orally with E2 (250 µg/kg/day), BP3 (3,000 µg/kg/day) or PP (10,000 µg/kg/day) for 4 days (FIG. 6A). These doses have been used in experiments evaluating effects of chronic exposures on mammary gland development (LaPlante CD, et al. J Endocr Soc 2018 2:903-921). There was a 3.8-fold enhanced nuclear S9.6 staining in the mammary epithelium of E2 treated animals over control treated animals. Exposure to BP3 also induced 2.5-fold nuclear S9.6 straining in the mammary epithelial cells whereas PP induced 3.8-fold increase compared to control-treated animals (FIG. 6B). Nuclear γH2AX intensity in the mammary gland of E2 and BP3 treated animals was significantly higher than animals treated with vehicle control (FIG. 6C). While oral E2 stimulated proliferation and transcriptional activation of ER-target genes (Areg and Pgr), neither BP3 nor PP elicited significant responses (FIG. 6D-6G). These results demonstrate that BP3 and PP induce R-loops and DNA damage similarly to E2, but without inducing transcriptional responses or proliferation.

Discussion

Xenoestrogen exposures have been implicated in breast cancer risk (38) as well as resistance to breast cancer treatment (39,40) due to their endocrine actions. While BP3 and PP have the potential to activate transcription from ER (7,13), they require concentrations that far exceed those found in the urine samples of most women (41,42). The median urinary level of BP3 is 0.137 µM and PP is 0.161 µM whereas transcriptional response is observed at concentrations greater than 5 µM for both chemicals. The serum levels of BP3 is reported to be approximately 0.87 µM (200 µg/L) following exposure in women (43-45). In addition, the urinary concentrations of xenoestrogens observed in pregnant women appear to be higher than the general population with median urinary concentrations of BP3 and PP being 0.47 µM and 0.253 µM, respectively and the 95th percentile concentrations in pregnant women being 29.5 µM BP3 and 3.26 µM PP (Table 2). This raises the possibility that women may have higher exposure during pregnancy due to use of creams and lotions or that absorption and metabolism may be altered in pregnancy. These compounds also have the potential to accumulate in tissues (46) although concentrations in milk appear similar to those in urine (47). However, based on measures of transcriptional activity, typical exposures to BP3 and PP would appear to pose a minimal risk for breast cancer through transcriptional activation of target genes.

Estrogens and their metabolites have been shown to induce direct DNA damage. However, DNA damage by catechol estrogens from ER-negative cell lines requires concentrations which are 100-fold greater than the average circulating concentrations in women (18, 25, 48). BP3 and PP have the potential to cause DNA damage independent of ER transactivation. BP3 has been shown to induce γH2AX foci at 10 µM concentration and increase DNA damage further upon UVB irradiation in normal human keratin cell lines (49). Treatment of Vero cells (derived from Monkey kidney) with 50 µM PP show 8-hydroxy-2-deoxyguanosine (8-OHdG) release, and γH2AX foci at 500 µM PP (50). However, these levels exceed typical concentrations measured in human populations.

Figure 6D:
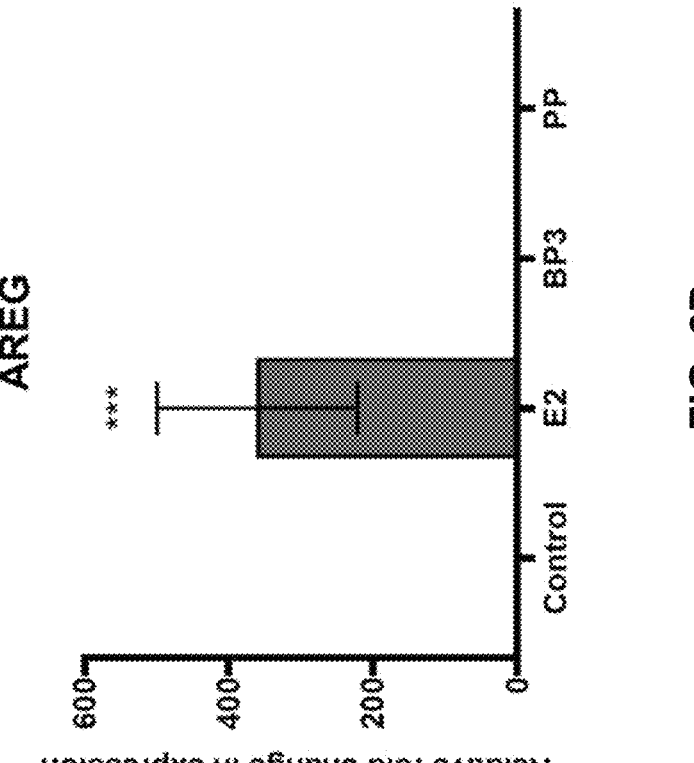
Figure 6G:
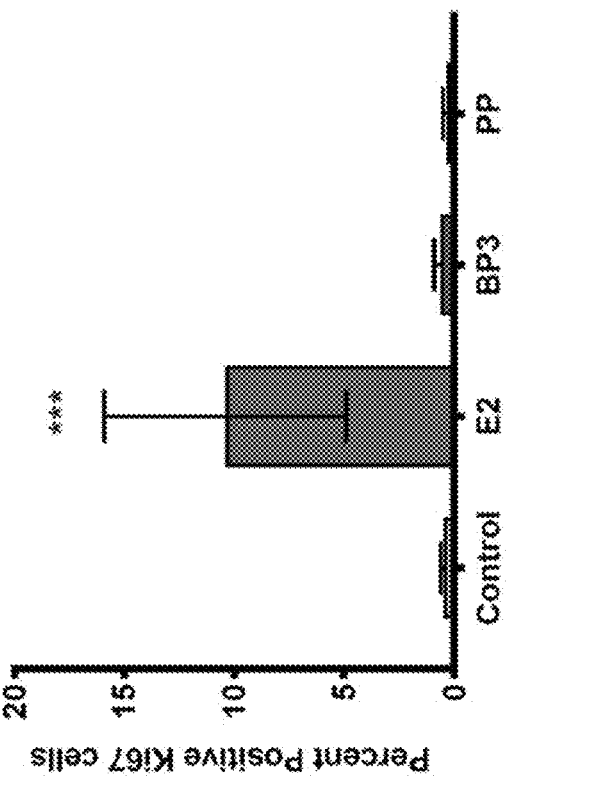
Figure 6F:
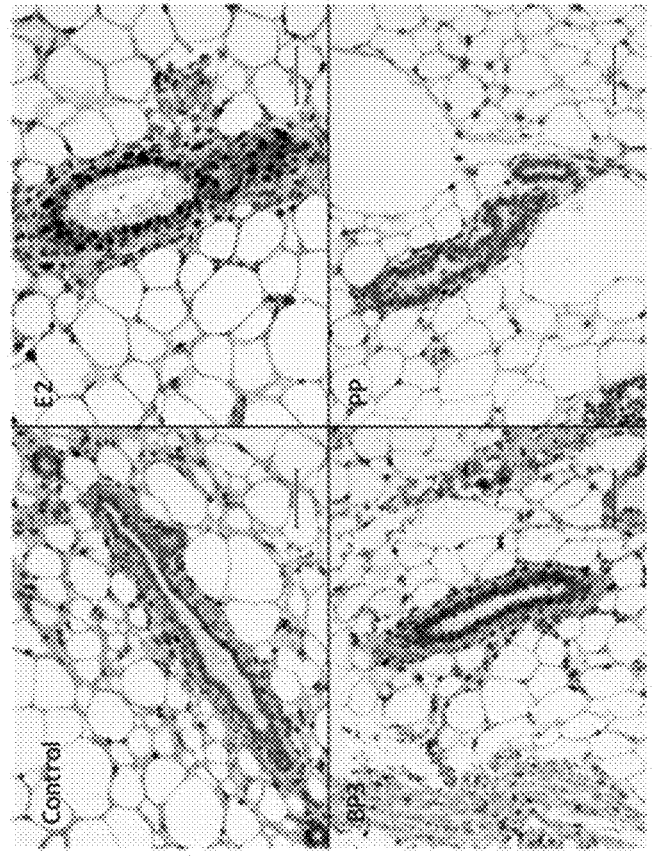

In the breast epithelial cells with functional ERα, DNA damage was observed at physiologic concentrations of E2. BP3 and PP also caused DNA damage at low concentrations (1-5 µM) (FIG. 1). Both the nuclear γH2AX intensity and 53BP1 foci were diminished by fulvestrant suggesting ERα dependency of DNA damage. At these low concentrations (1

µM of PP and 1-5 µM of BP3), no ER-mediated transcriptional response was observed in target genes. Instead, R-loop formation was observed. There was also increases in R-loops and γH2AX in the mammary epithelial cells of mice orally treated with BP3 or PP at doses designed to model environmental exposures in humans (FIG. 6D). The doses of BP3 and PP used in mice were not sufficient to affect transcription, proliferation of mammary epithelium (FIG. 6E-H, 11) or alter uterine weights compared to the control treatment in ovariectomized mice (11). These results with BP3 and PP demonstrate that the formation of R-loops and DNA damage is ER-dependent, but is separable from gene transcription and proliferative responses.

Figure 7:
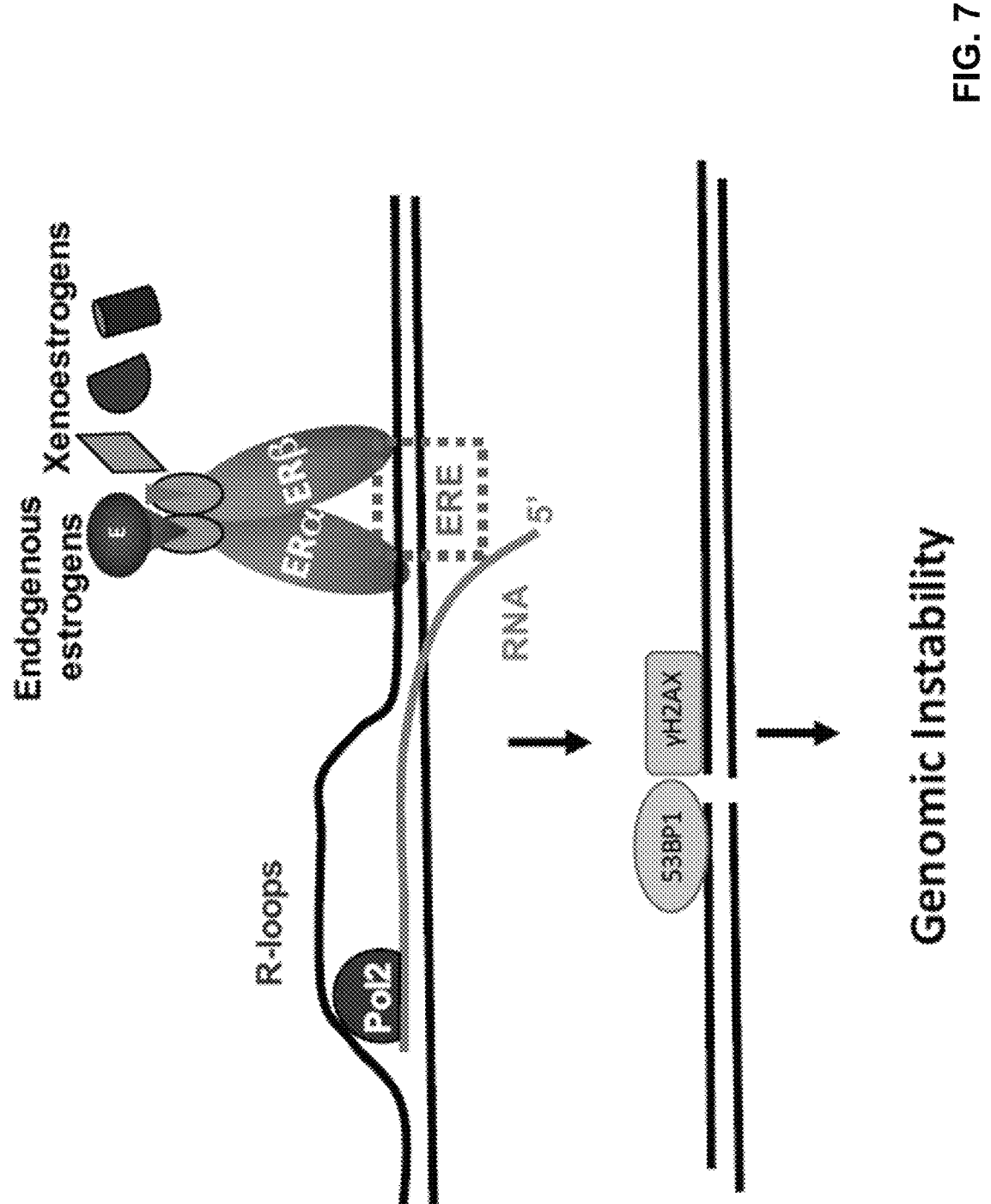

ER-mediated DNA double strand breaks have been suggested to be co-transcriptional and mediated by R-loops (32) in MCF-7 cells. Alternatively, R-loop formation can occur with RNA Polymerase II pausing which results in no increase of gene expression but leads to DNA damage (51-53). Indeed, our results show that, while E2 induced R-loop formation is co-transcriptional as BP3 and PP induce R-loops and DNA damage (FIG. 7), but do not lead to detectable increases in full-length transcripts of TFF1, AREG or PGR.

Expression of inducible ERα in the normal breast epithelial cell line 76N-Tert provides 1) additional evidence that the R-loop formation and DNA damage is ERα-dependent and 2) that normal breast epithelial cells are susceptible to DNA damage by xenoestrogens. This raises the possibility that a subset of women bearing variants of R-loop processing factors may be particularly susceptible to the genotoxic effects of xenoestrogens such as BP3 and PP. A number of such factors have been recently shown to be involved in the resolution of R-loops to limit DNA damage. These include TopI (54), BRCA1 (51), BRCA2 (52), SETX (51,55), Aquaris, (56), THO/THREX complex (57,58), BuGZ, Bub (59). For example, recruitment of BRCA1/SETX is important for R-loop mediated transcriptional termination. As a consequence, the mutational rate of termination regions where BRCA/SETX colocalize is higher in BRCA1-deficient tumors compared to BRCA1-WT tumors (51). Premalignant breast lesions such as atypical hyperplasia have elevated expression of ERα, and thus, may be especially sensitive to the genotoxic effects of these xenoestrogens. Therefore, limiting exposure to personal care products and foods containing these chemicals may be valuable for this subset of women.

These studies demonstrate that xenoestrogens have the potential for genotoxic activity that is mediated by ERα through the formation of R-loops and DNA double strand breaks. These genotoxic effects are observed at concentrations well below those necessary for detectable transcriptional activation. Therefore, R-loop forming capacity provides a valuable endpoint to consider when evaluating the safety and activity of environmental chemicals. The inducible expression of ERα in normal breast cells provides a tool with which to quantify the variation in sensitivity to these compounds among individuals and to determine if a subset of individuals is preferentially susceptible to the genotoxic activities.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating a subject without breast cancer, comprising administering to non-cancerous breast tissue in or from the subject with less than 10 µM xenoestrogen;

determining from an assay that the xenoestrogen causes estrogen receptor (ER)-mediated genotoxicity in non-cancerous breast epithelial cells of the subject; and treating the subject with an aromatase inhibitor or selective estrogen receptor degrader (SERD);

wherein ER-mediated genotoxicity is determined in the assay by the presence of DNA strand breaks, R-loops, G-quadruplexes, or a combination thereof, in the non-cancerous breast epithelial cells.

2. The method of claim 1, wherein the xenoestrogen is a selective estrogen receptor modulator (SERM).

3. The method of claim 2, wherein the SERM is tamoxifen.

4. The method of claim 1, wherein the sample is contacted with less than 5 μM xenoestrogen.

5. The method of claim 1, wherein the sample is contacted with less than 1 μM xenoestrogen.

\* \* \* \* \*

SEQUENCE LISTING

<160> NUMBER OF SEQ ID NOS: 19

<210> SEQ ID NO 1
<211> LENGTH: 36
<212> TYPE: DNA
<213> ORGANISM: Artificial Sequence
<220> FEATURE:
<223> OTHER INFORMATION: Synthetic Construct

<400> SEQUENCE: 1
gataccggta ccatggacta caaagacgat gacgac                                     36

<210> SEQ ID NO 2
<211> LENGTH: 38
<212> TYPE: DNA
<213> ORGANISM: Artificial Sequence
<220> FEATURE:
<223> OTHER INFORMATION: Synthetic Construct

<400> SEQUENCE: 2
tcgaccggta cgcgtgcgat cgctgaattc gcggcaag                                   38

<210> SEQ ID NO 3
<211> LENGTH: 32
<212> TYPE: DNA
<213> ORGANISM: Artificial Sequence
<220> FEATURE:
<223> OTHER INFORMATION: Synthetic Construct

<400> SEQUENCE: 3
gcagaaatga ccatgaccct ccacaccaaa gc                                         32

<210> SEQ ID NO 4
<211> LENGTH: 32
<212> TYPE: DNA
<213> ORGANISM: Artificial Sequence
<220> FEATURE:
<223> OTHER INFORMATION: Synthetic Construct

<400> SEQUENCE: 4
taaacgcgtt cagaccgtgg cagggaaacc ct                                         32

<210> SEQ ID NO 5
<211> LENGTH: 16
<212> TYPE: DNA
<213> ORGANISM: Artificial Sequence
<220> FEATURE:
<223> OTHER INFORMATION: Synthetic Construct

<400> SEQUENCE: 5
aattgcgcga tcgcgg                                                           16

<210> SEQ ID NO 6
<211> LENGTH: 16
<212> TYPE: DNA
<213> ORGANISM: Artificial Sequence
<220> FEATURE:
<223> OTHER INFORMATION: Synthetic Construct

<400> SEQUENCE: 6
aattccgcga tcgcgc                                                           16

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
cggtgggagg cctatataag                                                                            20

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
gctaccatta tggagtctgg                                                                            20

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
acttatatac ggttctcccc                                                                            20

<210> SEQ ID NO 10
<211> LENGTH: 21
<212> TYPE: DNA
<213> ORGANISM: Artificial Sequence
<220> FEATURE:
<223> OTHER INFORMATION: Synthetic Construct

<400> SEQUENCE: 10
cccctggtgc ttctatccta a                                                                          21

<210> SEQ ID NO 11
<211> LENGTH: 23
<212> TYPE: DNA
<213> ORGANISM: Artificial Sequence
<220> FEATURE:
<223> OTHER INFORMATION: Synthetic Construct

<400> SEQUENCE: 11
gatccctgca gaagtgtcta aaa                                                                        23

<210> SEQ ID NO 12
<211> LENGTH: 25
<212> TYPE: DNA
<213> ORGANISM: Artificial Sequence
<220> FEATURE:
<223> OTHER INFORMATION: Synthetic Construct

<400> SEQUENCE: 12
cggagaatgc aaatatatag agcac                                                                      25

<210> SEQ ID NO 13
<211> LENGTH: 22
<212> TYPE: DNA
<213> ORGANISM: Artificial Sequence
<220> FEATURE:
<223> OTHER INFORMATION: Synthetic Construct

<400> SEQUENCE: 13
caccgaaata ttcttgctga ca                                                                         22

-continued

```
<210> SEQ ID NO 14
<211> LENGTH: 20
<212> TYPE: DNA
<213> ORGANISM: Artificial Sequence
<220> FEATURE:
<223> OTHER INFORMATION: Synthetic Construct

<400> SEQUENCE: 14
tttaagaggg caatggaagg                                                    20

<210> SEQ ID NO 15
<211> LENGTH: 21
<212> TYPE: DNA
<213> ORGANISM: Artificial Sequence
<220> FEATURE:
<223> OTHER INFORMATION: Synthetic Construct

<400> SEQUENCE: 15
cggattttat caacgatgca g                                                  21

<210> SEQ ID NO 16
<211> LENGTH: 21
<212> TYPE: DNA
<213> ORGANISM: Artificial Sequence
<220> FEATURE:
<223> OTHER INFORMATION: Synthetic Construct

<400> SEQUENCE: 16
gaccacatca ggctcaatgc t                                                  21

<210> SEQ ID NO 17
<211> LENGTH: 19
<212> TYPE: DNA
<213> ORGANISM: Artificial Sequence
<220> FEATURE:
<223> OTHER INFORMATION: Synthetic Construct

<400> SEQUENCE: 17
ggtgggcctt cctaacgag                                                     19

<210> SEQ ID NO 18
<211> LENGTH: 22
<212> TYPE: DNA
<213> ORGANISM: Artificial Sequence
<220> FEATURE:
<223> OTHER INFORMATION: Synthetic Construct

<400> SEQUENCE: 18
gtcactatct ttgtctctgc ca                                                 22

<210> SEQ ID NO 19
<211> LENGTH: 24
<212> TYPE: DNA
<213> ORGANISM: Artificial Sequence
<220> FEATURE:
<223> OTHER INFORMATION: Synthetic Construct

<400> SEQUENCE: 19
cctccttctt tcttctgttt ctcc                                               24
```